US012565518B2

(12) United States Patent
Liu et al.

(10) Patent No.: US 12,565,518 B2
(45) **Date of Patent: *Mar. 3, 2026**

(54) HYBRID CYCLIC LIBRARIES AND SCREENS THEREOF

(71) Applicant: The Johns Hopkins University, Baltimore, MD (US)

(72) Inventors: Jun O. Liu, Clarksville, MD (US); Jingxin Wang, Baltimore, MD (US); Zufeng Guo, Baltimore, MD (US); Wei Li, Xiangtan (CN); Shridhar Bhat, Cockeysville, MD (US); Manisha Das, Centreville, MD (US)

(73) Assignee: The Johns Hopkins University, Baltimore, MD (US)

( * ) Notice: Subject to any disclaimer, the term of this patent is extended or adjusted under 35 U.S.C. 154(b) by 21 days.

This patent is subject to a terminal disclaimer.

(21) Appl. No.: 18/435,939

(22) Filed: Feb. 7, 2024

(65) Prior Publication Data

US 2024/0262867 A1 Aug. 8, 2024

Related U.S. Application Data

(60) Continuation of application No. 17/185,658, filed on Feb. 25, 2021, now Pat. No. 12,049,521, which is a continuation of application No. 16/563,633, filed on Sep. 6, 2019, now Pat. No. 10,954,273, which is a division of application No. 15/728,282, filed on Oct. 9, 2017, now Pat. No. 10,414,801, which is a continuation of application No. 14/987,653, filed on Jan. 4, 2016, now Pat. No. 9,783,577, which is a continuation of application No. 13/990,396, filed as application No. PCT/US2011/062471 on Nov. 29, 2011, now Pat. No. 9,250,237.

(60) Provisional application No. 61/418,038, filed on Nov. 30, 2010.

(51) Int. Cl.

| | |
|---|---|
| ***C07K 7/64*** | (2006.01) |
| ***A61K 31/4353*** | (2006.01) |
| ***A61K 31/436*** | (2006.01) |
| ***C07D 471/04*** | (2006.01) |
| ***C07D 498/04*** | (2006.01) |
| ***C07D 498/14*** | (2006.01) |
| ***C07D 515/04*** | (2006.01) |
| ***C07D 515/14*** | (2006.01) |
| ***C07K 17/08*** | (2006.01) |
| ***G01N 33/566*** | (2006.01) |

(52) U.S. Cl.

CPC .......... *C07K 7/645* (2013.01); *A61K 31/4353* (2013.01); *A61K 31/436* (2013.01); *C07D 471/04* (2013.01); *C07D 498/04* (2013.01); *C07D 498/14* (2013.01); *C07D 515/04* (2013.01); *C07D 515/14* (2013.01); *C07K 17/08* (2013.01); *G01N 33/566* (2013.01)

(58) Field of Classification Search

CPC .... A61K 31/436; A61K 31/4353; C07K 7/64; C07K 17/08; G01N 33/566

See application file for complete search history.

(56) References Cited

U.S. PATENT DOCUMENTS

| | | | |
|---|---|---|---|
| 6,984,635 B1 | 1/2006 | Schreiber et al. | |
| 7,803,808 B2 | 9/2010 | Gregory et al. | |
| 9,250,237 B2 * | 2/2016 | Liu ...................... | C07D 498/04 |
| 9,783,577 B2 | 10/2017 | Liu et al. | |
| 10,414,801 B2 | 9/2019 | Liu et al. | |
| 2009/0253732 A1 | 10/2009 | Gregory et al. | |

OTHER PUBLICATIONS

International Preliminary Report on Patentability received for PCT Patent Application No. PCT/US2011/062471, mailed Jun. 13, 2013, 6 pages.

International Search Report and Written Opinion received for PCT Patent Application No. PCT/US2011/062471, mailed May 22, 2012, 8 pages.

West, Anthony R., Solid State Chemistry and Its Applications, Wiley, New York, 1988, 358.

Zhou, Y et al., "Using the Protein Chip to Screen Agonists and Antagonists of the Androgen Receptor", Journal of Biomolecular Screening (2008), vol. 13, No. 4, pp. 276-284.

* cited by examiner

*Primary Examiner* — Erich A Leeser

(74) *Attorney, Agent, or Firm* — DLA Piper LLP (US)

(57) ABSTRACT

Provided are novel types of hybrid cyclic libraries that contain a known protein binding domain of a natural product. Also provided are synthetic methods to make such libraries and methods for the deconvolution of hits using partially split-pooled library compounds. Such methods are applicable for use with the entire human proteome to screen such libraries that bind and for the identification of hits.

8 Claims, 3 Drawing Sheets

FKBD

TOR

Effector Domain

Rapamycin

FKBD

TOR

Effector Domain

FK506

HYBRID CYCLIC LIBRARIES AND SCREENS THEREOF

CROSS REFERENCE TO RELATED APPLICATIONS

This application is a continuation application of U.S. application Ser. No. 17/185,658 filed Feb. 25, 2021, now pending; which is a continuation application of U.S. application Ser. No. 16/563,633 filed Sep. 6, 2019, now issued as U.S. Pat. No. 10,954,273; which is a divisional application of U.S. application Ser. No. 15/728,282 filed Oct. 9, 2017, now issued as U.S. Pat. No. 10,414,801; which is a continuation application of U.S. application Ser. No. 14/987,653 filed Jan. 4, 2016, now issued as U.S. Pat. No. 9,783,577; which is a continuation application of U.S. application Ser. No. 13/990,396 filed Jul. 1, 2013, now issued as U.S. Pat. No. 9,250,237; which is a 35 USC § 371 National Stage application of International Application No. PCT/US2011/062471 filed Nov. 29, 2011, now expired; which claims the benefit under 35 USC § 119(e) to U.S. Application Ser. No. 61/418,038 filed Nov. 30, 2010. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. CA174428 awarded by the National Institutes of Health. The government has certain rights in the invention.

BACKGROUND OF THE INVENTION

Field of the Invention

The invention relates generally to hybrid cyclic molecules, and more specifically to hybrid cyclic libraries based on the immunophilin ligand family of natural products cyclosporine A (CsA), FK506, and rapamycin, and methods of screening proteins encoded by a genome on a protein chip or in cell- and target-based assays for elucidation of the proteins' function.

Background Information

The immunophilin ligand family consists of three members, cyclosporine A (CsA), FK506 and rapamycin, all of which are natural products with potent immunosuppressive or anticancer activities. Unlike other bioactive small molecules, these natural products have an unprecedented and extraordinary mode of action-through induction of dimeric ternary complexes between two distinct proteins. They each bind to abundant and small cytosolic immunophilins, which also possess peptidyl prolyl cis-trans isomerase activity and are implicated in protein folding. Thus, CsA binds the cyclophilin (CyP) family of immunophilins; FK506 and rapamcyin both bind FKBP. The formation of the immunophilin-drug complexes per se does not have significant cellular consequences. It is the subsequent binding of these complexes to their respective target proteins that leads to inhibition of T cell activation or tumor cell growth. In the case of CsA and FK506, the CyP-CsA and FKBP-FK506 complexes bind to and inhibit the enzymatic activity of the protein phosphatase calcineurin. In the case of rapamycin, the FKBP-rapamycin complex binds to the PI3 kinase homologue, Target of Rapamycin (TOR). There are a number unique properties associated with this family of natural products. First, they are capable of targeting a relatively large surface of target protein through recruitment of the corresponding immunophilins, capable of inhibiting protein-protein interactions in addition to enzymatic activity of individual protein targets. Second, through their association with immunophilins, they are more stable and less susceptible to degradation in vivo through interaction with immunophilins in both blood and in red blood cells. Third, the immunophilin-binding domains confer intrinsic stabilities to the macrocycles. Thus, macrocyles containing the FKBP- or CyP-binding domains have great potential as new leads for developing drugs to be used for treating diseases.

With the completion of the sequencing and annotation of the human genome, we now have a complete catalog of all human proteins encoded in the genome. The functions of a majority of these proteins, however, remain unknown. One way to elucidate the functions of these proteins is to find small molecule ligands that specifically bind to the proteins of interest and perturb their biochemical and cellular functions. Thus, a major challenge for chemical biologists today is to discover new small molecule probes for new proteins to facilitate the elucidation of their functions. The recent advance in the development of protein chips has offered an exciting new opportunity to simultaneously screen chemical libraries against nearly the entire human proteome. A single chip, in the form of a glass slide, is sufficient to display an entire proteome in duplicate arrays. Recently, a protein chip with 17,000 human proteins displayed on a single slide has been produced. A major advantage of using human protein chips for screening is that the entire displayed proteome can be interrogated at once in a small volume of assay buffer (<3 mL). Screening of human protein chips, however, is not yet feasible with most, if not all, existing chemical libraries due to the lack of a universal readout for detecting the binding of a ligand to a protein on these chips. While it is possible to add artificial tags to individual compounds in a synthetic library, often the added tags themselves interfere with the activity of ligands. Thus, there remains a need for new compounds and methods for screening chemical libraries against the human proteome.

SUMMARY OF THE INVENTION

The present invention solves these problems and others by providing new compounds and methods for screening chemical libraries against the proteins encoded by a genome.

Thus, in one embodiment, the disclosure provides a compound of Formula I:

(I)

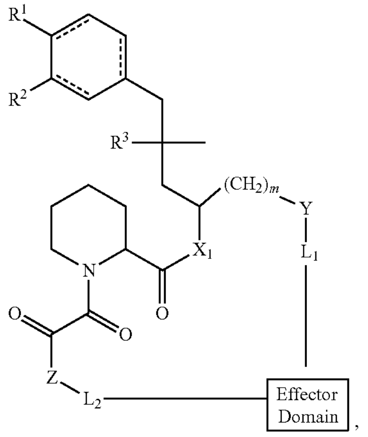

or a pharmaceutically acceptable salt or solvate thereof, wherein:

------- is a single or double bond;

$X_1$ is O or $NR^6$;

Y is —C(O)— or

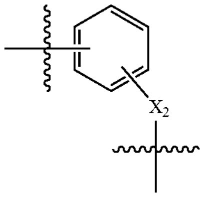

;

$X_2$ is $(CH_2)_m$, O, or $NR^6$;

Z is

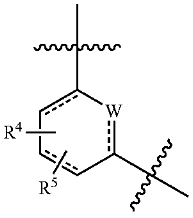

or

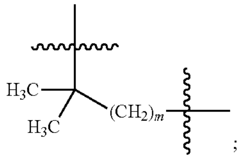

;

W is O, CH, $CH_2$, $CR^4$, or $CR^5$;

$L_1$ and $L_2$ are each independently a direct bond, substituted or unsubstituted —$(C_1$-$C_6)$alkyl-, substituted or unsubstituted —$(CH_2)_n$O$(C_1$-$C_6)$alkyl-, substituted or unsubstituted —$(CH_2)_n$C(O)—, substituted or unsubstituted —$(CH_2)_n$C(O)$(C_1$-$C_6)$alkyl-, substituted or unsubstituted —$(CH_2)_n$C(O)O$(C_1$-$C_6)$alkyl-, substituted or unsubstituted —$(CH_2)_n$NH$(C_1$-$C_6)$alkyl-, substituted or unsubstituted —$(CH_2)_n$C(O)NH$(C_1$-$C_6)$alkyl-, substituted or unsubstituted —$(CH_2)_n$S$(C_1$-$C_6)$alkyl-, substituted or unsubstituted —$(CH_2)_n$C(O)$(CH_2)_n$S$(C_1$-$C_6)$alkyl-, substituted or unsubstituted —$(C_2$-$C_6)$alkenyl-, substituted or unsubstituted —$(CH_2)_n$O$(C_2$-$C_6)$alkenyl-, substituted or unsubstituted —$(CH_2)_n$C(O)$(C_2$-$C_6)$alkenyl-, substituted or unsubstituted —$(CH_2)_n$C(O)O$(C_2$-$C_6)$alkenyl-, substituted or unsubstituted —$(CH_2)_n$NH$(C_1$-$C_6)$alkenyl-, substituted or unsubstituted —$(CH_2)_n$C(O)NH$(C_2$-$C_6)$alkenyl-, substituted or unsubstituted —$(CH_2)_n$S$(C_2$-$C_6)$alkenyl-, substituted or unsubstituted —$(CH_2)_n$C(O)$(CH_2)_n$S$(C_2$-$C_6)$alkenyl-, substituted or unsubstituted —$(C_2$-$C_6)$alkynyl-, substituted or unsubstituted —$(CH_2)_n$O$(C_2$-$C_6)$alkynyl-, substituted or unsubstituted —$(CH_2)_n$C(O)$(C_2$-$C_6)$alkynyl-, substituted or unsubstituted —$(CH_2)_n$C(O)O$(C_2$-$C_6)$alkynyl-, substituted or unsubstituted —$(CH_2)_n$NH$(C_1$-$C_6)$alkynyl-, substituted or unsubstituted —$(CH_2)_n$C(O)NH$(C_2$-$C_6)$alkynyl-, substituted or unsubstituted —$(CH_2)_n$S$(C_2$-$C_6)$alkynyl-, substituted or unsubstituted —$(CH_2)_n$C(O)$(CH_2)_n$S$(C_2$-$C_6)$alkynyl-, wherein each alkyl, alkenyl and alkynyl group may be optionally substituted with alkyl, alkoxy, amino, carboxyl, cyano, nitro, or trifluoromethyl;

each m is independently an integer selected from 0, 1, 2, 3, 4, 5, and 6;

each n is independently an integer selected from 0, 1, 2, 3, 4, 5, and 6;

$R^1$ is hydrogen, hydroxyl, or OPG, wherein PG is a protecting group, or $R^1$ is

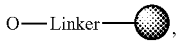

, wherein

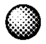

is a resin;

$R^2$ is hydrogen, hydroxyl, or alkoxy;

$R^3$ is hydrogen or alkyl;

$R^4$ and $R^5$ are each independently hydrogen, hydroxy, alkyl, alkoxy, or OPG, wherein PG is a protecting group;

$R^6$ is hydrogen or alkyl;

wherein the Effector Domain has Formula II:

(II)

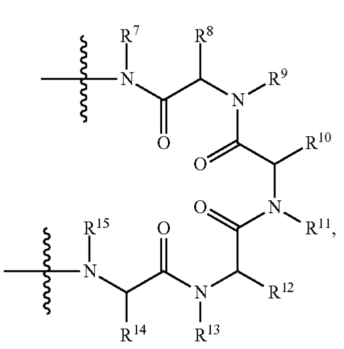

wherein:

$R^7$, $R^9$, $R^{11}$, $R^{13}$, and $R^{15}$ are each independently hydrogen or alkyl;

$R^8$, $R^{10}$, $R^{12}$, and $R^{14}$ are each independently hydrogen, halogen, amino, cyano, nitro, trifluoromethyl, substituted or unsubstituted alkyl, substituted or unsubstituted tuted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)_nN^{19}RC(O)R^{16}$, $(CH_2)_nN^{19}RC(O)OR^{16}$, $(CH_2)$, $NR^{19}C(O)NR^{17}R^{18}$, $(CH_2)_nSR^{16}$, $(CH_2)_nS(O)_jNR^{17}R^{18}$, $(CH_2)_nN^{19}RS(O)_jR^{16}$, or $—(CH_2)_nNR^{19}S(O)_jNR^{17}R^{18}$;

n is an integer selected from 0, 1, 2, 3, 4, 5, and 6;

j is an integer selected from 0, 1, and 2;

$R^{16}$, $R^{17}$, $R^{18}$, and $R^{19}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{16}$ and $R^{19}$ are as described above, and $R^{17}$ and $R^{18}$, together with the N atom to which they are attached, form a substituted or unsubstituted 5-, 6-, or 7-membered heterocycloalkyl or a substituted or unsubstituted 5-membered heteroaryl, wherein each of the above groups listed for $R^8$, $R^{10}$, $R^{12}$, and $R^{14}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)$, $N^{19}RC(O)R^{16}$, $(CH_2)$, $N^{19}RC(O)OR^{16}$, $(CH_2)$, $NR^{19}C(O)NR^{17}R^{18}$, $(CH_2)_nSR^{16}$, $(CH_2)_nS(O)_jNR^{17}R^{18}$, $(CH_2)$, $N^{19}RS(O)_jR^{16}$, and $—(CH_2)$, $NR^{19}S(O)_jNR^{17}R^{18}$.

In another embodiment, the disclosure provides methods for treating cancer in a patient in need thereof by administering a compound of Formula I to the patient.

In another embodiment, the disclosure provides methods for suppressing the immune system in a patient in need thereof by administering the compound of Formula I to the patient.

In another embodiment, the disclosure provides methods for preparing the compound of Formula I.

In another embodiment, the disclosure provides methods for determining the function of a protein encoded in the human genome by:

a) screening a hybrid combinatorial peptide or non-peptide library of compounds that includes the FKBP-binding domain (FKBP) of the natural product rapamycin or FK506 against the proteins encoded in the human genome using a human protein chip;
b) detecting the binding of a compound to a protein on the chip using the anti-V5 antibody together with a fluorescently tagged secondary antibody;
c) recording the fluorescence pattern of the human protein chip on a chip reader;
d) identifying the proteins based on the physical location of the fluorescent spots on the chip; and
e) determining the function of the protein based on its perturbed biochemical and cellular functions.

In another embodiment, the disclosure provides methods for generating a lead compound as a high-affinity ligand of the FKBP isoforms, the method comprising the steps of:

a) screening a hybrid combinatorial peptide or non-peptide library of compounds that includes the FKBP-binding domain (FKBP) of the natural product rapamycin or FK506 against the proteins encoded in the human genome using a human protein chip;
b) detecting the binding of a compound to a protein on the chip using the anti-V5 antibody together with a fluorescently tagged secondary antibody;
c) recording the fluorescence pattern of the human protein chip on a chip reader;
d) identifying the proteins based on the physical location of the fluorescent spots on the chip; and
e) determining the structure of the lead compound.

DETAILED DESCRIPTION OF THE INVENTION

Figure 1:
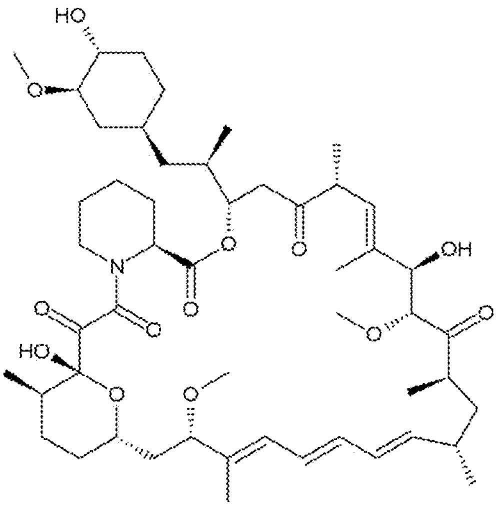
FIG. 1 shows rapamycin and FK506 and their respective cellular targets.
Figure 1:
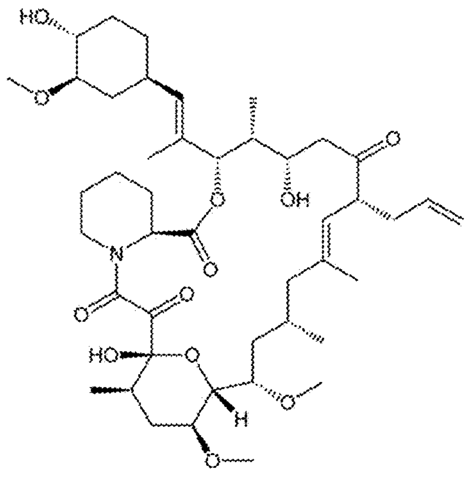

Abbreviations used herein have their conventional meaning within the chemical and biological arts.

As used herein, the terms "a," "an," or "a(n)," when used in reference to a group of substituents, mean at least one. For example, where a compound is substituted with "an" alkyl or "an" aryl, the compound is optionally substituted with at least one alkyl and/or at least one aryl group. Moreover, where a moiety is substituted with a R substituent, the group may be referred to as "R-substituted." Where a moiety is R-substituted, the moiety is substituted with at least one R substituent and each R substituent is optionally different.

The description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The symbol "-" and "~" denote the point of attachment of a moiety to the remainder of the molecule.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., $C_1$-$C_6$ means one to six carbons; and $C_1$-$C_{10}$ means one to ten carbons).

Examples of saturated hydrocarbon radicals include, but are not limited to, groups such as methyl, ethyl, N-propyl, isopropyl, N-butyl, t-butyl, isobutyl, sec-butyl, cyclohexyl, (cyclohexyl)methyl, cyclopropylmethyl, homologs and isomers of, for example, N-pentyl, N-hexyl, N-heptyl, N-octyl, and the like. An unsaturated alkyl group is one having one or more double bonds or triple bonds for example, alkenyl and alkynyl groups, respectively.

Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by $—CH{=}CH_2—$, $—CH_2CH{=}CH_2—$, $—CH_2CH{=}CHCH_2—$, $—CH_2CH_2CH{=}CH_2—$, and $—CH{=}CHCH(CH_2CH_2CH_3)CH_2—$. Typically, an alkyl (or alkylene) group will have from 1 to 24 carbon atoms, while other alkyl (or alkylene) groups will have 10 or fewer carbon atoms. A "lower alkyl" or "lower alkylene" is a shorter chain alkyl or alkylene group, generally having eight or fewer carbon atoms, typically one to six carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule.

Examples of heteroalkyl include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $O—CH_3$, $—O—CH_2—CH_3$ and —CN. In addition, up to two or three heteroatoms may be consecutive, such as, for example, $—CH_2—NH—OCH_3$ and $—CH_2—O—Si(CH_3)_3$.

The term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" and the like, it is understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" and the like.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (usually from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized.

A heteroaryl group can be attached to the remainder of the molecule through a carbon or heteroatom. Non-limiting examples of aryl and heteroaryl groups include but are not limited to phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Where a heteroalkyl, heterocycloalkyl, or heteroaryl includes a specific number of members (e.g., "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl," "aryl," "heteroaryl" as well as their divalent radical derivatives) are meant to include both substituted and unsubstituted forms of the indicated radical. Examples of substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R"', —OC(O)R', —C(O)R', —$CO_2$R', —C(O)NR'R", —OC(O)NR'R", —NR'C(O)R", —NR'—C(O)NR"R"', —NR'C(O)OR", —NR'—C(NR"R"')═NR"", —S(O)R', —$S(O)_2$R', —$S(O)_2$NR'R", —NR'$SO_2$R", —CN and —$NO_2$ in a number ranging from zero to (2m'+1), where $m^1$ is the total number of carbon atoms in such radical. R', R", R"' and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R' and R"" groups when more than one of these groups is present. When R"' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R"', —OC(O)R, —C(O)R', —$CO_2$R', —C(O)NR'R", —OC(O)NR'R", —NR'C(O)R", —NR'—C(O)NR" R"', —NR'C(O)OR", —NR'—C(NR'N"R"')═NR', —NR'—C(NR'R")═NR"', —S(O)R', —$S(O)_2$R', —$S(O)_2$NR'R", —NR'$SO_2$R", —CN and —$NO_2$, —$N_3$, —CH$(Ph)_2$, fluoro($C_1$-$C_4$)alkoxy, in a number ranging from zero to the total number of open valences on aromatic ring system; and where R', R", R"' and R"" are each independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—$(CR'R")_q$—U—, wherein T and U are independently —NR—, —O—, —CR'R"— or a single bond, and q is an integer of from 0 to 3. Alternatively, two of the substituents on adjacent atoms of aryl or heteroaryl ring may optionally be replaced with a substituent of the formula -A-$(CH_2)_r$—B—, wherein A and B are independently —CR'R"—, —O—, —NR'—, —S—, —S(O)—, —$S(O)_2$—, —$S(O)_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —$(CR'R")_s$—$X^1$—$(CR"'R"")_d$—, where s and d are independently integers of from 0 to 3, and X is —O—, —NR'—, —S—, —S(O)—, —$S(O)_2$—, or —$S(O)_2$NR'—. The substituents R', R", R"' and R"" are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

I oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_6$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, mono-hydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methane sulfonic, and the like. Also included are salts of amino acids such as arginate and the like, and salts of organic acids like glucuronic or galactunoric acids and the like {see, e.g., Berge et al., Journal of Pharmaceutical Science, 66:1-19 (1977)). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Protecting groups are commonly used in organic synthesis in order to protect various functional groups, including but not limited to amino, carbonyl, carboxyl, hydroxyl, 1,2-diols and 1,3-diols. One of skill in the art would know which functional groups would require protection, how to select an appropriate protecting group as well as how to prepare and remove such groups in order to unmask the pre-existing functional group (T. W. Green, P. G. M. Wuts, Protective Groups in Organic Synthesis, Wiley-Interscience, New York, 1999).

Common amino protecting groups include but are not limited to 9-fluorenylmethyl carbamate, t-butyl carbamate, benzyl carbamate, acetamide, trifluoroacetamide, phthalimide, benzylamine, triphenylmethylamine, benzylideneamine, p-toluenesulfonamide, and the like.

Common carbonyl protecting groups include but are not limited to dimethyl acetal, 1,3-dioxane, 1,3-dithiane, N,N-dimethylhydrazone, and the like.

Common carboxyl protecting groups include but are not limited to methyl ester, t-butyl ester, benzyl ester, S-t-butyl ester, 2-alkyl-1,3-oxazoline, and the like.

Common hydroxyl protecting groups include but are not limited to methoxymethyl ether (MOM), tetrahydropyranyl ether (THP), tert-butyl ether (t-Bu), allyl ether, benzyl ether, tert-butyldimethylsilyl ether (TBDMS), t-butyldiphenylsilyl ether (TBDPS), acetic acid ester, pivalic acid ester, benzoic acid ester, and the like.

Common 1,2- and 1,3-diol protecting groups include but are not limited to acetonide, benzylidene acetal, and the like.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another. It is apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention. The compounds of the present invention may also contain unnatural proportions of atomic isotopes at one or more of atoms that constitute such compounds. For example, the compounds may be radiolabeled with radioactive isotopes, such as for example tritium (3H), iodine-125 ($^{125}I$) or carbon-14 ($^{14}C$). All isotopic variations of the compounds of the present invention, whether radioactive or not, are encompassed within the scope of the present invention.

The term "subject," "patient," or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treating" or "treatment" in reference to a particular disease includes prevention of the disease. The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. In some embodiments, for prophylactic benefit, the compositions are administered to a patient at risk of developing a particular disease, or to a patient reporting one or more of the physiological symptoms of a disease, even though a diagnosis of this disease may not have been made.

The term "pharmaceutically acceptable" as used herein, refers to a material, such as a carrier or diluent, which does not abrogate the biological activity or properties of the compounds described herein, and is relatively nontoxic, i.e., in other embodiments, the material is administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of the compound into cells or tissues.

The term "agonist," as used herein, refers to a molecule such as the compound, a drug, an enzyme activator or a hormone modulator which enhances the activity of another molecule or the activity of a receptor site.

The term "antagonist," as used herein, refers to a molecule such as the compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable derivative or prodrug" as used herein, refers to any pharmaceutically acceptable salt, ester, salt of an ester or other derivative of the compound of Formula I, which, upon administration to a recipient, is capable of providing, either directly or indirectly, the compound disclosed herein or a pharmaceutically active metabolite or residue thereof. Particularly favored derivatives or prodrugs are those that increase the bioavailability of the compounds described herein when such compounds are administered to a patient (e.g., by allowing orally administered compound to be more readily absorbed into blood) or which enhance delivery of the parent compound to a biological compartment (e.g., the brain or lymphatic system).

The terms “enhance” or “enhancing,” as used herein, means to increase or prolong either in potency or duration a desired effect. Thus, in regard to enhancing the effect of therapeutic agents, the term “enhancing” refers to the ability to increase or prolong, either in potency or duration, the effect of other therapeutic agents on a system. An “enhancing-effective amount,” as used herein, refers to an amount adequate to enhance the effect of another therapeutic agent in a desired system.

The term “metabolite,” as used herein, refers to a derivative of the compound which is formed when the compound is metabolized.

The term “active metabolite,” as used herein, refers to a biologically active derivative of the compound that is formed when the compound is metabolized.

The term “metabolized,” as used herein, refers to the sum of the processes (including, but not limited to, hydrolysis reactions and reactions catalyzed by enzymes) by which a particular substance is changed by an organism. Thus, in some embodiments, enzymes produce specific structural alterations to the compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

The term “genome” includes but is not limited to the human genome. Other genomes include for example: viruses, for example, bacteriophage MS2, SV40, phage Φ-X17, HIV, phage λ, and mimivirus; bacterium, for example, *Haemophilus influenzae, Carsonella ruddi, Buchnera aphidicola, Wigglesworthia glossinidia*, and *Escherichia Coli*; amoeboid, for example, *Polychaos dubium* (“Amoeba” *dubia*); plant, for example, *Arabidopsis thaliana, Genlisea margaretae, Fritillaria assyrica, Populus trichocarpa*, and paris *Japonica* (Japanese-native, pale-petal); Moss, for example, *Physcomitrella patens*; yeast, for example, *Saccharomyces cerevisiae*; fungus, for example, *Aspergillus nidulans*; nematode, for example, *Caenorhabditis elegans* and *Pratylenchus coffeae*; insect, for example, *Drosophila melanogaster* (fruit fly), *Bombyx mori* (silk moth), *Apis mellifera* (honey bee), *Solenopsis invicta* (fire ant), *Tetraodon nigroviridis* (type of puffer fish); mammal, for example, *Homo sapiens* (humans); and fish, for example, *Protopterus aethiopicus* (marbled lungfish) and the like.

Hybrid Cyclic Libraries

In one embodiment the disclosure provides a compound of Formula I:

(I)

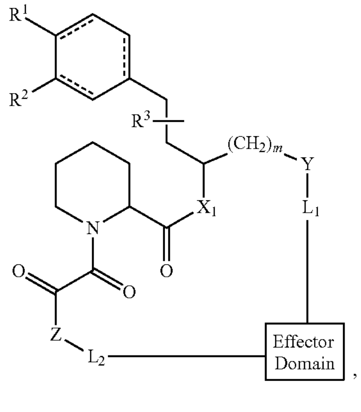

, or a pharmaceutically acceptable salt or solvate thereof, wherein:

------- is a single or double bond;

$X_1$ is O or $NR^6$;

Y is —C(O)— or

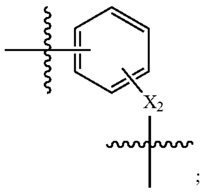

;

$X_2$ is $(CH_2)_m$, O, or $NR^6$;

Z is

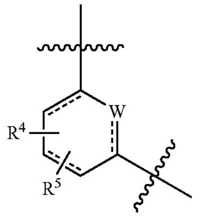

or

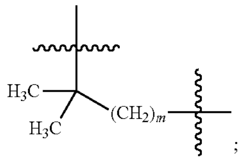

;

W is O, CH, $CH_2$, $CR^4$, or $CR^5$;

$L_1$ and $L_2$ are each independently a direct bond, substituted or unsubstituted —$(C_1$-$C_6)$alkyl-, substituted or unsubstituted —$(CH_2)_nO(C_1$-$C_6)$alkyl-, substituted or unsubstituted —$(CH_2)_nC(O)$—, substituted or unsubstituted —$(CH_2)_nC(O)(C_1$-$C_6)$alkyl-, substituted or unsubstituted —$(CH_2)_nC(O)O(C_1$-$C_6)$alkyl-, substituted or unsubstituted —$(CH_2)_nNH(C_1$-$C_6)$alkyl-, substituted or unsubstituted —$(CH_2)_nC(O)NH(C_1$-$C_6)$alkyl-, substituted or unsubstituted —$(CH_2)_nS(C_1$-$C_6)$alkyl-, substituted or unsubstituted —$(CH_2)_nC(O)(CH_2)_nS(C_1$-$C_6)$alkyl-, substituted or unsubstituted —$(C_2$-$C_6)$alkenyl-, substituted or unsubstituted —$(CH_2)_nO(C_2$-$C_6)$alkenyl-, substituted or unsubstituted —$(CH_2)_nC(O)(C_2$-$C_6)$alkenyl-, substituted or unsubstituted —$(CH_2)_nC(O)O(C_2$-$C_6)$alkenyl-, substituted or unsubstituted —$(CH_2)_nNH(C_1$-$C_6)$alkenyl-, substituted or unsubstituted —$(CH_2)_nC(O)NH(C_2$-$C_6)$alkenyl-, substituted or unsubstituted —$(CH_2)_nS(C_2$-$C_6)$alkenyl-, substituted or unsubstituted —$(CH_2)_nC(O)(CH_2)_nS(C_2$-$C_6)$alkenyl-, substituted or unsubstituted —$(C_2$-$C_6)$alkynyl-, substituted or unsubstituted —$(CH_2)_nO(C_2$-$C_6)$alkynyl-, substituted or unsubstituted —$(CH_2)_nC(O)(C_2$-$C_6)$alkynyl-, substituted or unsubstituted —$(CH_2)_nC(O)O(C_2$-$C_6)$alkynyl-, substituted or unsubstituted —$(CH_2)_nNH(C_1$-$C_6)$alkynyl-, substituted or unsubstituted —$(CH_2)_nC(O)NH(C_2$-$C_6)$alkynyl-, substituted or unsubstituted —$(CH_2)_nS(C_2$-$C_6)$alkynyl-, substituted or unsubstituted —$(CH_2)_nC(O)(CH_2)_nS(C_2$-$C_6)$alkynyl-, wherein each alkyl, alkenyl and alkynyl group may be optionally substituted with alkyl, alkoxy, amino, carboxyl, cyano, nitro, or trifluoromethyl;

each m is independently an integer selected from 0, 1, 2, 3, 4, 5, and 6;

each n is independently an integer selected from 0, 1, 2, 3, 4, 5, and 6;

$R^1$ is hydrogen, hydroxyl, or OPG, wherein PG is a protecting group, or $R^1$ is

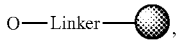

wherein

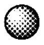

is a resin;

$R^2$ is hydrogen, hydroxyl, or alkoxy;

$R^3$ is hydrogen or alkyl;

$R^4$ and $R^5$ are each independently hydrogen, hydroxy, alkyl, alkoxy, or OPG, wherein PG is a protecting group;

$R^6$ is hydrogen or alkyl;

wherein the Effector Domain has Formula II:

(II)

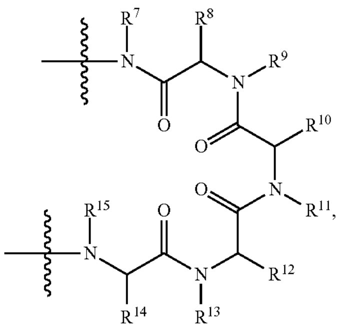

wherein:

$R^7$, $R^9$, $R^{11}$, $R^{13}$, and $R^{15}$ are each independently hydrogen or alkyl;

$R^8$, $R^{10}$, $R^{12}$, and $R^{14}$ are each independently hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)_nN^{19}RC(O)R^{16}$, $(CH_2)_nN^{19}RC(O)OR^{16}$, $(CH_2)$, $NR^{19}C(O)NR^{17}R^{18}$, $(CH_2)_nSR^{16}$, $(CH_2)_nS(O)_jNR^{17}R^{18}$, $(CH_2)$, $N^{19}RS(O)_jR^{16}$, or $—(CH_2)_nNR^{19}S(O)_jNR^{17}R^{18}$;

n is an integer selected from 0, 1, 2, 3, 4, 5, and 6;

j is an integer selected from 0, 1, and 2;

$R^{16}$, $R^{17}$, $R^{18}$, and $R^{19}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{16}$ and $R^{19}$ are as described above, and $R^{17}$ and $R^{18}$, together with the N atom to which they are attached, form a substituted or unsubstituted 5-, 6-, or 7-membered heterocycloalkyl or a substituted or unsubstituted 5-membered heteroaryl, wherein each of the above groups listed for $R^8$, $R^{10}$, $R^{12}$, and $R^{14}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)$, $N^{19}RC(O)R^{16}$, $(CH_2)_nN^{19}RC(O)OR^{16}$, $(CH_2)_nNR^{19}C(O)NR^{17}R^{18}$, $(CH_2)_nSR^{16}$, $(CH_2)_nS(O)_jNR^{17}R^{18}$, $(CH_2)$, $N^{19}RS(O)_jR^{16}$, and $—(CH_2)$, $NR^{19}S(O)_jNR^{17}R^{18}$.

In another embodiment, the disclosure provides a compound of Formula I, wherein:

X is O or $NR^6$;

$L_1$ and $L_2$ are each independently $—(C_1\text{-}C_6)$alkyl-, $—(CH_2)_nO(C_1\text{-}C_6)$alkyl-, $—(CH_2)_nC(O)(C_1\text{-}C_6)$alkyl-, $—(CH_2)_nC(O)O(C_1\text{-}C_6)$alkyl-, $—(CH_2)_nNH(C_1\text{-}C_6)$alkyl-, $—(CH_2)_nC(O)NH(C_1\text{-}C_6)$alkyl-, $—(CH_2)_nS(C_1\text{-}C_6)$alkyl-, $—(CH_2)_nC(O)(CH_2)_nS(C_1\text{-}C_6)$alkyl-, $—(C_2\text{-}C_6)$alkenyl-, $—(CH_2)_nO(C_2\text{-}C_6)$alkenyl-, $—(CH_2)_nC(O)(C_2\text{-}C_6)$alkenyl-, $—(CH_2)_nC(O)O(C_2\text{-}C_6)$alkenyl-, $—(CH_2)_nNH(C_1\text{-}C_6)$alkenyl-, $—(CH_2)_nC(O)NH(C_2\text{-}C_6)$alkenyl-, $—(CH_2)_nS(C_2\text{-}C_6)$alkenyl-, $—(CH_2)_nC(O)(CH_2)_nS(C_2\text{-}C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl, or OPG, wherein PG is a silyl protecting group, or $R^1$ is

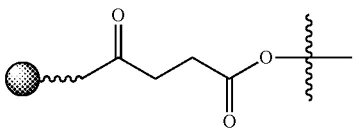

or

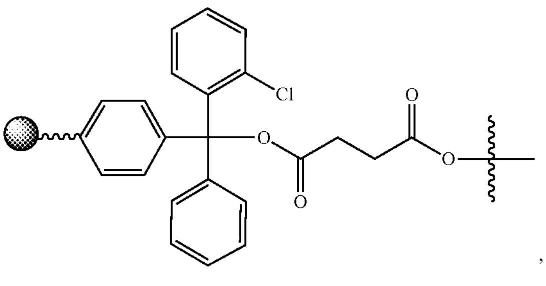

, wherein

is a resin;

$R^2$ is hydroxyl or alkoxy;

$R^3$ is hydrogen or alkyl;

$R^4$ and $R^5$ are each independently hydrogen, alkyl, alkoxy, or OPG, wherein PG is a silyl protecting group;

$R^6$ is hydrogen;

$R^7$, $R^9$, $R^{10}$, $R^{13}$, and $R^{15}$ are each independently hydrogen or $CH_3$;

$R^8$, $R^{10}$, $R^{12}$, and $R^{14}$ are each independently substituted or unsubstituted cyclopropyl, substituted or unsubstituted cyclobutyl, substituted or unsubstituted cyclopentyl, substituted or unsubstituted cyclohexyl, substituted or unsubstituted cycloheptyl, or substituted or unsubstituted cyclooctyl; or $R^8$, $R^{10}$, $R^{12}$, and $R^{14}$ are each independently substituted or unsubstituted tetrahydrofuranyl, substituted or unsubstituted tetrahydrothiophenyl, substituted or unsubstituted pyrrolidinyl, substituted or unsubstituted 1,3-dioxolanyl, substituted or unsubstituted pyrazolidinyl, substituted or unsubstituted imidazolidinyl, substituted or unsubstituted 1,4-dioxanyl, substituted or unsubstituted piperidinyl, substituted or unsubstituted piperazinyl, substituted or unsubstituted morpholinyl, substituted or unsubstituted thiomorpholinyl, or substituted or unsubstituted 1,4-dithianyl; or $R^8$, $R^{10}$, $R^{12}$, and $R^{14}$ are each independently substituted or unsubstituted phenyl, substituted or unsubstituted benzyl, substituted or unsubstituted naphthylenyl, or substituted or unsubstituted biphenyl; or $R^8$, $R^{10}$, $R^{12}$, and $R^{14}$ are each independently substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted triazolyl, substituted or unsubstituted isoxazolyl, substituted or unsubstituted oxazolyl, substituted or unsubstituted thiazolyl, substituted or unsubstituted isothiazolyl, substituted or unsubstituted pyridinyl, substituted or unsubstituted pyridizanyl, substituted or unsubstituted pyrimidinyl, substituted or unsubstituted triazinyl, substituted or unsubstituted benzofuranyl, substituted or unsubstituted benzo(b)thiophenyl, substituted or unsubstituted indolyl, substituted or unsubstituted benzimidazolyl, substituted or unsubstituted indazolyl, substituted or unsubstituted benzisoxazolyl, substituted or unsubstituted benzoxazolyl, substituted or unsubstituted benzothiazolyl, substituted or unsubstituted quinolinyl, substituted or unsubstituted isoquinolinyl, substituted or unsubstituted quinazolinyl, substituted or unsubstituted quinoxalinyl, or substituted or unsubstituted naphthyridinyl.

In another embodiment, the disclosure provides a compound of Formula I, wherein:

$L_1$ and $L_2$ are each independently —$(C_1$-$C_6)$alkyl-, —$(CH_2)_nO(C_1$-$C_6)$alkyl-, —$(CH_2)_nC(O)(C_1$-$C_6)$alkyl-, —$(CH_2)_nNH(C_1$-$C_6)$alkyl-, —$(CH_2)_nC(O)NH(C_1$-$C_6)$alkyl-, —$(C_2$-$C_6)$alkenyl-, —$(CH_2)_nO(C_2$-$C_6)$alkenyl-, —$(CH_2)_nC(O)(C_2$-$C_6)$alkenyl-, —$(CH_2)_nNH(C_1$-$C_6)$alkenyl-, —$(CH_2)_nC(O)NH(C_2$-$C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl or OPG, wherein PG is a tert-butyldimethylsilyl protecting group, or $R^1$ is

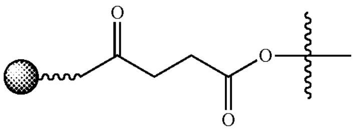

or

-continued

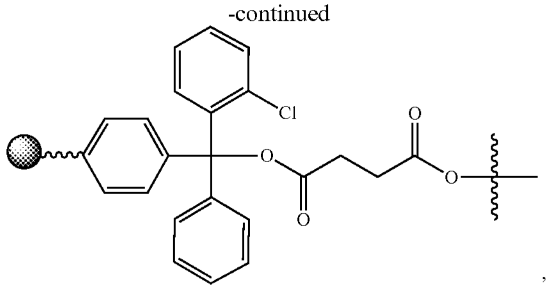

, wherein

is Wang resin;

$R^4$ and $R^5$ are each independently hydrogen, hydroxy, alkyl, alkoxy, or OPG, wherein PG is a tert-butyldimethylsilyl protecting group;

$R^7$, $R^9$, $R^{11}$, $R^{13}$, and $R^{15}$ are each independently hydrogen;

$R^8$, $R^{10}$, $R^{12}$, and $R^{14}$ are each independently hydrogen, substituted or unsubstituted alkyl, substituted or unsubstituted benzyl, substituted or unsubstituted pyrrolidinyl, substituted or unsubstituted indolyl, $(CH_2)_nOR^5$, $(CH_2)_nC(O)NR^6R^7$, or $(CH_2)_nSR^5$; and $R^{16}$, $R^{17}$, and $R^{18}$ are each independently hydrogen or $(C_1$-$C_6)$alkyl.

In another embodiment, the disclosure provides a compound of Formula I, wherein:

$L_1$ and $L_2$ are each independently —$(C_1$-$C_6)$alkyl-, —$O(C_1$-$C_6)$alkyl-, —$C(O)(C_1$-$C_6)$alkyl-, —$(CH_2)_nC(O)NH(C_1$-$C_6)$alkyl-, —$(C_2$-$C_6)$alkenyl-, —$O(C_2$-$C_6)$alkenyl-, —$C(O)(C_2$-$C_6)$alkenyl-, —$(CH_2)_nC(O)NH(C_2$-$C_6)$alkenyl-, wherein each alkyl and alkenyl group may be substituted with alkyl, alkoxy, or carboxyl;

n is an integer selected from 0, 1, 2, 3, 4, 5, and 6;

$R^8$, $R^{10}$, $R^{12}$, and $R^{14}$ are each independently H, $CH_3$, $CH_2OH$, $CH_2SH$, $CH(OH)CH_3$, $CH_2C(O)NH_2$, $CH_2CH_2C(O)NH_2$, $CH_2CH_2SCH_3$, $CH_2CH(CH_3)_2$, $CH(CH_3)CH_2CH_3$, $CH_2C_6C_5$

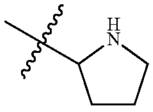

,

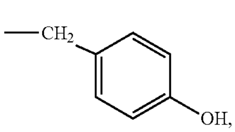

, or

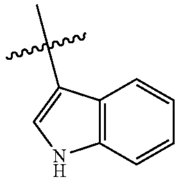

.

In another embodiment, the disclosure provides a compound of Formula I, wherein:

$L_1$ and $L_2$ are each independently —$OCH_2CH_2$—, —$CH_2C(O)$—, —$CH_2CH_2C(O)$—, —$C(O)NHCH_2CH_2$, —$CH_2CH{=}CHCH_2$—, —$OCH_2CH{=}CHCH_2CH_2$—, —$OCH_2CH{=}CHCH_2CH(CO_2H)$—, —$CH_2C(O)NHCH_2CH_2$—, or $CH_2CH(OCH_3){=}C(CH_3)CH_2CH_2$; and $R^8$, $R^{10}$, $R^{12}$, and $R^{14}$ are each independently the side-chain of the amino acid alanine, asparagine, cysteine, glutamine, glycine, isoleucine, leucine, methionine, phenylalanine, proline, serine, threonine, tryptophan, tyrosine, or valine.

In another embodiment, the disclosure provides a compound of Formula I, wherein the compound has Formulae II, III, IV, V, or VI:

(II)

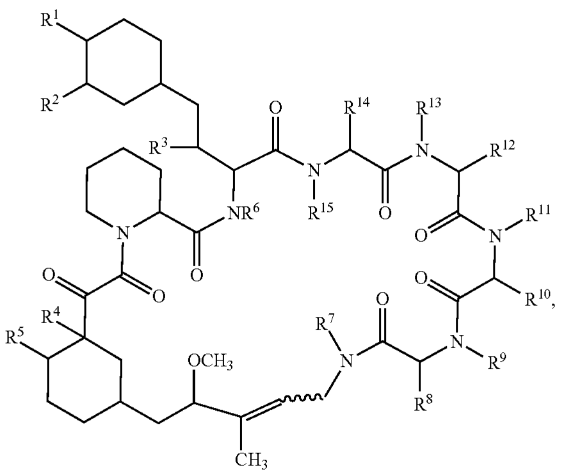

(III)

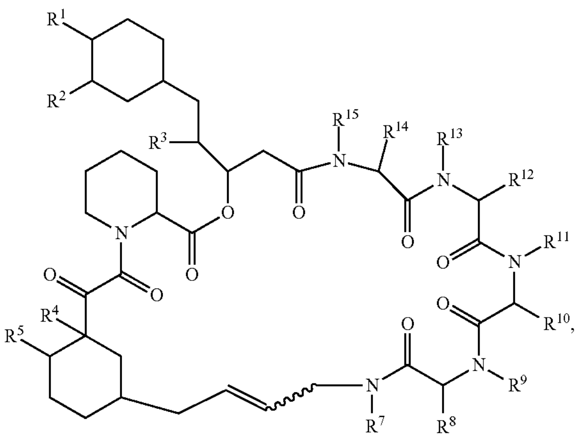

-continued (IV)

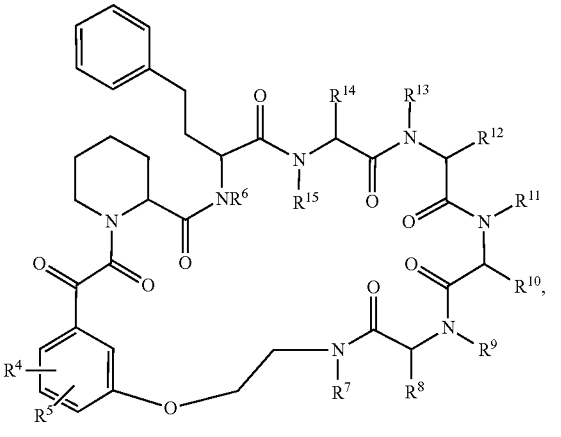

(V)

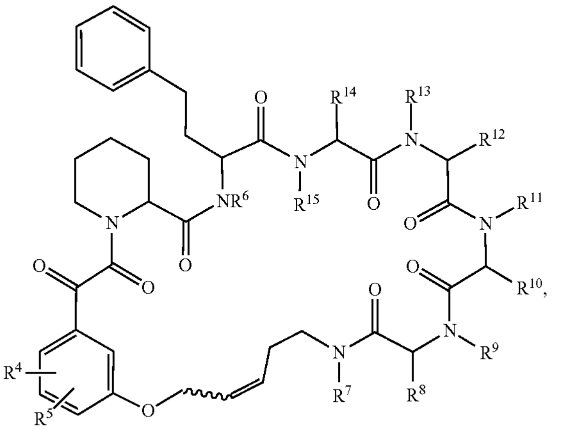

(VI)

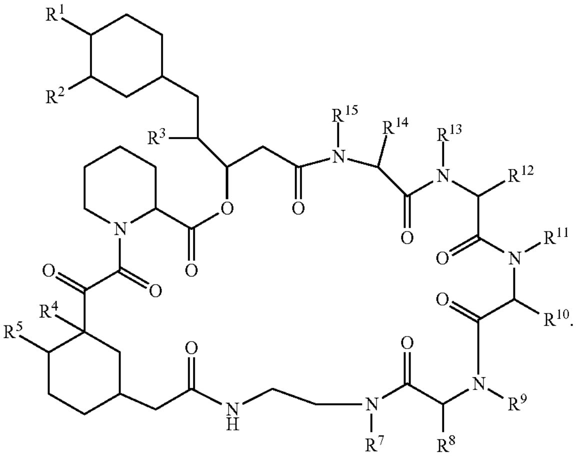

In another embodiment, the disclosure provides a compound of Formula I, wherein the compound has Formulae VII, VIII, IX, or X:
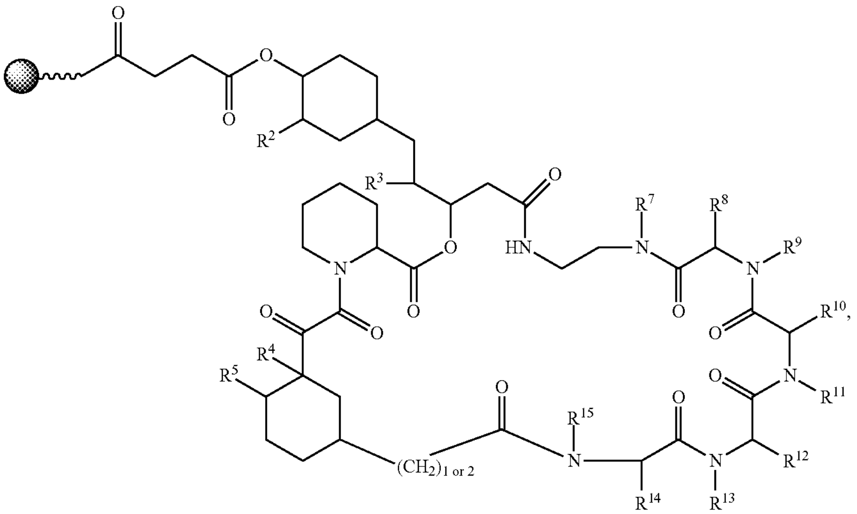
(VII)
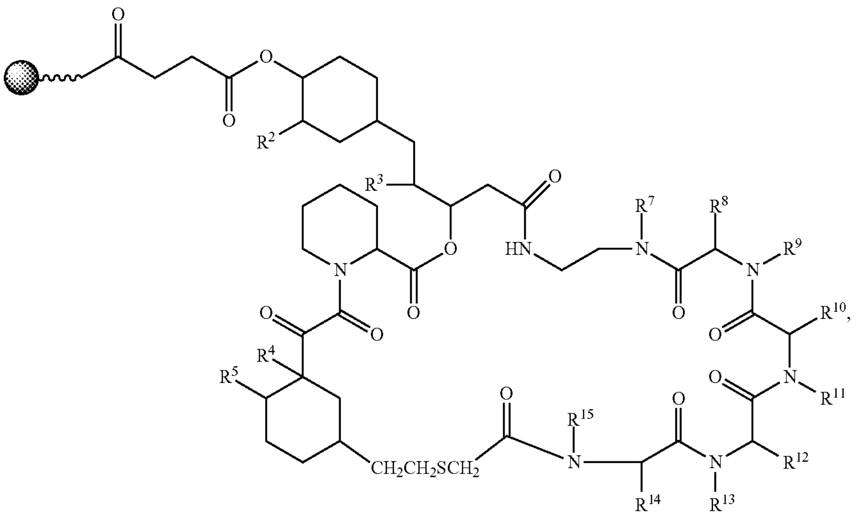
(VIII)

-continued
(IX)
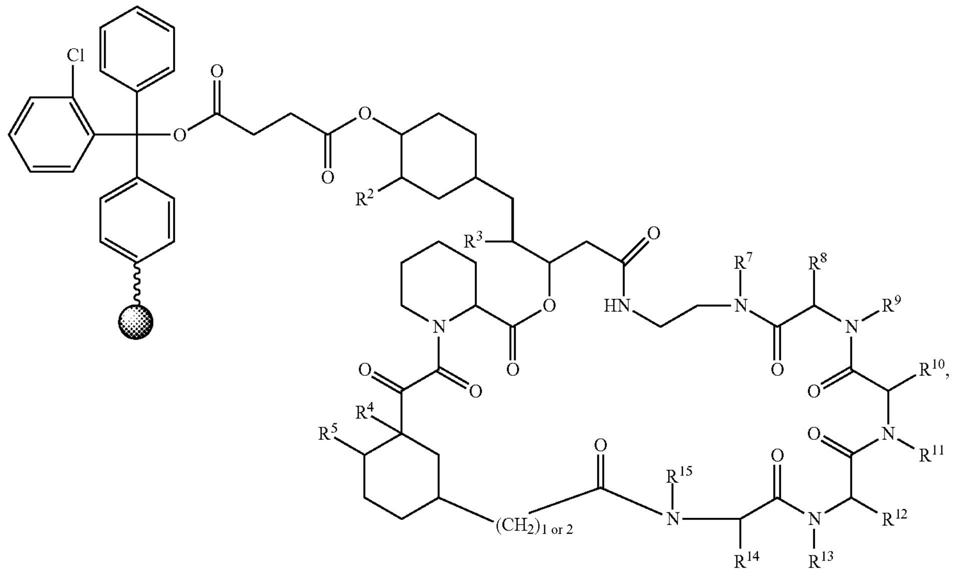
(X)
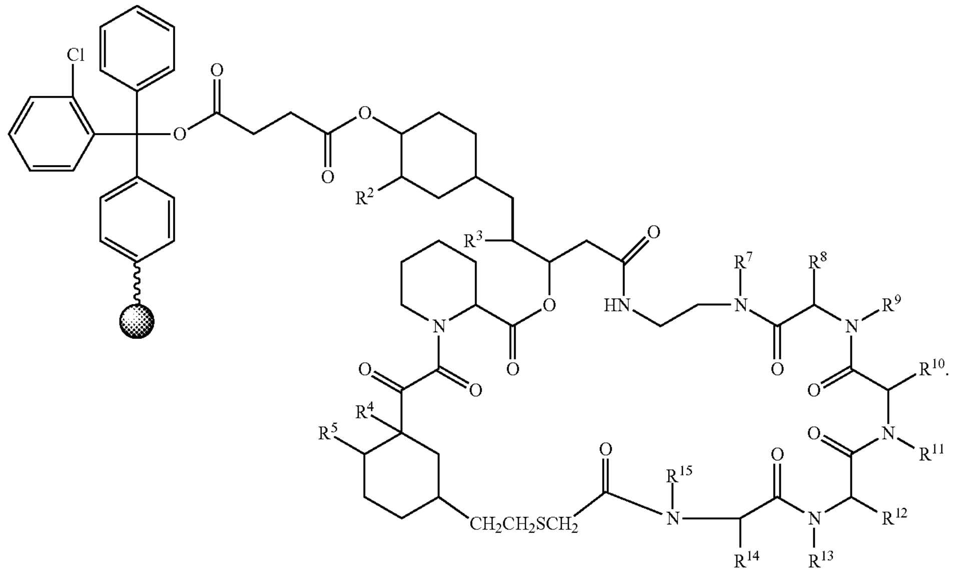

In another embodiment, the disclosure provides methods for treating cancer in a patient in need thereof by administering the compound of Formula I to the patient.

In another embodiment, the disclosure provides methods for suppressing the immune system in a patient in need thereof by administering the compound of Formula I to the patient.

In another embodiment, the disclosure provides methods for preparing a compound of Formula I:

(I)

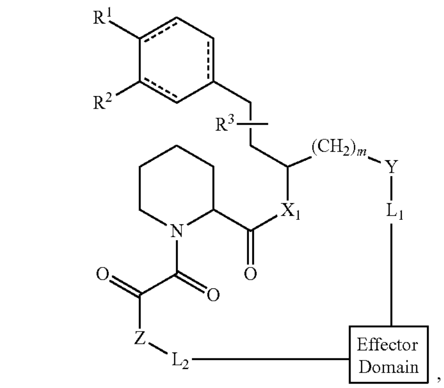

or a pharmaceutically acceptable salt or solvate thereof, wherein:

------- is a single or double bond;

$X_1$ is O or $NR^6$;

Y is —C(O)— or

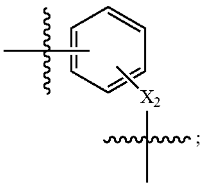

;

$X_2$ is $(CH_2)_m$, O, or $NR^6$;

Z is

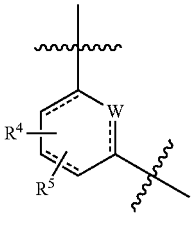

or

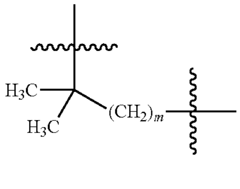

;

W is O, CH, $CH_2$, $CR^4$, or $CR^5$;

$L_1$ and $L_2$ are each independently a direct bond, substituted or unsubstituted —$(C_1$-$C_6)$alkyl-, substituted or unsubstituted —$(CH_2)_n$O$(C_1$-$C_6)$alkyl-, substituted or unsubstituted —$(CH_2)_n$C(O)—, substituted or unsubstituted —$(CH_2)_n$C(O)$(C_1$-$C_6)$alkyl-, substituted or unsubstituted —$(CH_2)_n$C(O)O$(C_1$-$C_6)$alkyl-, substituted or unsubstituted —$(CH_2)_n$NH$(C_1$-$C_6)$alkyl-, substituted or unsubstituted —$(CH_2)_n$C(O)NH$(C_1$-$C_6)$alkyl-, substituted or unsubstituted —$(CH_2)_n$S$(C_1$-$C_6)$alkyl-, substituted or unsubstituted —$(CH_2)_n$C(O)$(CH_2)_n$S$(C_1$-$C_6)$alkyl-, substituted or unsubstituted —$(C_2$-$C_6)$alkenyl-, substituted or unsubstituted —$(CH_2)_n$O$(C_2$-$C_6)$alkenyl-, substituted or unsubstituted —$(CH_2)_n$C(O)$(C_2$-$C_6)$alkenyl-, substituted or unsubstituted —$(CH_2)_n$C(O)O$(C_2$-$C_6)$alkenyl-, substituted or unsubstituted —$(CH_2)_n$NH$(C_1$-$C_6)$alkenyl-, substituted or unsubstituted —$(CH_2)_n$C(O)NH$(C_2$-$C_6)$alkenyl-, substituted or unsubstituted —$(CH_2)_n$S$(C_2$-$C_6)$alkenyl-, substituted or unsubstituted —$(CH_2)_n$C(O)$(CH_2)_n$S$(C_2$-$C_6)$alkenyl-, substituted or unsubstituted —$(C_2$-$C_6)$alkynyl-, substituted or unsubstituted —$(CH_2)_n$O$(C_2$-$C_6)$alkynyl-, substituted or unsubstituted —$(CH_2)_n$C(O)$(C_2$-$C_6)$alkynyl-, substituted or unsubstituted —$(CH_2)_n$C(O)O$(C_2$-$C_6)$alkynyl-, substituted or unsubstituted —$(CH_2)_n$NH$(C_1$-$C_6)$alkynyl-, substituted or unsubstituted —$(CH_2)_n$C(O)NH$(C_2$-$C_6)$alkynyl-, substituted or unsubstituted —$(CH_2)_n$S$(C_2$-$C_6)$alkynyl-, substituted or unsubstituted —$(CH_2)_n$C(O)$(CH_2)_n$S$(C_2$-$C_6)$alkynyl-, wherein each alkyl, alkenyl and alkynyl group may be optionally substituted with alkyl, alkoxy, amino, carboxyl, cyano, nitro, or trifluoromethyl;

each m is independently an integer selected from 0, 1, 2, 3, 4, 5, and 6;

each n is independently an integer selected from 0, 1, 2, 3, 4, 5, and 6;

$R^1$ is hydrogen, hydroxyl, or OPG, wherein PG is a protecting group, or $R^1$ is

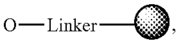

, wherein

is a resin;

$R^2$ is hydrogen, hydroxyl, or alkoxy;

$R^3$ is hydrogen or alkyl;

$R^4$ and $R^5$ are each independently hydrogen, hydroxy, alkyl, alkoxy, or OPG, wherein PG is a protecting group;

$R^6$ is hydrogen or alkyl;

wherein the Effector Domain has Formula II:

(II)

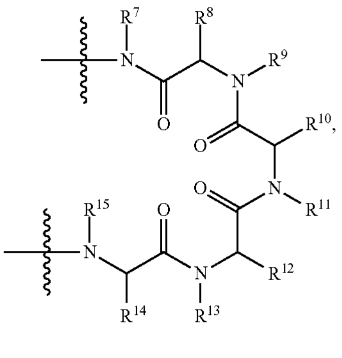

wherein:

$R^7$, $R^9$, $R^{10}$, $R^{13}$, and $R^{15}$ are each independently hydrogen or alkyl;

$R^8$, $R^{10}$, $R^{12}$, and $R^{14}$ are each independently hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$ $NR^{17}R^{18}$, $(CH_2)_nC(O)NR^{17}R^{18}$, $(CH_2)$ $N^{19}RC(O)R^{16}$, $(CH_2)_nN^{19}RC(O)OR^{16}$, $(CH_2)$ $NR^{19}C(O)NR^{17}R^{18}$, $(CH_2)_nSR^{16}$, $(CH_2)_nS(O)_jNR^{17}R^{18}$, $(CH_2)_nN^{19}RS(O)_jR^{16}$, or $—(CH_2)_nNR^{19}S(O)_jNR^{17}R^{18}$;

n is an integer selected from 0, 1, 2, 3, 4, 5, and 6;

j is an integer selected from 0, 1, and 2;

$R^{16}$, $R^{17}$, $R^{18}$, and $R^{19}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{16}$ and $R^{19}$ are as described above, and $R^{17}$ and $R^{18}$, together with the N atom to which they are attached, form a substituted or unsubstituted 5-, 6-, or 7-membered heterocycloalkyl or a substituted or unsubstituted 5-membered heteroaryl, wherein each of the above groups listed for $R^8$, $R^{10}$, $R^{12}$, and $R^{14}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$ $NR^{17}R^{18}$, $(CH_2)_nC(O)NR^{17}R^{18}$, $(CH_2)$ $N^{19}RC(O)R^{16}$, $(CH_2)$ $N^{19}RC(O)OR^{16}$, $(CH_2)$ $NR^{19}C(O)NR^{17}R^{18}$, $(CH_2)_nSR^{16}$, $(CH_2)_nS(O)_jNR^{17}R^{18}$, $(CH_2)$ $N^{19}RS(O)_jR^{16}$, and $—(CH_2)_nNR^{19}S(O)_jNR^{17}R^{18}$;

the method comprising the steps of: a) coupling and cyclizing a compound of Formula XI with the Effector Domain to provide the compound of Formula I:

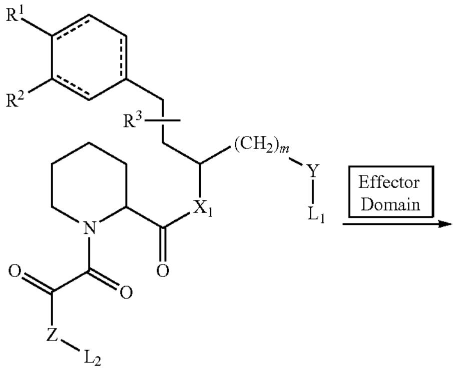

(XI)

-continued

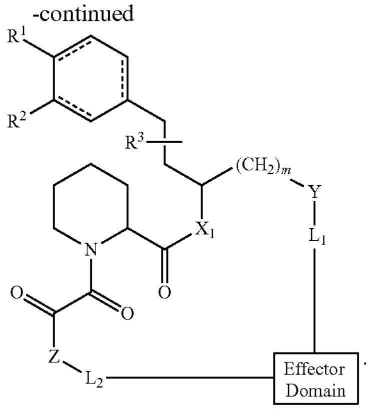

(I)

In another embodiment, the disclosure provides methods for preparing a compound of Formula I, wherein the reagents benzotriazol-1-yl-oxytripyrrolidinophosphonium hexafluorophosphate (PyBOP), N,N-diisopropylethylamine (DIPEA), and N-methylpyrrolidine (NIMP) are used in coupling.

In another embodiment, the disclosure provides methods for preparing a compound of Formula I, wherein the reagent benzylidene[1,3-bis(2,4,6-trimethylphenyl)-2-imidazolidinylidene]dichloro(tricyclohexylphosphine)ruthenium is used in cyclizing.

In another embodiment, the disclosure provides a compound of Formula I, prepared by the methods described herein.

In another embodiment, the disclosure provides methods for identifying compounds from a library of compounds that binds to a protein encoded in a genome in complex with FKBP, by:

a) screening a hybrid combinatorial peptide or non-peptide library of compounds that includes the FKBP-binding domain (FKBP) of the natural product rapamycin or FK506 against the proteins encoded in a genome using a protein chip;

b) detecting the binding of a compound to a protein on the chip using the anti-V5 antibody together with a fluorescently tagged secondary antibody;

c) recording the fluorescence pattern of the protein chip on a chip reader;

d) identifying the proteins based on the physical location of the fluorescent spots on the chip; and e) determining the function of the protein based on its perturbed biochemical and cellular functions.

In another embodiment, the disclosure provides methods for identifying compounds from a library of compounds that binds to a protein encoded in a genome in complex with FKBP, wherein the genome is the human genome; and the library of compounds has Formula I:

(I)

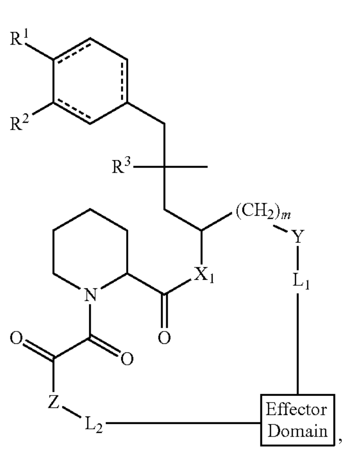

or a pharmaceutically acceptable salt or solvate thereof, wherein:

- - - - - - - is a single or double bond;

$X_1$ is O or $NR^6$;

Y is —C(O)— or

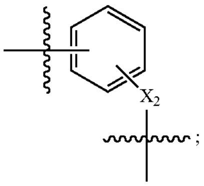

$X_2$ is $(CH_2)_m$, O, or $NR^6$;

Z is

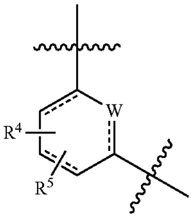

or

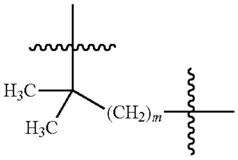

;

W is O, CH, $CH_2$, $CR^4$, or $CR^5$;

$L_1$ and $L_2$ are each independently a direct bond, substituted or unsubstituted —$(C_1$-$C_6)$alkyl-, substituted or unsubstituted —$(CH_2)_nO(C_1$-$C_6)$alkyl-, substituted or unsubstituted —$(CH_2)_nC(O)$—, substituted or unsubstituted —$(CH_2)_nC(O)(C_1$-$C_6)$alkyl-, substituted or unsubstituted —$(CH_2)_nC(O)O(C_1$-$C_6)$alkyl-, substituted or unsubstituted —$(CH_2)_nNH(C_1$-$C_6)$alkyl-, substituted or unsubstituted —$(CH_2)_nC(O)NH(C_1$-$C_6)$alkyl-, substituted or unsubstituted —$(CH_2)_nS(C_1$-$C_6)$alkyl-, substituted or unsubstituted —$(CH_2)_nC(O)(CH_2)_nS(C_1$-$C_6)$alkyl-, substituted or unsubstituted —$(C_2$-$C_6)$alkenyl-, substituted or unsubstituted —$(CH_2)_nO(C_2$-$C_6)$alkenyl-, substituted or unsubstituted —$(CH_2)_nC(O)(C_2$-$C_6)$alkenyl-, substituted or unsubstituted —$(CH_2)_nC(O)O(C_2$-$C_6)$alkenyl-, substituted or unsubstituted —$(CH_2)_nNH(C_1$-$C_6)$alkenyl-, substituted or unsubstituted —$(CH_2)_nC(O)NH(C_2$-$C_6)$alkenyl-, substituted or unsubstituted —$(CH_2)_nS(C_2$-$C_6)$alkenyl-, substituted or unsubstituted —$(CH_2)_nC(O)(CH_2)_nS(C_2$-$C_6)$alkenyl-, substituted or unsubstituted —$(C_2$-$C_6)$alkynyl-, substituted or unsubstituted —$(CH_2)_nO(C_2$-$C_6)$alkynyl-, substituted or unsubstituted —$(CH_2)_nC(O)(C_2$-$C_6)$alkynyl-, substituted or unsubstituted —$(CH_2)_nC(O)O(C_2$-$C_6)$alkynyl-, substituted or unsubstituted —$(CH_2)_nNH(C_1$-$C_6)$alkynyl-, substituted or unsubstituted —$(CH_2)_nC(O)NH(C_2$-$C_6)$alkynyl-, substituted or unsubstituted —$(CH_2)_nS(C_2$-$C_6)$alkynyl-, substituted or unsubstituted —$(CH_2)_nC(O)(CH_2)_nS(C_2$-$C_6)$alkynyl-, wherein each alkyl, alkenyl and alkynyl group may be optionally substituted with alkyl, alkoxy, amino, carboxyl, cyano, nitro, or trifluoromethyl;

each m is independently an integer selected from 0, 1, 2, 3, 4, 5, and 6;

each n is independently an integer selected from 0, 1, 2, 3, 4, 5, and 6;

$R^1$ is hydrogen, hydroxyl, or OPG, wherein PG is a protecting group, or $R^1$ is

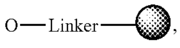

wherein

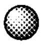

is a resin;

$R^2$ is hydrogen, hydroxyl, or alkoxy;

$R^3$ is hydrogen or alkyl;

$R^4$ and $R^5$ are each independently hydrogen, hydroxy, alkyl, alkoxy, or OPG, wherein PG is a protecting group;

$R^6$ is hydrogen or alkyl;

wherein the Effector Domain has Formula II:

(II)

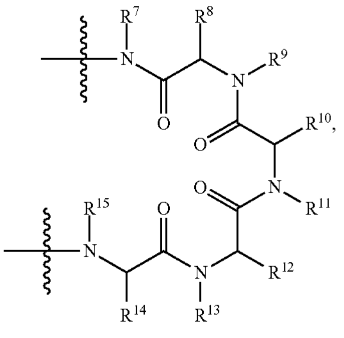

wherein:

$R^7$, $R^9$, $R^{10}$, $R^{13}$, and $R^{15}$ are each independently hydrogen or alkyl;

$R^8$, $R^{10}$, $R^{12}$, and $R^{14}$ are each independently hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)$, $N^{19}RC(O)R^{16}$, $(CH_2)_nN^{19}RC(O)OR^{16}$, $(CH_2)$, $NR^{19}C(O)NR^{17}R^{18}$, $(CH_2)_nSR^{16}$, $(CH_2)_nS(O)_jNR^{17}R^{18}$, $(CH_2)_nN^{19}RS(O)_jR^{16}$, or $-(CH_2)_nNR^{19}S(O)_jNR^{17}R^{18}$;

n is an integer selected from 0, 1, 2, 3, 4, 5, and 6;

j is an integer selected from 0, 1, and 2;

$R^{16}$, $R^{17}$, $R^{18}$, and $R^{19}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{16}$ and $R^{19}$ are as described above, and $R^{17}$ and $R^{18}$, together with the N atom to which they are attached, form a substituted or unsubstituted 5-, 6-, or 7-membered heterocycloalkyl or a substituted or unsubstituted 5-membered heteroaryl, wherein each of the above groups listed for $R^8$, $R^{10}$, $R^{12}$, and $R^{14}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)$, $N^{19}RC(O)R^{16}$, $(CH_2)$, $N^{19}RC(O)OR^{16}$, $(CH_2)$, $NR^{19}C(O)NR^{17}R^{18}$, $(CH_2)_nSR^{16}$, $(CH_2)_nS(O)_jNR^{17}R^{18}$, $(CH_2)$, $N^{19}RS(O)_jR^{16}$, and $-(CH_2)_nNR^{19}S(O)_jNR^{17}R^{18}$.

In another embodiment, the disclosure provides methods for determining the function of a protein encoded in a genome, wherein the compound of Formula I:

X is O or $NR^6$;

$L_1$ and $L_2$ are each independently $-(C_1\text{-}C_6)$alkyl-, $-(CH_2)_nO(C_1\text{-}C_6)$alkyl-, $-(CH_2)_nC(O)(C_1\text{-}C_6)$alkyl-, $-(CH_2)_nC(O)O(C_1\text{-}C_6)$alkyl-, $-(CH_2)_nNH(C_1\text{-}C_6)$alkyl-, $-(CH_2)_nC(O)NH(C_1\text{-}C_6)$alkyl-, $-(CH_2)_nS(C_1\text{-}C_6)$alkyl-, $-(CH_2)_nC(O)(CH_2)_nS(C_1\text{-}C_6)$alkyl-, $-(C_2\text{-}C_6)$alkenyl-, $-(CH_2)_nO(C_2\text{-}C_6)$alkenyl-, $-(CH_2)_nC(O)(C_2\text{-}C_6)$alkenyl-, $-(CH_2)_nC(O)O(C_2\text{-}C_6)$alkenyl-, $-(CH_2)_nNH(C_1\text{-}C_6)$alkenyl-, $-(CH_2)_nC(O)NH(C_2\text{-}C_6)$alkenyl-, $-(CH_2)_nS(C_2\text{-}C_6)$alkenyl-, $-(CH_2)_nC(O)(CH_2)_nS(C_2\text{-}C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl, or OPG, wherein PG is a silyl protecting group, or $R^1$ is

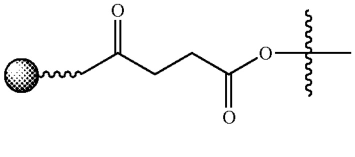

or

-continued

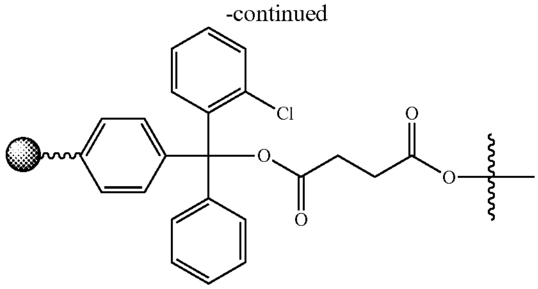

, wherein

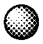

is a resin;

$R^2$ is hydroxyl or alkoxy;

$R^3$ is hydrogen or alkyl;

$R^4$ and $R^5$ are each independently hydrogen, alkyl, alkoxy, or OPG, wherein PG is a silyl protecting group;

$R^6$ is hydrogen;

$R^7$, $R^9$, $R^{10}$, $R^{13}$, and $R^{15}$ are each independently hydrogen or $CH_3$;

$R^8$, $R^{10}$, $R^{12}$, and $R^{14}$ are each independently substituted or unsubstituted cyclopropyl, substituted or unsubstituted cyclobutyl, substituted or unsubstituted cyclopentyl, substituted or unsubstituted cyclohexyl, substituted or unsubstituted cycloheptyl, or substituted or unsubstituted cyclooctyl; or $R^8$, $R^{10}$, $R^{12}$, and $R^{14}$ are each independently substituted or unsubstituted tetrahydrofuranyl, substituted or unsubstituted tetrahydrothiophenyl, substituted or unsubstituted pyrrolidinyl, substituted or unsubstituted 1,3-dioxolanyl, substituted or unsubstituted pyrazolidinyl, substituted or unsubstituted imidazolidinyl, substituted or unsubstituted 1,4-dioxanyl, substituted or unsubstituted piperidinyl, substituted or unsubstituted piperazinyl, substituted or unsubstituted morpholinyl, substituted or unsubstituted thiomorpholinyl, or substituted or unsubstituted 1,4-dithianyl; or $R^8$, $R^{10}$, $R^{12}$, and $R^{14}$ are each independently substituted or unsubstituted phenyl, substituted or unsubstituted benzyl, substituted or unsubstituted naphthylenyl, or substituted or unsubstituted biphenyl; or $R^8$, $R^{10}$, $R^{12}$, and $R^{14}$ are each independently substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted triazolyl, substituted or unsubstituted isoxazolyl, substituted or unsubstituted oxazolyl, substituted or unsubstituted thiazolyl, substituted or unsubstituted isothiazolyl, substituted or unsubstituted pyridinyl, substituted or unsubstituted pyridizanyl, substituted or unsubstituted pyrimidinyl, substituted or unsubstituted triazinyl, substituted or unsubstituted benzofuranyl, substituted or unsubstituted benzo(b)thiophenyl, substituted or unsubstituted indolyl, substituted or unsubstituted benzimidazolyl, substituted or unsubstituted indazolyl, substituted or unsubstituted benzisoxazolyl, substituted or unsubstituted benzoxazolyl, substituted or unsubstituted benzothiazolyl, substituted or unsubstituted quinolinyl, substituted or unsubstituted isoquinolinyl, substituted or unsubstituted quinazolinyl, substituted or unsubstituted quinoxalinyl, or substituted or unsubstituted naphthyridinyl.

In another embodiment, the disclosure provides methods for identifying compounds from a library of compounds that binds to a protein encoded in a genome in complex with FKBP, wherein the compound of Formula I:

$L_1$ and $L_2$ are each independently —$(C_1$-$C_6)$alkyl-, —$(CH_2)_n O(C_1$-$C_6)$alkyl-, —$(CH_2)_n C(O)(C_1$-$C_6)$alkyl-, —$(CH_2)_n NH(C_1$-$C_6)$alkyl-, —$(CH_2)_n C(O)NH(C_1$-$C_6)$alkyl-, —$(C_2$-$C_6)$alkenyl-, —$(CH_2)_n O(C_2$-$C_6)$alkenyl-, —$(CH_2)_n C(O)(C_2$-$C_6)$alkenyl-, —$(CH_2)_n NH(C_1$-$C_6)$alkenyl-, —$(CH_2)_n C(O)NH(C_2$-$C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl or OPG, wherein PG is a tert-butyldimethylsilyl protecting group, or $R^1$ is

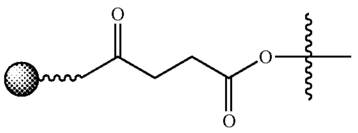

or

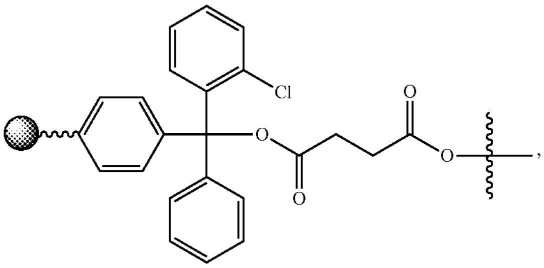

, wherein

is Wang resin;

$R^4$ and $R^5$ are each independently hydrogen, hydroxy, alkyl, alkoxy, or OPG, wherein PG is a tert-butyldimethylsilyl protecting group;

$R^7$, $R^9$, $R^{11}$, $R^{13}$, and $R^{15}$ are each independently hydrogen;

$R^8$, $R^{10}$, $R^{12}$, and $R^{14}$ are each independently hydrogen, substituted or unsubstituted alkyl, substituted or unsubstituted benzyl, substituted or unsubstituted pyrrolidinyl, substituted or unsubstituted indolyl, $(CH_2)_n OR^5$, $(CH_2)_n C(O)NR^6R^7$, or $(CH_2)_n SR^5$; and $R^{16}$, $R^{17}$, and $R^{18}$ are each independently hydrogen or $(C_1$-$C_6)$alkyl.

In another embodiment, the disclosure provides methods for identifying compounds from a library of compounds that binds to a protein encoded in a genome in complex with FKBP, wherein the compound of Formula I:

$L_1$ and $L_2$ are each independently —$(C_1$-$C_6)$alkyl-, —$O(C_1$-$C_6)$alkyl-, —$C(O)(C_1$-$C_6)$alkyl-, —$(CH_2)_n C(O)NH(C_1$-$C_6)$alkyl-, —$(C_2$-$C_6)$alkenyl-, —$O(C_2$-$C_6)$alkenyl-, —$C(O)(C_2$-$C_6)$alkenyl-, —$(CH_2)_n C(O)NH(C_2$-$C_6)$alkenyl-, wherein each alkyl and alkenyl group may be substituted with alkyl, alkoxy, or carboxyl;

n is an integer selected from 0, 1, 2, 3, 4, 5, and 6;

$R^8$, $R^{10}$, $R^{12}$, and $R^{14}$ are each independently H, $CH_3$, $CH_2OH$, $CH_2SH$, $CH(OH)CH_3$, $CH_2C(O)NH_2$, $CH_2CH_2C(O)NH_2$, $CH_2CH_2SCH_3$, $CH_2CH(CH_3)_2$, $CH(CH_3)CH_2CH_3$, $CH_2C_6C_5$,

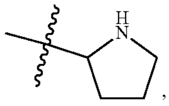

,

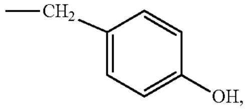

or

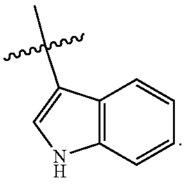

.

In another embodiment, the disclosure provides methods for identifying compounds from a library of compounds that binds to a protein encoded in a genome in complex with FKBP, wherein the compound of Formula I:

$L_1$ and $L_2$ are each independently —$OCH_2CH_2$—, —$CH_2C(O)$—, —$CH_2CH_2C(O)$—, —$C(O)NHCH_2CH_2$, —$CH_2CH{=}CHCH_2$—, —$OCH_2CH{=}CHCH_2CH_2$—, —$OCH_2CH{=}CHCH_2CH(CO_2H)$—, —$CH_2C(O)NHCH_2CH_2$—, or $CH_2CH(OCH_3){=}C(CH_3)CH_2CH_2$; and $R^8$, $R^{10}$, $R^{12}$, and $R^{14}$ are each independently the side-chain of the amino acid alanine, asparagine, cysteine, glutamine, glycine, isoleucine, leucine, methionine, phenylalanine, proline, serine, threonine, tryptophan, tyrosine, or valine.

In another embodiment, the disclosure provides methods for generating a lead compound as a high-affinity ligand of the FKBP isoforms, the method comprising the steps of:

a) screening a hybrid combinatorial peptide or non-peptide library of compounds that includes the FKBP-binding domain (FKBP) of the natural product rapamycin or FK506 against the proteins encoded in a genome using a protein chip;

b) detecting the binding of a compound to a protein on the chip using the anti-V5 antibody together with a fluorescently tagged secondary antibody;

c) recording the fluorescence pattern of the protein chip on a chip reader;

d) identifying the proteins based on the physical location of the fluorescent spots on the chip; and e) determining the structure of the lead compound.

In another embodiment, the disclosure provides methods for generating a lead compound as a high-affinity ligand of the FKBP isoforms, wherein the genome is the human genome; and the library of compounds has Formula I:

(I)

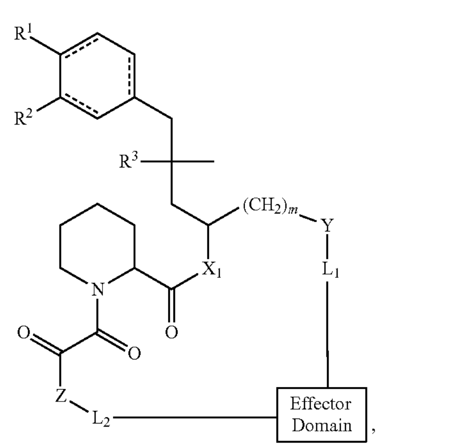

or a pharmaceutically acceptable salt or solvate thereof, wherein:

------- is a single or double bond;

$X_1$ is O or $NR^6$;

Y is —C(O)— or

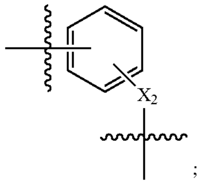

;

$X_2$ is $(CH_2)_m$, O, or $NR^6$;

Z is

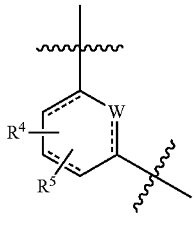

or

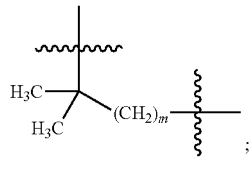

;

W is O, CH, $CH_2$, $CR^4$, or $CR^5$;

$L_1$ and $L_2$ are each independently a direct bond, substituted or unsubstituted —$(C_1\text{-}C_6)$alkyl-, substituted or unsubstituted —$(CH_2)_nO(C_1\text{-}C_6)$alkyl-, substituted or unsubstituted —$(CH_2)_nC(O)$—, substituted or unsubstituted —$(CH_2)_nC(O)(C_1\text{-}C_6)$alkyl-, substituted or unsubstituted —$(CH_2)_nC(O)O(C_1\text{-}C_6)$alkyl-, substituted or unsubstituted —$(CH_2)_nNH(C_1\text{-}C_6)$alkyl-, substituted or unsubstituted —$(CH_2)_nC(O)NH(C_1\text{-}C_6)$alkyl-, substituted or unsubstituted —$(CH_2)_nS(C_1\text{-}C_6)$alkyl-, substituted or unsubstituted —$(CH_2)_nC(O)(CH_2)_nS(C_1\text{-}C_6)$alkyl-, substituted or unsubstituted —$(C_2\text{-}C_6)$alkenyl-, substituted or unsubstituted —$(CH_2)_nO(C_2\text{-}C_6)$alkenyl-, substituted or unsubstituted —$(CH_2)_nC(O)(C_2\text{-}C_6)$alkenyl-, substituted or unsubstituted —$(CH_2)_nC(O)O(C_2\text{-}C_6)$alkenyl-, substituted or unsubstituted —$(CH_2)_nNH(C_1\text{-}C_6)$alkenyl-, substituted or unsubstituted —$(CH_2)_nC(O)NH(C_2\text{-}C_6)$alkenyl-, substituted or unsubstituted —$(CH_2)_nS(C_2\text{-}C_6)$alkenyl-, substituted or unsubstituted —$(CH_2)_nC(O)(CH_2)_nS(C_2\text{-}C_6)$alkenyl-, substituted or unsubstituted —$(C_2\text{-}C_6)$alkynyl-, substituted or unsubstituted —$(CH_2)_nO(C_2\text{-}C_6)$alkynyl-, substituted or unsubstituted —$(CH_2)_nC(O)(C_2\text{-}C_6)$alkynyl-, substituted or unsubstituted —$(CH_2)_nC(O)O(C_2\text{-}C_6)$alkynyl-, substituted or unsubstituted —$(CH_2)_nNH(C_1\text{-}C_6)$alkynyl-, substituted or unsubstituted —$(CH_2)_nC(O)NH(C_2\text{-}C_6)$alkynyl-, substituted or unsubstituted —$(CH_2)_nS(C_2\text{-}C_6)$alkynyl-, substituted or unsubstituted —$(CH_2)_nC(O)(CH_2)_nS(C_2\text{-}C_6)$alkynyl-, wherein each alkyl, alkenyl and alkynyl group may be optionally substituted with alkyl, alkoxy, amino, carboxyl, cyano, nitro, or trifluoromethyl;

each m is independently an integer selected from 0, 1, 2, 3, 4, 5, and 6;

each n is independently an integer selected from 0, 1, 2, 3, 4, 5, and 6;

$R^1$ is hydrogen, hydroxyl, or OPG, wherein PG is a protecting group, or $R^1$ is

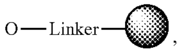

, wherein

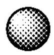

is a resin;

$R^2$ is hydrogen, hydroxyl, or alkoxy;

$R^3$ is hydrogen or alkyl;

$R^4$ and $R^5$ are each independently hydrogen, hydroxy, alkyl, alkoxy, or OPG, wherein PG is a protecting group;

$R^6$ is hydrogen or alkyl;

wherein the Effector Domain has Formula II:

(II)

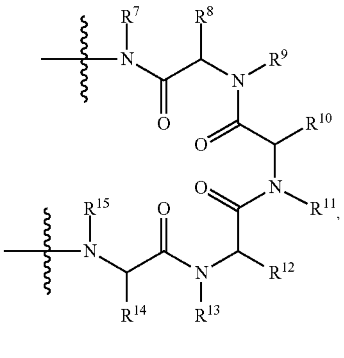

, wherein:

$R^7$, $R^9$, $R^{11}$, $R^{13}$, and $R^{15}$ are each independently hydrogen or alkyl;

$R^8$, $R^{10}$, $R^{12}$, and $R^{14}$ are each independently hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)$, $N^{19}RC(O)R^{16}$, $(CH_2)_nN^{19}RC(O)OR^{16}$, $(CH_2)$, $NR^{19}C(O)NR^{17}R^{18}$, $(CH_2)_nSR^{16}$, $(CH_2)_nS(O)_jNR^{17}R^{18}$, $(CH_2)$, $N^{19}RS(O)_jR^{16}$, or $—(CH_2)_nNR^{19}S(O)_jNR^{17}R^{18}$;

n is an integer selected from 0, 1, 2, 3, 4, 5, and 6;

j is an integer selected from 0, 1, and 2;

$R^{16}$, $R^{17}$, $R^{18}$, and $R^{19}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{16}$ and $R^{19}$ are as described above, and $R^{17}$ and $R^{18}$, together with the N atom to which they are attached, form a substituted or unsubstituted 5-, 6-, or 7-membered heterocycloalkyl or a substituted or unsubstituted 5-membered heteroaryl, wherein each of the above groups listed for R', $R^{10}$, $R^{12}$, and $R^{14}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)$, $NR^{17}R^{18}$, $(CH_2)_nC(O)NR^{17}R^{18}$, $(CH_2)$, $N^{19}RC(O)R^{16}$, $(CH_2)_nN^{19}RC(O)OR^{16}$, $(CH_2)_nNR^{19}C(O)NR^{17}R^{18}$, $(CH_2)_nSR^{16}$, $(CH_2)_nS(O)_jNR^{17}R^{18}$, $(CH_2)$, $N^{19}RS(O)_jR^{16}$, and $—(CH_2)_nNR^{19}S(O)_jNR^{17}R^{18}$.

In another embodiment, the disclosure provides methods for generating a lead compound as a high-affinity ligand of the FKBP isoforms, wherein the compound of Formula I:

X is O or $NR^6$;

$L_1$ and $L_2$ are each independently $—(C_1\text{-}C_6)$alkyl-, $—(CH_2)_nO(C_1\text{-}C_6)$alkyl-, $—(CH_2)_nC(O)(C_1\text{-}C_6)$alkyl-, $—(CH_2)_nC(O)O(C_1\text{-}C_6)$alkyl-, $—(CH_2)_nNH(C_1\text{-}C_6)$alkyl-, $—(CH_2)_nC(O)NH(C_1\text{-}C_6)$alkyl-, $—(CH_2)_nS(C_1\text{-}C_6)$alkyl-, $—(CH_2)_nC(O)(CH_2)_nS(C_1\text{-}C_6)$alkyl-, $—(C_2\text{-}C_6)$alkenyl-, $—(CH_2)_nO(C_2\text{-}C_6)$alkenyl-, $—(CH_2)_nC(O)(C_2\text{-}C_6)$alkenyl-, $—(CH_2)_nC(O)O(C_2\text{-}C_6)$alkenyl-, $—(CH_2)$, $NH(C_1\text{-}C_6)$alkenyl-, $—(CH_2)_nC(O)NH(C_2\text{-}C_6)$alkenyl-, $—(CH_2)_nS(C_2\text{-}C_6)$alkenyl-, $—(CH_2)_nC(O)(CH_2)_nS(C_2\text{-}C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl, or OPG, wherein PG is a silyl protecting group, or $R^1$ is

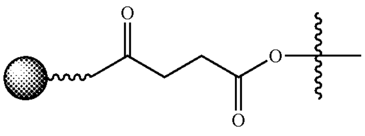

or

-continued

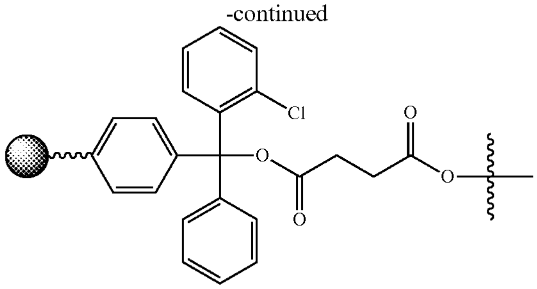

, wherein

is a resin;

$R^2$ is hydroxyl or alkoxy;

$R^3$ is hydrogen or alkyl;

$R^4$ and $R^5$ are each independently hydrogen, alkyl, alkoxy, or OPG, wherein PG is a silyl protecting group;

$R^6$ is hydrogen;

$R^7$, $R^9$, $R^{11}$, $R^{13}$, and $R^{15}$ are each independently hydrogen or $CH_3$;

$R^8$, $R^{10}$, $R^{12}$, and $R^{14}$ are each independently substituted or unsubstituted cyclopropyl, substituted or unsubstituted cyclobutyl, substituted or unsubstituted cyclopentyl, substituted or unsubstituted cyclohexyl, substituted or unsubstituted cycloheptyl, or substituted or unsubstituted cyclooctyl; or $R^8$, $R^{10}$, $R^{12}$, and $R^{14}$ are each independently substituted or unsubstituted tetrahydrofuranyl, substituted or unsubstituted tetrahydrothiophenyl, substituted or unsubstituted pyrrolidinyl, substituted or unsubstituted 1,3-dioxolanyl, substituted or unsubstituted pyrazolidinyl, substituted or unsubstituted imidazolidinyl, substituted or unsubstituted 1,4-dioxanyl, substituted or unsubstituted piperidinyl, substituted or unsubstituted piperazinyl, substituted or unsubstituted morpholinyl, substituted or unsubstituted thiomorpholinyl, or substituted or unsubstituted 1,4-dithianyl; or $R^8$, $R^{10}$, $R^{12}$, and $R^{14}$ are each independently substituted or unsubstituted phenyl, substituted or unsubstituted benzyl, substituted or unsubstituted naphthylenyl, or substituted or unsubstituted biphenyl; or $R^8$, $R^{10}$, $R^{12}$, and $R^{14}$ are each independently substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted triazolyl, substituted or unsubstituted isoxazolyl, substituted or unsubstituted oxazolyl, substituted or unsubstituted thiazolyl, substituted or unsubstituted isothiazolyl, substituted or unsubstituted pyridinyl, substituted or unsubstituted pyridizanyl, substituted or unsubstituted pyrimidinyl, substituted or unsubstituted triazinyl, substituted or unsubstituted benzofuranyl, substituted or unsubstituted benzo(b)thiophenyl, substituted or unsubstituted indolyl, substituted or unsubstituted benzimidazolyl, substituted or unsubstituted indazolyl, substituted or unsubstituted benzisoxazolyl, substituted or unsubstituted benzoxazolyl, substituted or unsubstituted benzothiazolyl, substituted or unsubstituted quinolinyl, substituted or unsubstituted isoquinolinyl, substituted or unsubstituted quinazolinyl, substituted or unsubstituted quinoxalinyl, or substituted or unsubstituted naphthyridinyl.

In another embodiment, the disclosure provides methods for generating a lead compound as a high-affinity ligand of the FKBP isoforms, wherein the compound of Formula I:

$L_1$ and $L_2$ are each independently —$(C_1$-$C_6)$alkyl-, —$(CH_2)_n$O$(C_1$-$C_6)$alkyl-, —$(CH_2)_n$C(O)$(C_1$-$C_6)$alkyl-, —$(CH_2)_n$NH$(C_1$-$C_6)$alkyl-, —$(CH_2)_n$C(O)NH$(C_1$-$C_6)$alkyl-, —$(C_2$—$C_6)$alkenyl-, —$(CH_2)_n$O$(C_2$-$C_6)$alkenyl-, —$(CH_2)_n$C(O)$(C_2$-$C_6)$alkenyl-, —$(CH_2)_n$NH$(C_1$-$C_6)$alkenyl-, —$(CH_2)_n$C(O)NH$(C_2$-$C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl or OPG, wherein PG is a tert-butyldimethylsilyl protecting group, or $R^1$ is

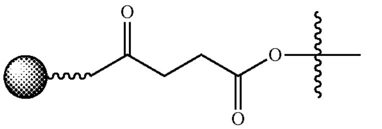

or

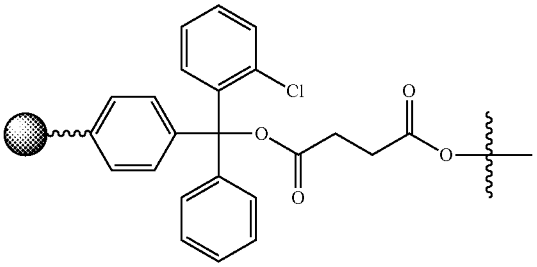

, wherein

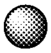

is Wang resin;

$R^4$ and $R^5$ are each independently hydrogen, hydroxy, alkyl, alkoxy, or OPG, wherein PG is a tert-butyldimethylsilyl protecting group;

$R^7$, $R^9$, $R^{11}$, $R^{13}$, and $R^{15}$ are each independently hydrogen;

$R^8$, $R^{10}$, $R^{12}$, and $R^{14}$ are each independently hydrogen, substituted or unsubstituted alkyl, substituted or unsubstituted benzyl, substituted or unsubstituted pyrrolidinyl, substituted or unsubstituted indolyl, $(CH_2)_n$OR$^5$, $(CH_2)_n$C(O)NR$^6$R$^7$, or $(CH_2)_n$SR$^5$; and $R^{16}$, $R^{17}$, and $R^{18}$ are each independently hydrogen or $(C_1$-$C_6)$alkyl.

In another embodiment, the disclosure provides methods for generating a lead compound as a high-affinity ligand of the FKBP isoforms, wherein the compound of Formula I:

$L_1$ and $L_2$ are each independently —$(C_1$-$C_6)$alkyl-, —O$(C_1$-$C_6)$alkyl-, —C(O)$(C_1$-$C_6)$alkyl-, —$(CH_2)_n$C(O)NH$(C_1$-$C_6)$alkyl-, —$(C_2$-$C_6)$alkenyl-, —O$(C_2$-$C_6)$alkenyl-, —C(O)$(C_2$—$C_6)$alkenyl-, —$(CH_2)_n$C(O)NH$(C_2$-$C_6)$alkenyl-, wherein each alkyl and alkenyl group may be substituted with alkyl, alkoxy, or carboxyl;

n is an integer selected from 0, 1, 2, 3, 4, 5, and 6;

$R^8$, $R^{10}$, $R^{12}$, and $R^{14}$ are each independently H, $CH_3$, $CH_2OH$, $CH_2SH$, $CH(OH)CH_3$, $CH_2C(O)NH_2$, $CH_2CH_2C(O)NH_2$, $CH_2CH_2SCH_3$, $CH_2CH(CH_3)_2$, $CH(CH_3)CH_2CH_3$, $CH_2C_6C_5$,

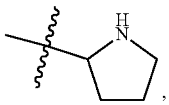

,

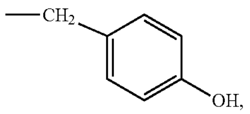

, or

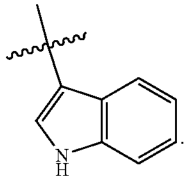

.

In another embodiment, the disclosure provides methods for generating a lead compound as a high-affinity ligand of the FKBP isoforms, wherein the compound of Formula I:

$L_1$ and $L_2$ are each independently —$OCH_2CH_2$—, —$CH_2C(O)$—, —$CH_2CH_2C(O)$—, —C(O)$NHCH_2CH_2$, —$CH_2CH$=$CHCH_2$—, —$OCH_2CH$=$CHCH_2CH_2$—, —$OCH_2CH$=$CHCH_2CH(CO_2H)$—, —$CH_2C(O)NHCH_2CH_2$—, or $CH_2CH(OCH_3)$=$C(CH_3)CH_2CH_2$; and $R^8$, $R^{10}$, $R^{12}$, and $R^{14}$ are each independently the side-chain of the amino acid alanine, asparagine, cysteine, glutamine, glycine, isoleucine, leucine, methionine, phenylalanine, proline, serine, threonine, tryptophan, tyrosine, or valine.

In another embodiment, the disclosure provides pharmaceutical compositions including the compound of Formula I and a pharmaceutically acceptable vehicle.

The present invention is based on the finding that the FKBP-binding domain (FKBP) of the immunophilin ligand family of macrolide natural products provides a scaffold for combinatorial peptide and non-peptide libraries and also acts as an embedded universal tag for each compound in the library. In particular, the FKBP-binding domain (FKBD) of the natural product rapamycin can serve both as a scaffold to present combinatorial peptide and non-peptide libraries and as an embedded universal tag for each compound in the library. Such hybrid combinatorial libraries are amenable to proteome-wide screening using protein chips by exploiting the presence of FKBD, which binds to and can be detected with a fluorescently labeled antibody against a tagged FKBP. In addition, FKBD can also confer stability and cell permeability to the fused ligands, increasing the probability that hits from such hybrid combinatorial libraries are readily applicable to study the cellular functions of the relevant target proteins. This work has lead to a new structural class of ligands that can be used as probes of protein functions.

The immunophilin ligand family consists of three members, cyclosporine A (CsA), FK506 and rapamycin, all of which are natural products with potent immunosuppressive or anticancer activities. Unlike other bioactive small molecules, these natural products have an unprecedented and extraordinary mode of action-through induction of dimeric ternary complexes between two distinct proteins: FKBP and their respective protein targets. They each bind to abundant and small cytosolic immunophilins, which also possess peptidyl prolyl cis-trans isomerase activity and are implicated in protein folding. Thus, CsA binds the cyclophilin (CyP) family of immunophilins; and FK506 and rapamycin both bind FKBP. The formation of the immunophilin-drug complexes per se does not have significant cellular consequences. It is the subsequent binding of these complexes to their respective target proteins that leads to inhibition of T cell activation or tumor cell growth. In the case of CsA and FK506, the CyP-CsA and FKBP-FK506 complexes bind to and inhibit the enzymatic activity of the protein phosphatase calcineurin. In the case of rapamycin, the FKBP-rapamycin complex binds to the PI3 kinase homologue known as the Target of Rapamycin (TOR, also known as FKBP-rapamycin associated protein/FRAP and rapamycin and FKBP12 target/RAFT).

The crystal structures of the FKBP-FK506-calcineurin and FKBP-rapamycin-TOR complexes revealed that both FK506 and rapamycin can be divided into two functional domains, the "FKBP-binding domain" (FKBD) and the "effector" domain, which mediate their interactions with calcineurin and TOR, respectively (FIG. 1). While there are extensive protein-protein interactions between FKBP and calcinerin in their ternary complex, there are far fewer interactions between FKBP and TOR, suggesting that the key role of FKBP in the inhibition of TOR by rapamycin is to bind to FKBD of the drug and present its effector domain to TOR.

A comparison of the structures of FK506 and rapamycin reveal that they share a nearly identical FKBD but each possesses a distinct effector domain. By swapping the effector domain of FK506 with that of rapamycin, it is possible to change the target from calcineurin to TOR, which bears no sequence, functional or structural similarities to each other. In addition, other proteins may be targeted by grafting new structures onto the FKBD of FK506 and rapamycin. Thus, the generation of new compounds with new target specificity may be achieved by grafting a sufficiently large combinatorial library onto FKBD in conjunction with proteome-wide screens through which each compound in the library is tested against every protein in the human proteome.

In addition, Rapamycin and FK506 are immunosuppressant macrocyclic drugs that are used to prevent immunorejection in organ transplantation, especially in kidney transplants. Rapamycin was first discovered as a product of the bacterium *Streptomyces hygroscopicus* in a soil sample from Easter Island. Rapamycin was originally developed as an antifungal agent but later was found to have both potent immunosuppressive and antiproliferative properties and may be useful in the treatment of certain cancers. FK506 is also an immunosuppressive drug that is mainly used after allogeneic organ transplant to reduce the activity of the patient's immune system and lower the risk of organ rejection. It is also used in a topical preparation in the treatment of atopic dermatitis (eczema), severe refractory uveitis after bone marrow transplants, exacerbations of minimal change disease, and the skin condition vitiligo. FK506 is a 23-membered macrolide lactone discovered in 1984 from the fermentation broth of a Japanese soil sample that contained the bacteria *Streptomyces tsukubaensis*. It reduces interleukin-2 (IL-2) production by T-cells.

Thus, in some embodiments, the compounds of Formula I may be useful as an immunosuppressive agent. These compounds may be delivered to a recipient, prior to, simultaneous with, and/or after transplantation. In particular, the compound of Formula I may be administered to cause an immunosuppressive effect in a subject, such that the transplanted cells are not rejected by that subject's immune system. Typically, the immunosuppressive agent of Formula I may be administered continuously through-out the transplant treatment typically over a period of days or weeks; for example, treatment may range from about 2 to about 20 days at a dosage range of about 5 to 40 mg per kilogram of body weight per day. The compound of Formula I may be administered by a variety of means, including parenteral, subcutaneous, intrapulmonary, oral, intranasal administration and the like. Preferably, dosing is given by oral administration.

Rapamycin and its derivatives including the compound of Formula I, are promising therapeutic agents with both immunosuppressant and anti-tumor properties. These actions are mediated through the specific inhibition of the mTOR protein kinase. mTOR serves as part of an evolutionarily conserved signaling pathway that controls the cell cycle in response to changing nutrient levels. The mTOR signaling network contains a number of tumor suppressor genes including PTEN, LKB1, TSC1, and TSC2, and a number of proto-oncogenes including PI3K, Akt, and eIF4E, and mTOR signaling is constitutively activated in many tumor types. These observations point to mTOR as an ideal target for anti-cancer agents including rapamycin and the compounds of Formula I. Rapamycin derivatives including the compounds of Formula I, may have efficacy as anti-tumor agents both alone, and when combined with other modes of therapy. These compounds inhibit tumor growth by halting tumor cell proliferation, inducing tumor cell apoptosis, and suppressing tumor angiogenesis. The immunosuppressant actions result from the inhibition of T and B cell proliferation through the same mechanisms that rapamycin blocks cancer cell proliferation. Thus, in addition to immunosuppression, rapamycin derivatives including the compounds of Formula I may act as anti-cancer agents.

The compounds of Formula I may be useful in the treatment of hyperproliferative disorders, for example cancer, including melanoma and other cancers of the skin, breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, and ovarian cancer, neurodegeneration, cardiac hypertrophy, pain, migraine, neurotraumatic diseases, stroke, diabetes, hepatomegaly, cardiovascular disease, Alzheimer's disease, cystic fibrosis, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, hyperproliferative disorders, infectious diseases, conditions associated with cell death, thrombin-induced platelet aggregation, chronic myelogenous leukaemia (CML), liver disease, pathologic immune conditions involving T cell activation, and CNS disorders. The compounds of Formula I may also be useful for treating a condition by modulation of mTOR activity by administering to a human or animal subject in need of such treatment an effective amount of the compound.

The design and synthesis of combinatorial libraries fused to the FKBP binding domain of rapamycin is premised on the finding that replacement of the effector domain of rapamycin by a tetrapeptide, provides rapamycin hybrid compounds that retain most of the high affinity FKBP-binding activity of rapamycin.

Previous synthesis of the FKBD from rapamycin involved the initial cleavage of the inherently labile ester bond at C-34 of rapamycin, which necessitated the reassembly of the two resulting pieces of FKBD. Alternatively, the disclosure provides a simpler and more efficient method to prepare the desired FKBP from rapamycin while keeping the entire FKBD intact throughout the process.

As shown below in Scheme 1, degradation of rapamycin (1) and reassembly of two fragments (4) and (5) provide the core structure (6) that is required for FKBP binding.

Scheme 1

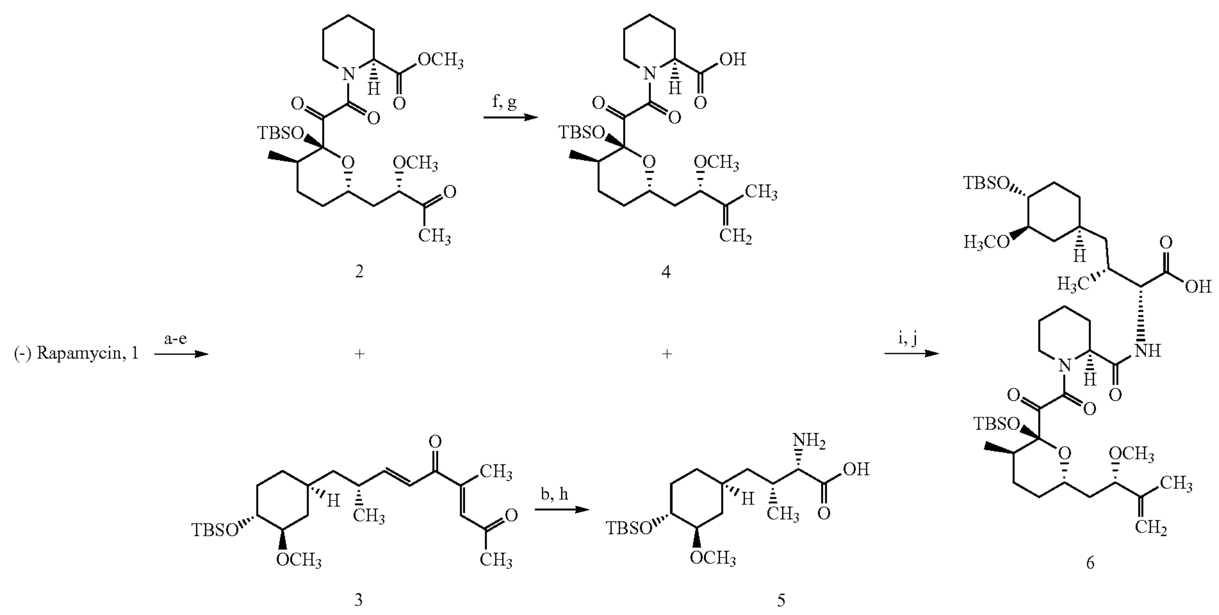

2 4 3 5 6

Reagents and Conditions: (a) 3 equiv. TBSOTf, 2,6-lutidine, $Et_3N$, $CH_2Cl_2$, 0° C.; (b) $0_3$, -78° C., $CH_2Cl_2/CH_3OH$, then $(CH_3)_2S$; (c) $Ph_3PCHCO_2CH_3$, $CH_2Cl_2$; (d) DBU, THF, 0° C.; (e) $CH_2N_2$, $Et_20$, 0° C.; (f) $(Ph_3P^+Me)I^-$, NaH, THF; (g) aqueous LiOH, THF; (h) $CO/(PPh_3)_2PdBr_2/LiBr/H_2S0_4$, DMF; then enzyme hydrolysis; (i) 4 plus NHS, DCC, DMAP, $CH_2Cl_2$; and then add 5; (j) Piperidine, DMF.

Commercially available rapamycin (1) is first subjected to silyl protection of the C-40, C-28, and C-10 hydroxyl groups using tert-butyldimethylsilyl triflate ((a) 3 equivalents of TBDSOTf or TBSOTf, 2,6 lutidine, triethylamine ($Et_3N$), and dichloromethane ($CH_2Cl_2$) at 0° C.). Other suitable hydroxyl protecting groups include but are not limited to methoxymethyl ether (MOM), tetrahydropyranyl ether (THP), tert-butyl ether (t-Bu), allyl ether, benzyl ether, tert-butyldiphenylsilyl ether (TBDPS), acetic acid ester, pivalic acid ester, benzoic acid ester, and the like.

The triprotected rapamycin is then fragmented using exhaustive ozonolysis via a known optimized protocol ((b) $O_3$, −78° C., $CH_2Cl_2/CH_3OH$, then $(CH_3)_2S$) to afford the pipecolate fragment (2) and cyclohexane-containing enone (3).

Pipecolic acid (4) is readily derived from the pipecolate fragment (2) by installing the methylene group on C-17 (rapamycin numbering) using a Wittig reaction ((f) $(Ph_3P^+Me)I^{-1}$, NaH, THF) and saponification of the ester (at C-31) ((g) aqueous LiOH, THF) to provide the desired pipecolate (4) for eventual coupling. Fragment (3) is further degraded by another exhaustive ozonolysis ((b) $O_3$, −78° C., $CH_2Cl_2/CH_3OH$, then $(CH_3)_2S$) to yield an intermediate aldehyde, which upon stereoselective Strecker synthesis ((h) $CO/(PPh_3)_2PdBr_2/LiBr/H_2SO_4$, DMF; then enzyme hydrolysis) yields the required amino acid (5). Finally, preparation of N-hydrosuccinimide active ester of pipecolate (4) ((i) 4 plus NHS, DCC, DMAP, $CH_2Cl_2$), and subsequent condensation with amino acid (5) ((j) Piperidine, DMF) provides the FKBD of rapamycin (6), which is ready for peptide coupling at the proximal pipecolic acid end and a ring-closing metathesis reaction at the distal alkenyl end.

Alternatively, as shown below in Scheme 2, the synthesis of the FKBD from rapamycin may be accomplished as follows.

Scheme 2

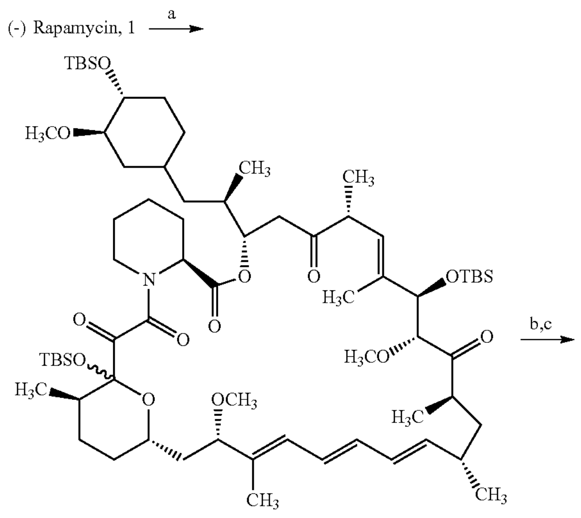

(2)

-continued

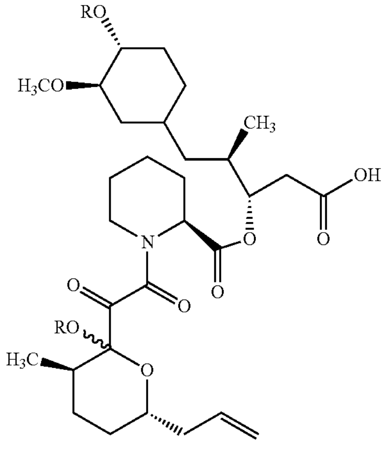

R = TBS (3)
R = (4)
d

Reagents and Conditions: (a) 3 equiv. TBSOTf, $Et_3N$, $CH_2Cl_2$, room temperature, 100%; (b) $0_3$, $CH_2Cl_2$, -68° C., then 35% $H_2O_2$, room temperature; (c) $CH_3PPh_3Br$, t-BuOK, THF, 0° C., 54% b and c; (d) $CF_3COOH$, $H_2O$, 0° C., 96%.

Treatment of rapamycin (1) with tert-butyldimethylsilyl triflate and triethyl amine ((a)TBSOTf, $Et_3N$, $CH_2Cl_2$, room temperature, 100%) affords the fully protected epimers (2) in quantitative yield. According to an earlier report, protection of the hydroxyl at the hemiketal center (C-10) of rapamycin is not required following the ozonolysis step. However, the corresponding C-10 unprotected FKBD fragment may be cleaved between C-9 and C-10 when subjected to Baeyer-Villiger oxidation. Thus, protection of the C-10 hydroxyl is required in this scheme. The rapamycin derivative (2) is subjected to ozonolysis and subsequently treated with hydrogen peroxide ((b) $O_3$, $CH_2Cl_2$ at −68° C., and 35% $H_2O_2$) to give an intermediate containing a carboxylic acid at one end and a peroxyhemiacetal or aldehyde at the other end of the FKBD fragment. After a brief flash-column chromatography over silica gel, the crude product was directly subjected to Wittig olefination ((c) CH3PPh3Br, t-BuOK, THF, 0° C.) to acid (3) in 54% combined yield. Deprotection of the silyl protecting groups ((d) trifluoroacetic acid and $H_2O$ at 0° C.) provides the product FKBD (4) in 96% yield. It is noteworthy that neither tetrabutylammonium fluoride (TBAF) nor HF-pyridine were able to accomplish a clean deprotection of the two silyl groups. Thus, the FKBD may be prepared from rapamycin in four steps with 52% overall yield.

The intermediates after ozonolysis and the Baeyer-Villiger reaction were not capable of being analyzed due in part to the complexity of the reaction products. The complexity was further compounded by the propensity of the FKBD to exhibit rotamerism and in this case we were also dealing with a pair of epimers. As shown below in Scheme 3, the most likely intermediates in the course of these two tandem steps (ozonolysis/Baeyer-Villiger) can be predicted as follows.

Scheme 3

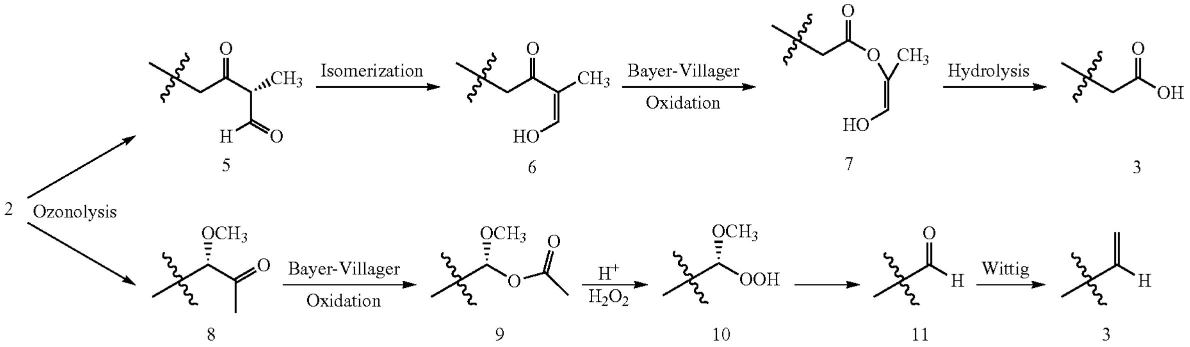

Ozonolysis of the C29-C30 double bond gave rise to aldehyde intermediate (5) that could undergo facile enolization to give 6. This rendered 6 with an exclusive migratory aptitude in the Baeyer-Villiger rearrangement to give ester 7. Hydrolysis of 7 led to the formation of the carboxylic group in 3. Concurrently, ozonolysis of C17-C18 double bond yielded the ketone intermediate 8. Baeyer-Villiger oxidation of 8 led to the formation, possibly via ester 9, of peroxy-hemiacetal (10) that, upon hydrolysis, gave the corresponding aldehyde 11, which is ready to undergo Wittig reaction to form the terminal olefin in 3. An interesting feature of this procedure is that the same set of reactions occurred concomitantly at both ends of FKBD, but led to the formation of distinct functional groups—a carboxylic acid and an olefinic group. This simultaneous chemical transformation of two groups significantly reduced the number of steps required to prepare FKBD, hence the high overall yield.

In addition to serving our purpose for the synthesis of FKBD-containing hybrid combinatorial libraries, high-affinity ligands of FKBP isoforms may find use as probes for a number of biological processes, as FKBP themselves have been implicated in the regulation of neuronal cell differentiation, ion channels, and Ras post-translational modification among others. The easy access to FKBD could thus allow for the synthesis of potent and possibly iso-form-selective FKBP ligands that are devoid of immunosuppressive and antiproliferative activity of FK506 and rapamycin.

For the methods of making the libraries, there are several different variations of achieving the macrocyclization. They include ring-closing metathesis (Scheme 4, 7, 11), safety catch method (Scheme 6, 10), thiol displacement (Scheme 14) and amide bond formation (Scheme 15).

As shown below in Scheme 4, the synthesis of a peptide library using the FKBD of rapamycin (6), can be prepared using the well-established solid-phase split-pool peptide synthesis method.

Scheme 4

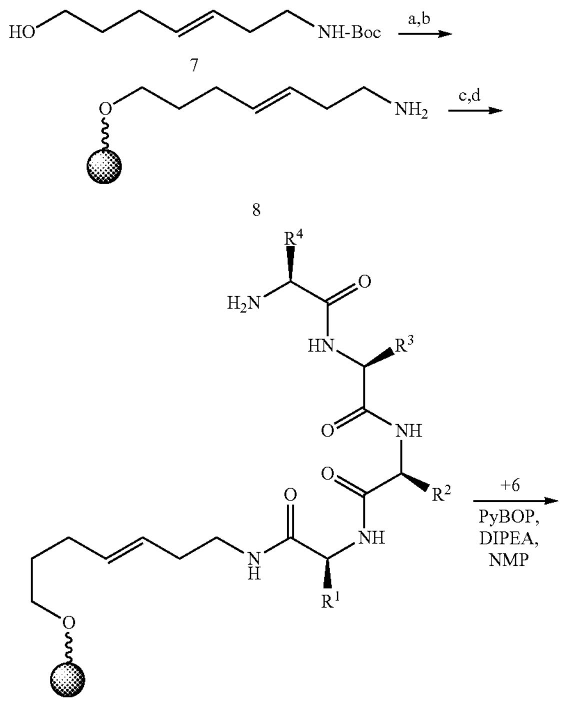

7

8

9

-continued

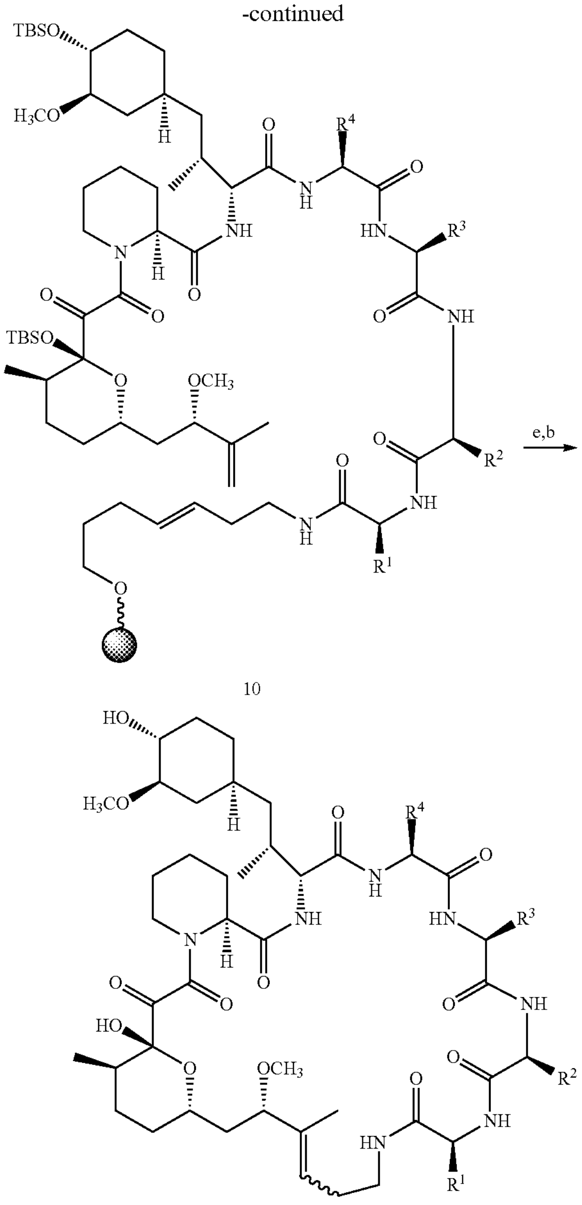

10

11

Reagents and Conditions: (a) 7 then, NaH/THF; add to Wang resin; (b) 15% $TFA/CH_2Cl_2$; (c) Fmoc-AA-OH, PyBOP, DIPEA, NMP; (d) Piperdine, NMP; (e) $(IMesH_2)(PCy_3)(Cl_2)Ru{=}CHPh$, $CH_2Cl_2$.

The library may be anchored to resin via a pre-installed olefinic group in order to enable the final cyclization step using olefin metathesis chemistry. Thus, the known Boc-protected α,γ-hydroxyalkenylamine linker (7) may be charged onto commercially available Wang resin using a well-established protocol ((a) 7 then, NaH/THF; add to Wang resin) to provide (8). After deprotection with trifluoroacetic acid to remove the Boc-protecting group ((b) 15% $TFA/CH_2Cl_2$), the resin is ready for a series of amino acid coupling steps using conventional Fmoc-based solid-phase peptide synthesis ((c) Fmoc-AA-OH, PyBOP, DIPEA, NMP). Thus, the amino acid couplings may be repeated until a tetrapeptide (9) is built on the resin. The tetrapeptides, together with the added spacer, provides for a ring size that is comparable to that of rapamycin. For building blocks, the five charged amino acids, Asp, Glu, His, Arg, and Lys are omitted to make the resulting tetrapeptides more hydrophobic, as the effector domains for both FK506 and rapamycin are bound to hydrophobic pockets of calcineurin and TOR. This protocol leads to a library of $15^4$ or 50,625 individual peptides. To suit the Fmoc-strategy and to set up for a one-step deprotection in the end, compatible protecting groups for side chains of the amino acid building blocks are utilized, i.e., trityl or tert-butyl for Ser, Cys, Thr, and Tyr.

In addition to alpha and beta amino acids, the Effector Domain may include N-methylated and N-alkylated amino acids as well as both D- and L-amino acids. Other useful amino acids include but are not limited to peptoids, peptidomimetic, depsipeptides, and mixtures thereof.

Upon completion of the tetrapeptide synthesis, the precursor of FKBD of rapamycin, (6), may be coupled to the C-terminal carboxylate group of (9). The cyclization of the peptides (10) may be achieved using a metathesis reaction with a Grubb's second-generation catalyst, accompanied with the release of the cyclic peptides from the resin ((e) $(IMesH_2)(PCy_3)(Cl_2)Ru{=}CHPh$, $CH_2Cl_2$). Finally, the products may be treated with trifluoroacetic acid to remove the silyl protection on FKBD of rapamycin and all the amino acid side-chain protecting groups simultaneously in one step ((b) 15% $TFA/CH_2Cl_2$). The beads may be filtered and removed and the desired library products are ready for high throughput screening by simply evaporating the volatiles from the reaction under high vacuum. The composition and integrity of each pool of compounds may be determined using LC-Mass spectrometry.

PyBOP (benzotriazol-1-yl-oxytripyrrolidinophosphonium hexafluorophosphate) is a peptide coupling reagent used in solid phase peptide synthesis. It is used as a substitute for the BOP reagent, thus avoiding the formation of the carcinogenic side product HMPA.

N,N-Diisopropylethylamine, or Hünig's base, DIPEA or DIEA, is an organic compound and an amine. It is used in organic chemistry as a base. Because the nitrogen atom is shielded by the two isopropyl groups and an ethyl group only a proton is small enough to easily fit. Similar to 2,2,6,6-tetramethylpiperidine, this compound is a good base but a poor nucleophile, which makes it a useful organic reagent.

Wang resin (4-benzyloxybenzyl alcohol resin) is the most popular support for solid phase organic synthesis (SPOS) using Fmoc chemistry. As a standard support it can be used for the solid phase immobilization of acids and phenols for SPOS. The ester linkage may be achieved, which has good stability to a variety of reaction conditions, but can be readily removed with the moderate acid treatment, generally with trifluoroacetic acid. For the immobilization of amines, Wang resin also can be readily converted into solid phase equivalents of standard urethane-based protecting groups by reaction with phosgene or activated carbonates, such as carbonyl diimidazole or bis(p-nitropnenyl)-carbonate. Other suitable resins include but are not limited to polystyrene resins such as aminomethyl polystyrene resin, 2-chrlotrityl chloride resin, DHP HM resin, HMPA-AM resin, Knorr resin, Knorr-2-chlorotrityl resin, MBHA resin, Merrifield resin, oxime resin, PAM resin, Rink amide-AM resin, Rink amide-MBHA resin, Sieber resin, Wang resin, Weinreb AM resin, Boc-Ser-Merrifield resin, and Boc-Gly-Merrifield resin, and the like.

The "one-bead-one-compound" (OBOC) combinatorial library method may be used to synthesize millions of compounds such that each bead displays only one compound. Bead libraries are screened, and positive beads are isolated for structure analysis.

The linking group (linker) that joins the substrate to the resin bead is an essential part of solid phase synthesis. The linker is a specialized protecting group, in that much of the time, the linker will tie up a functional group, only for it to reappear at the end of the synthesis. The linker must not be affected by the chemistry used to modify or extend the attached compound. The cleavage step should proceed readily and in a good yield as the best linker allows for attachment and cleavage in quantitative yield.

Grubbs' Catalyst is a transition metal carbene complex named after Robert H. Grubbs, the chemist who first synthesized it. There are two generations of the catalyst, as shown below:

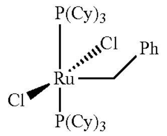

First Generation

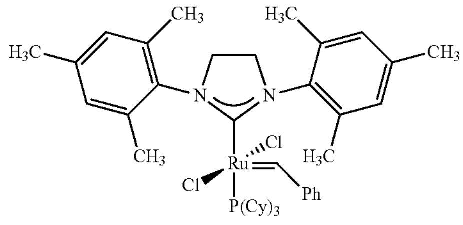

Second Generation

In contrast to other olefin metathesis catalysts, Grubbs' Catalysts tolerate other functional groups in the alkene and are compatible with a wide range of solvents. For these reasons, Grubbs' Catalysts are extraordinarily versatile.

The First Generation Catalyst is often used in organic synthesis to achieve olefin cross-metathesis, ring-opening metathesis polymerization (ROMP), acyclic diene metathesis polymerization (ADMET), and ring-closing metathesis. It is easily synthesized from $RuCl_2(PPh_3)_3$, phenyldiazomethane, and tricyclohexylphosphine in a one-pot synthesis. Grubbs' Catalyst is a relatively stable compound in air, which makes handling very easy. The IUPAC name of the 1st Generation Catalyst is benzylidene bis(tricyclohexylphosphine)-dichlororuthenium. The Second Generation Catalyst has the same uses in organic synthesis as the First Generation Catalyst, but has a higher activity. This catalyst is stable toward moisture and air, thus it is easier to handle in the lab. The IUPAC name of the Second Generation Catalyst is benzylidene[1,3-bis(2,4,6-trimethylphenyl)-2-imidazolidinylidene]dichloro(tricyclohexyl-phosphine)ruthenium. Both generations of the catalyst are commercially available.

Olefin metathesis is a reaction between two molecules containing double bonds. The groups bonded to the carbon atoms of the double bond are exchanged between molecules, to produce two new molecules containing double bonds with swapped groups. Whether a cis isomer or trans isomer is formed in this type of reaction is determined by the orientation the molecules assume when they coordinate to the catalyst, as well as the steric interactions of the substituents on the double bond of the newly forming molecule. Other catalysts are effective for this reaction, notably those developed by Richard R. Schrock, i.e., the Schrock carbene.

In addition to the hybrid combinatorial peptide library described above, there are many more options for both the building blocks of the library and the synthetic routes. For example, instead of naturally occurring alpha L-amino acids, beta-amino acids, D-amino acids, p-amino acids, N-methyl amino acids (as seen in CsA) or peptoids, and non-amino acids may be used in versions of the hybrid libraries. The lengths of the peptides or other building blocks can also be decreased or increased as well. Linkages other than peptide and olefins may also be used to connect the library to FKBD of rapamycin. These variations can give rise to significantly greater diversity and biochemical properties of the combinatorial fusion libraries.

Aside from the standard amino acids, there are many other non-standard amino acids that may be used in the disclosed methods and compounds. For example, carnitine, hydroxyproline, selenomethionine, hydroxyproline, lanthionine, 2-aminoisobutyric acid, dehydroalanine, and the neurotransmitter gamma-aminobutyric acid (GABA). Nonstandard amino acids often occur as intermediates in the metabolic pathways for standard amino acids for example, ornithine and citrulline occur in the urea cycle, part of amino acid catabolism. A rare exception to the dominance of α-amino acids in biology is the j-amino acid beta alanine (3-aminopropanoic acid), which is used in plants and microorganisms in the synthesis of pantothenic acid (vitamin Bs), a component of coenzyme A. Other α-amino acids and β-amino acids are contemplated to be within the scope of the invention.

Figure 2:
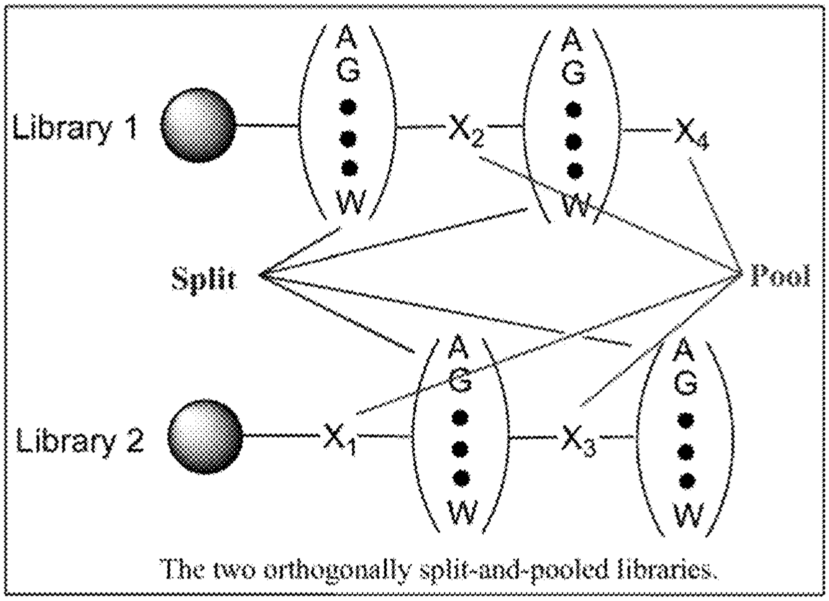
FIG. 2 shows the two orthogonally split and pooled libraries.

To facilitate the decoding of the hits, two orthogonally split-and-pooled libraries with one kept split at the $1^{st}$ and $3^{rd}$ and the other at $2^{nd}$ and $4^{th}$ coupling steps, respectively may be used (FIG. 2). This provides two partially "decodable" libraries, each consisting of 15×15 or 225 individual pools. By screening the first library, the identities of the $1^{st}$ and $3^{rd}$ residues of the hits may be known as they remained in different pools. By screening the orthogonally split-and-pooled library, the amino acid identities of the $2^{nd}$ and the $4^{th}$ residues of the hits may also be known. The combined information of the two orthogonally split-and-pooled libraries provides for the optimal sequences of the hits. It is possible that more than one residue may show up at a given position, which can be further determined by synthesizing and testing all possible combinations of individual cyclic peptides.

A feature of the soluble libraries is that they are made in a partially split-pooled manner (see FIG. 2). Two sets of each library may be made that are orthogonally split and pooled. In the end, each pool will contain a mixture with certain defined positions. By screening the two orthogonal pools simultaneously, it will be possible to decode the residues at each and every position, allowing for the decoding of the hits.

The orthogonally split-and-pooled library pairs can be screened using most other screening platforms, including cell-based screens or protein-target based screens in addition to the protein chip. In fact, if there is a predetermined pathway (such as hedgehog, Wnt, Myc etc) or target (Bcr-Abl, VEGFR, Her2 etc), the cell-, pathway- or target-based screens may be used instead of the more comprehensive whole proteome chip screens.

For the libraries retained on beads, they may be made in a split-pool strategy so that each bead will contain a single homogeneous compound (so-called one-bead-one-compound or OBOC strategy). These solid-phase libraries will be screened using the beads directly. This type of solid-phase libraries is suitable for screening against selected single protein target only. In one format, the target protein may be labeled with a fluorescence marker. The labeled protein may be incubated with the solid-phase libraries (with 200,000 to over 1 million individual compounds on individual beads per library) with the fluorescently labeled target protein in the absence and presence of recombinant FKBP. The positive hits may be identified by the fluorecent intensity of the beads. If a bead contains a positive hit, it is expected that it will bind to the fluorescently labeled target protein. Those beads will then be selected using either a micropipet or by flow cytometry. The identities of the hits may also be determined using mass spectrometry. As a follow-up, the same compounds may be made individually, released into solution and tested in complementary assays.

Figure 3:
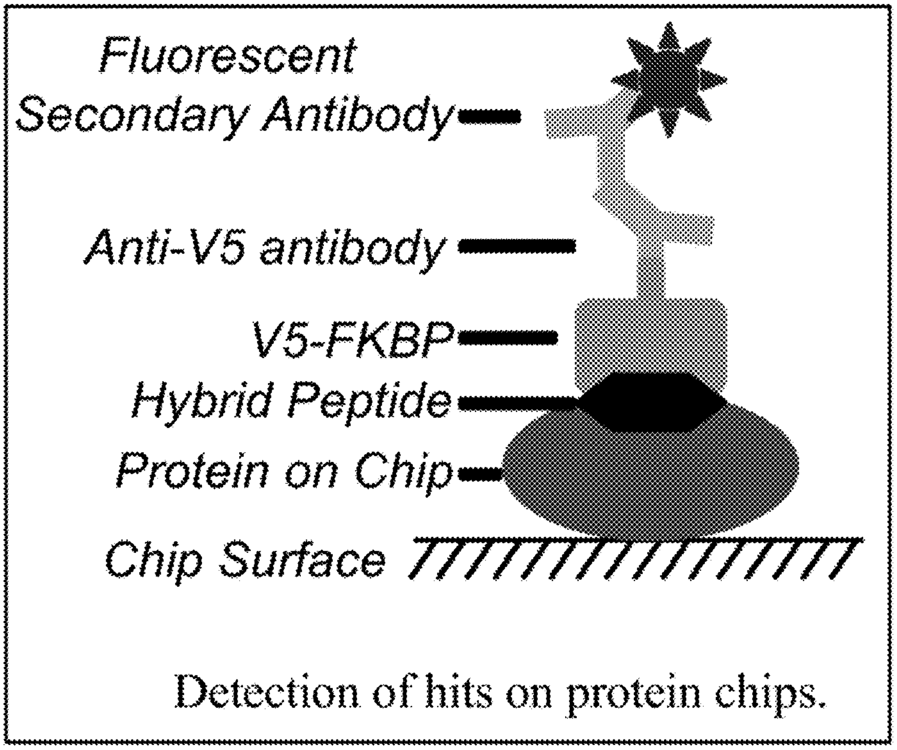
FIG. 3 shows the detection of hits on protein chips.

Human protein chips may be made from glass slides of 3.5 cm by 7.5 cm in dimension. Each chip can be screened in a chamber containing 2-3 mL of buffer. To detect the hits that form complexes with FKBP and another protein present on a chip, a recombinant FKBP containing a C-terminal V5 peptide epitope tag may be generated against which there are highly specific antibodies. The detection is rendered possible by using anti-V5 antibody together with a fluorescently tagged secondary antibody (FIG. 3). Thus, upon incubation of the library and V5-tagged FKBP, those proteins that are bound to V5-FKBP may be detected through the presence of fluorescence at the locations where the proteins are placed in the array.

The two orthogonally split-and-pooled libraries may be screened using one pool per chip. Thus, a total of 450 pools of hybrid compounds can be screened using 450 chips. Each compound may be present at a final concentration of about 1 μM. The total binding capacity of each pool of 225 compounds for FKBP is 225 μM. To ensure that all compounds are bound by V5-FKBP protein, V5-FKBP at a final concentration of 500 μM is used, which is easily achievable due to its high aqueous solubility. Upon incubation of V5-FKBP and a pool of the compounds with the proteins on protein chips, the chips may be washed three times with the binding buffer, followed by addition of anti-V5 antibody and a fluorescein-tagged secondary antibody. The chips may be further washed before its fluorescence pattern is recorded in a chip reader. The identities of the proteins may be retrieved based on the physical locations of fluorescent spots on the chip. As FKBP is known to bind a small number of proteins itself, a parallel screen in the absence of added library may also be conducted, which may serve as a negative control. The fluorescence intensity of each protein spot may be quantitated and normalized against that from the V5-FKBP control. Those proteins whose fluorescence intensity becomes significantly higher in the presence of added hybrid cyclic peptide may be considered to be hits.

It is interesting to note that by screening the two libraries of 50,625 individual compounds against 450 human protein chips that contain 17,000 human proteins on each chip, an equivalent of a total of 2×50,625×17,000 or 1,721,250,000 individual binding assays may be accomplished.

For the hits that are bound to a given protein or a set of proteins, the corresponding tetrapeptide sequences based on the specific pools to which the hits belong may be decoded. From the two orthogonally split-and-pooled libraries, the optimal sequence or sequences of the four residues against a given protein target may be determined. Accordingly, all possible hybrid ligands may be synthesized and tested individually using the chip assay. Upon validation on protein chips, a pull-down assay with GST-FKBP and the putative recombinant target protein in the absence and presence of the hybrid ligands may be used. In the event that the putative target proteins are already known to play a role in a given cellular process, be it cell cycle progression, transcription, translation or apoptosis, the newly identified ligands may be subject to the appropriate cell-based assays to determine if they have the expected effects on the corresponding cellular processes.

The generation of orthogonally split-and-pooled libraries of hybrid cyclic peptides fused to FKBD enables the proteome-wide screening of human protein chips and facilitates the identification of hits that can be rapidly resynthesized and validated. The combination of the libraries with the protein chip screening platform renders it possible for the first time to perform large-scale screens of combinatorial libraries against the entire proteome to identify the small molecule hits and the protein targets simultaneously. Moreover, unlike compounds from conventional peptide libraries, the hits from the hybrid cyclic peptide and non-peptide libraries may be endowed with greater stability and cell permeability due to the presence of FKBD, which may make the hits readily applicable as probes of the cellular function of the putative targets. This approach may lead to a new paradigm for decoding the function of proteins in the human proteome, i.e., from proteins to binding ligands to cellular functions. There are also unlimited possibilities beyond the peptides that can be fused to FKBD as well as the cyclophilin-binding domain of CsA to give rise to even greater chemical diversity to cover more proteins in the human proteome.

The disclosure also provides methods for administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan.

The pharmaceutical compositions may be prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, orally, intravenously, or by another parenteral route, or as implants, or even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science, 249:1527-1533, 1990, which is incorporated herein by reference.

For delivery of the compounds, the formulations may be prepared by contacting the compounds uniformly and intimately with liquid carriers or finely divided solid carriers or both, and then, if necessary, shaping the product into the desired formulation. The carrier may be a parenteral carrier, or a solution that is isotonic with the blood of the recipient. Examples of such carrier vehicles include water, saline, Ringer's solution, dextrose solution, and 5% human serum albumin. Nonaqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

The composition described herein may be suitably administered by sustained release systems. Suitable examples of sustained release compositions include semipermeable polymer matrices in the form of shaped articles, e.g., films, microcapsules, or microspheres. Sustained release matrices include, for example, polyactides (U.S. Pat. No. 3,773,919), copolymers of L-glutamic acid and .gamma.-ethyl-L-glutamate (Sidman et al., Biopolymers 22:547-556, 1983), or poly-D-(−)-3-hydroxybutyric acid (EP 133,988). Sustained release compositions also include one or more liposomally entrapped compounds of formula I. Such compositions are prepared by methods known per se, e.g., as taught by Epstein et al. Proc. Natl. Acad. Sci. USA 82:3688-3692, 1985. Ordinarily, the liposomes are of the small (200-800.ANG.) unilamellar type in which the lipid content is greater than about 30 mol % cholesterol, the selected proportion being adjusted for the optimal therapy.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990; each of which is herein incorporated by reference.

The following examples are intended to illustrate but not limit the invention. While they are typical of those that might be used, other procedures known to those skilled in the art may alternatively be used.

EXAMPLES

This invention is illustrated by the following exemplar embodiments, which are not to be construed in any way as imposing limitations on the scope thereof. On the contrary, various other embodiments, modifications, and equivalents thereof, which, after reading the description herein, may suggest themselves to those skilled in the art, may be made without departing from the spirit or scope of the present invention. The following examples are intended to illustrate but not limit the invention.

Example 1

Synthesis of 2 in Scheme 2

To a solution of rapamycin (999 mg, 1.09 mmol) and anhydrous triethylamine ($Et_3N$) (0.6 mL, 4.45 mmol) in anhydrous dichloromethane ($CH_2Cl_2$) (3 mL) is added tert-butyldimethylsilyl triflate (TBSOTf) (0.85 mL, 3.79 mmol). The solution is stirred for 1 hour at room temperature and quenched with water. The resulting mixture is diluted with ethyl acetate (EtOAc) (120 mL), washed with saturated sodium bicarbonate ($NaHCO_3$) and brine, and dried and concentrated in vacuo. The crude residue is subjected to silica gel column chromatography (Hexanes/EtOAc, 8:1) to afford 2 (1.37 g, 100*) as a yellow solid: $^1$H NMR (400 MHz, $CDCl_3$): δ 6.39-5.82 (m, 4H), 5.52-4.91 (m, 4H), 4.45-3.98 (m, 2H), 3.83 (d, 7-4.0 Hz, 1H), 3.40 (s, 3H), 3.27 (s, 3H), 3.10 (s, 3H), 2.89-2.83 (m, 1H), 2.66-2.40 (m, 3H), 2.23-2.19 (m, 3H), 1.70 (s, 3H), 0.17-0 (m, 18H); $^{13}$C NMR (100 MHz, $CDCl_3$): δ 210.3, 206.6, 197.9, 169.5, 167.0, 139.3, 139.0, 136.6, 132.0, 130.8, 127.4, 126.7, 126.4, 101.7, 86.6, 84.3, 83.2, 78.0, 75.7, 74.3, 67.7, 58.1, 57.8. 56.1, 51.4. 45.8, 44.1. 41.4, 40.8, 40.6, 40.2, 38.2, 36.8, 35.7, 34.0. 33.9, 33.0, 32.0, 30.1, 27.1, 26.6, 26.3, 26.0, 25.9, 25.8, 25.7, 24.9, 22.0, 21.0, 19.3, 18.2, 18.1, 15.7, 15.5, 14.0, 13.9, 11.0, −2.5, −3.2, −4.5, −4.6, —4.7, −4.9; HR-ES1MS calcd for $C_{69}H_{121}O_{13}NSi_3Na$ [M+Na]*1278.8043, found 1278.8049.

Example 2

Synthesis of 3 in Scheme 2

Toa solution of the silyl derivative 2 (1.20 g, 0.95 mmol) in $CH_2Cl_2$ (15 mL) at −68° C. is bubbled ozone ($O_3$) until the blue color persisted. 35% hydrogen peroxide ($H_2O_2$) (15 mL) is added and the stirring is continued for another 14 hours at room temperature. The solution is diluted with EtOAc (120 mL), washed with brine, dried and concentrated to afford an oil that is purified using silica gel chromatography (Hexanes/EtOAc, 4:1, then $CH_2Cl_2$—MeOH, 20:1) to provide an epimeric mixture (710 mg) as a white solid. The epimeric mixture from the ozonolysis reaction stated above (210 mg, 0.26 mmol) is dissolved in anhydrous THF (2 mL), and added to a freshly prepared Wittig reagent at 0° C., which in turn was prepared from $CH_3PPh_3Br$ (560 mg, 1.57 mmol) and tert-BuOK (140 mg, 1.25 mmol) in anhydrous THF (5 mL). After stirring for 10 minutes, the reaction mixture is quenched with 5% HCl. The resulting mixture is diluted with EtOAc (60 mL), washed with brine, dried and concentrated. The crude residue is purified by silica gel chromatography (toluene-EtOAc. 4:1, then toluene-EtOAc-AcOH, 4:1:0.025) to provide 3 (124 mg, 54%) as a white solid: $^1$H NMR (400 MHz, $CDCl_3$): 5.84-5.68 (m, 1H), 5.29-4.89 (m, 4H). 4.42-4.29 (m, 1H). 4.06-3.85 (m, 1H), 3.40 (s, 3H), 2.93-2.48 (m, 4H). 2.34-2.13 (m, 4H), 0.87 (s, 9H), 0.19-0.02 (m, 12H); $^{13}$C NMR (100 MHz, $CDCl_3$): δ 197.7, 197.4, 176.0, 175.4, 169.7, 169.2, 167.2, 166.4, 135.3, 134.3, 117.2, 116.6, 102.0, 101.6, 84.5, 84.4, 75.7, 75.2, 74.6, 70.5, 70.3, 58.1, 58.0, 56.6, 56.5, 51.8, 44.4, 40.3, 38.9, 38.6, 36.5, 36.4, 36.2, 36.0, 35.1, 34.7, 33.9, 33.34, 33.25, 33.1, 31.4, 30.9, 30.6, 29.7, 29.4, 27.6, 27.3, 26.8, 26.76, 26.6, 26.3, 25.9, 24.8, 24.4, 22.8, 21.3, 20.7, 19.4, 18.2, 15.82, 15.78, 15.3, 14.9, −2.5, −2.7, −2.9, −3.0, −4.5, −4.7: HR-ES1MS calcd for $C_{42}H_{75}O_{10}NSi_2Na$ [M+Na]*832.4827, found 832.4833.

Example 3

Synthesis of 4 in Scheme 2

To a mixture of trifluoroacetic acid ($CF_3CO_2H$) (0.8 mL) and $H_2O$ (0.2 mL) at 0° C. is added olefin 3 (32 mg, 0.040 mmol). After stirring for 2 hours, the mixture is concentrated in vacuo and purified by silica gel chromatography ($CH_2Cl_2$—MeOH—AcOH. 20:1:0.2) to provide 4 (22 mg, 96%) as a white solid: $^1$H NMR (400 MHz, $CDCl_3$): 5.82-5.68 (m, 1H), 5.27-4.90 (m, 4H), 4.45-4.32 (m, 1H), 4.02-3.85 (m, 1H), 3.40 (s, 3H). 2.99-2.94 (m, 1H), 2.65-2.51 (m, 2H): $^{13}$C NMR (100 MHz, $CDCl_3$): δ 197.8, 194.8, 175.1, 175.0, 171.0, 170.0, 169.8, 169.3, 169.3, 167.6, 166.8, 165.7, 135.1, 134.8, 134.3, 117.4, 117.1, 116.7, 99.3, 98.5, 97.7, 84.4, 75.7, 75.2, 75.0, 73.9, 70.2, 70.1, 56.5, 56.4, 51.5, 44.5, 43.1, 41.5, 41.4, 40.2, 39.1, 38.9, 35.1, 35.0, 34.4, 34.3, 34.1, 33.4, 33.2, 31.3, 30.8, 30.6, 29.7, 27.5, 27.1, 26.6, 26.4, 26.3, 25.0, 24.6, 24.4, 21.1, 20.9, 20.8, 16.7, 16.1, 15.9, 15.7, 15.3, 15.1, 15.0; HR-ESIMS calcd for $C_{30}H_{47}O_{10}NNa$ [M+Na]*604.3098, found 604.3093.

Example 4

Synthesis of Macrocycles Containing Mimic of FKBD

The synthesis of novel mimic FKBD fragments—one for use in RCM macrocyclization strategy and one for macro-lactamization strategy, is shown below in Scheme 5.

Scheme 5

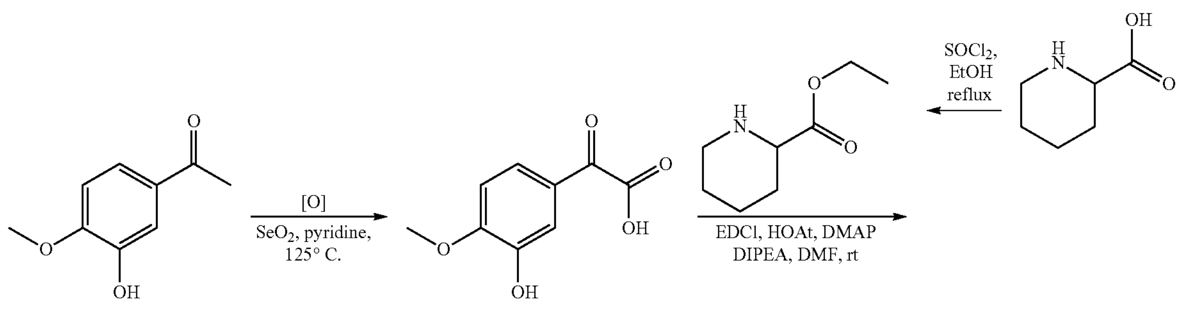

-continued

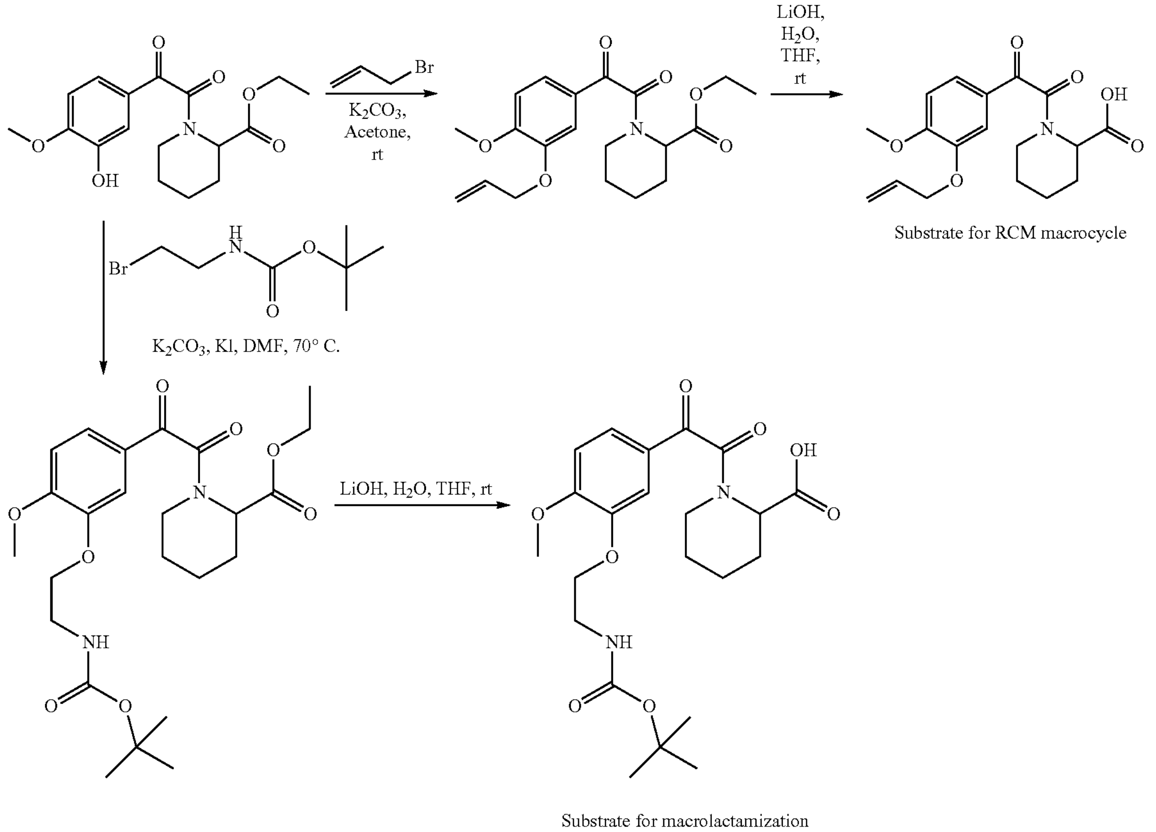

3'-Hydroxy-4'-methoxy acetophenone was dissolved in pyridine and oxidized with selenium dioxide at 125° C. to obtain the desired glyoxalate. This compound is then coupled with ethyl pipecolate using EDCI, HOAt, DMAP, DIPEA in DMF to obtain the key intermediate. The intermediate compound may be modified into either the RCM substrate or substrate for macrolactamization.

Macrolactamization Substrate

The key intermediate was reacted with tert-butyl-2-bromoethylcarbamate in presence of potassium carbonate and potassium iodide in DMF followed by base hydrolysis to obtain the desired substrate for solid phase coupling with D-HomoPhe terminated peptide sequence.

RCM Substrate

The key intermediate was reacted with allyl bromide in presence of potassium carbonate in acetone at room temperature followed by base hydrolysis to obtain the desired substrate for solid phase coupling with D-HomoPhe terminated peptide sequence.

Example 5

Macrocycle—Macrolactamization Strategy Using Safety Catch Linker

Two different tetrapeptides—Leu-Ala-Val-Gly-D-HomoPhe and Ala-Tyr(tBu)-N-MeLeu-Gly-D-HomoPhe were synthesized using standard solid phase coupling protocols. The mimic FKBD substrate was coupled to the terminal D-homophenylalanine followed by activation with $ICH_2CN$ in absence of light and subsequent removal of all Boc protecting groups using 50-80% TFA in DCM. This was followed by the macrolactamization with 20% DIPEA in THF and cyclitive release of the desired mimic rapafucin in 20-28% yield after purification. Synthesis of one of the peptide sequences is shown in Scheme 6.

Scheme 6

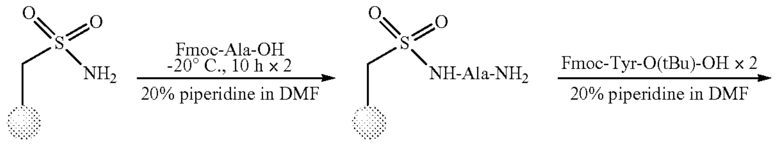

-continued
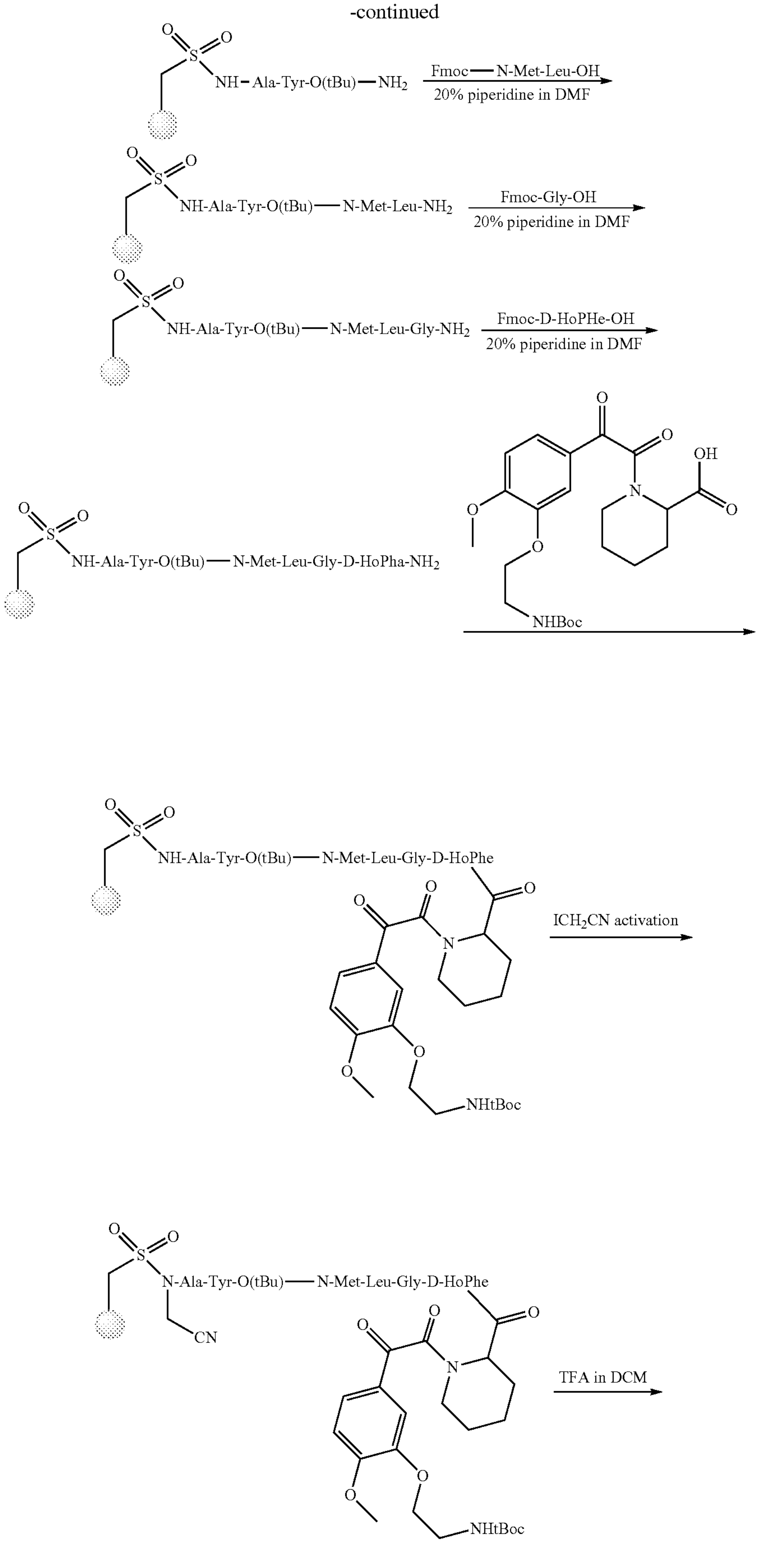

-continued

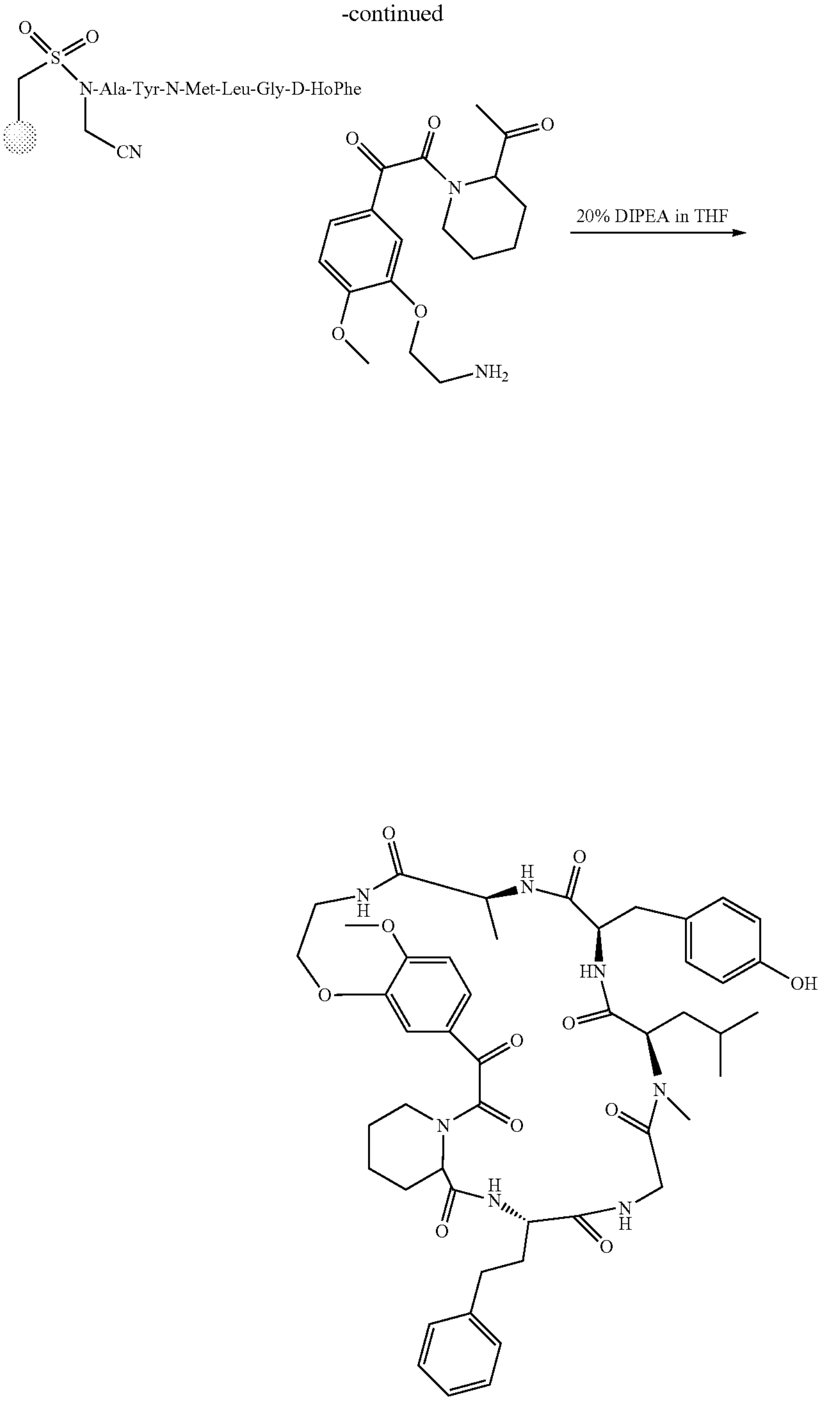

Example 6

Macrocycle—Ring-Closing Metathesis Strategy

The below linear precursor, with terminal double bonds, obtained from cleavage of product from chlorotrityl chloride resin was subjected to RCM using Grubb's second generation catalyst in solution phase using microwave conditions 120° C. for 30 min in DCE as well as traditional hotplate (50° C., overnight) to obtain the desired cyclized product in ~70% yield as shown in Scheme 7.

Scheme 7

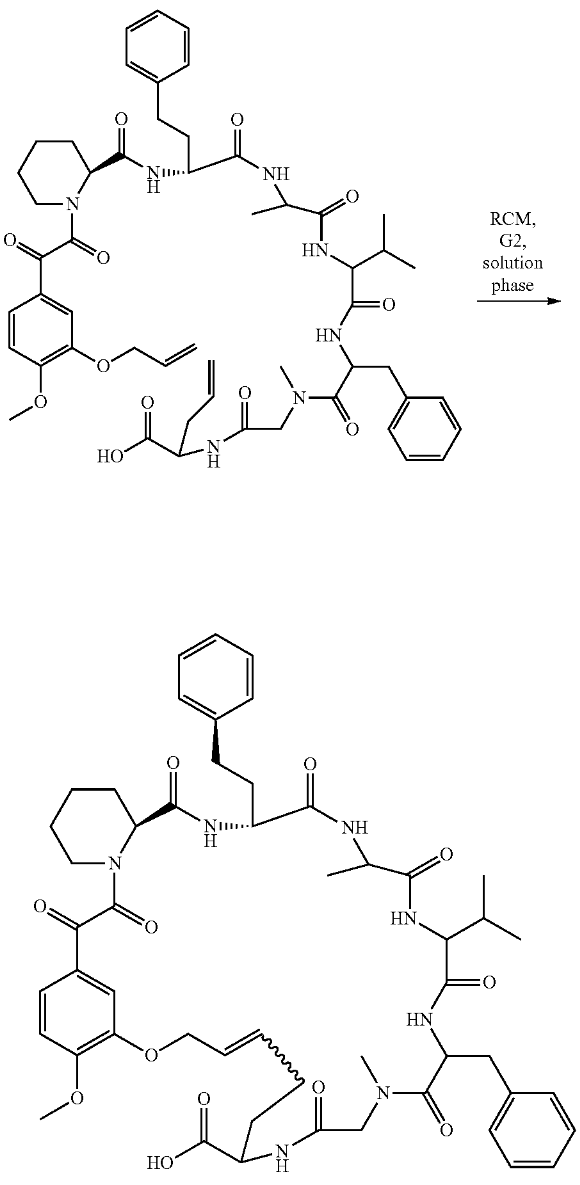

Example 7

Preparation of Natural FKBD from Rapamycin and Synthesis of Macrocycles

Treatment of Rapamycin with TBSOTf and $Et_3N$ in DCM offered a fully protected silylate, which was applied to ozonolysis and subsequent Baeyer-Villiger oxidation to provide a mixture of FKBD fragments as shown in Scheme 8.

Scheme 8

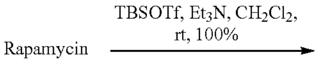

-continued

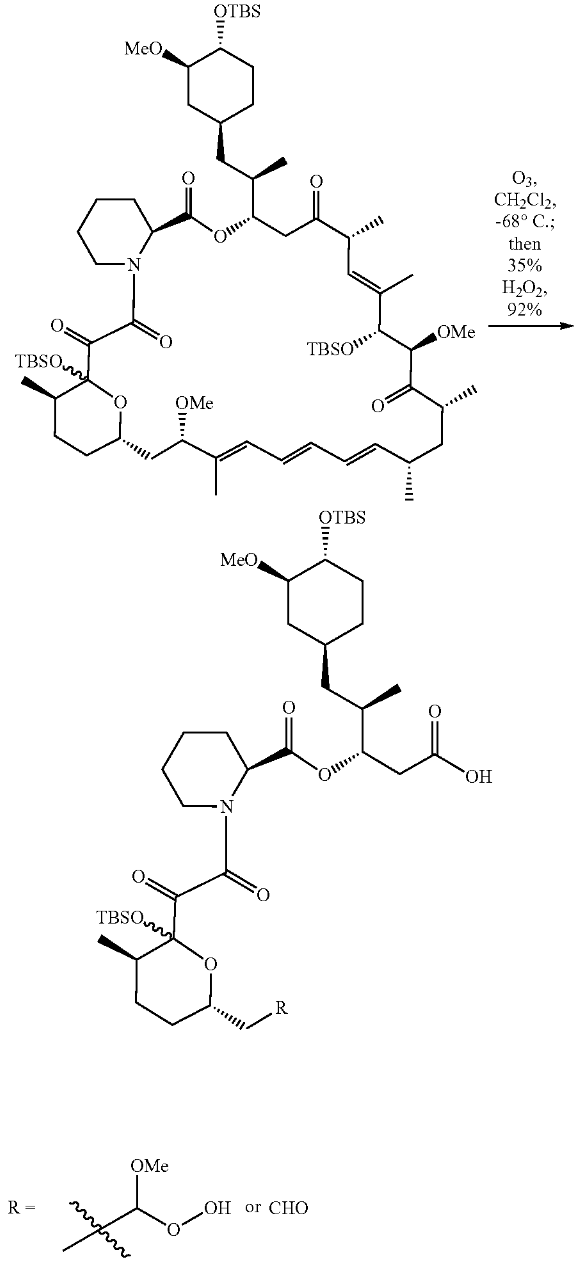

Example 8

Preparation of a Tetrapeptide. (Leu-Val-Ala-Gly)

The mixture of FKBD fragments was coupled with tetrapeptide under the condition of HBTU and DIPEA, and the R group was then treated with oxone to result in a carboxyl acid group, followed by coupling with N-Boc-ethylenediamine at 0° C. Deprotection of all the TBS groups with TBAF at 0° C. and subsequent activation with $ICH_3CN$ in darkness to provide an orange resin, which was then subjected to 50% TFA in DCM at 0° C. to give a free amino group. Treatment the ring-closed precursor above with 20% DIPEA in THF afforded the desired rapafucin in 16% overall yield as shown in Scheme 9 and 10.

Scheme 9
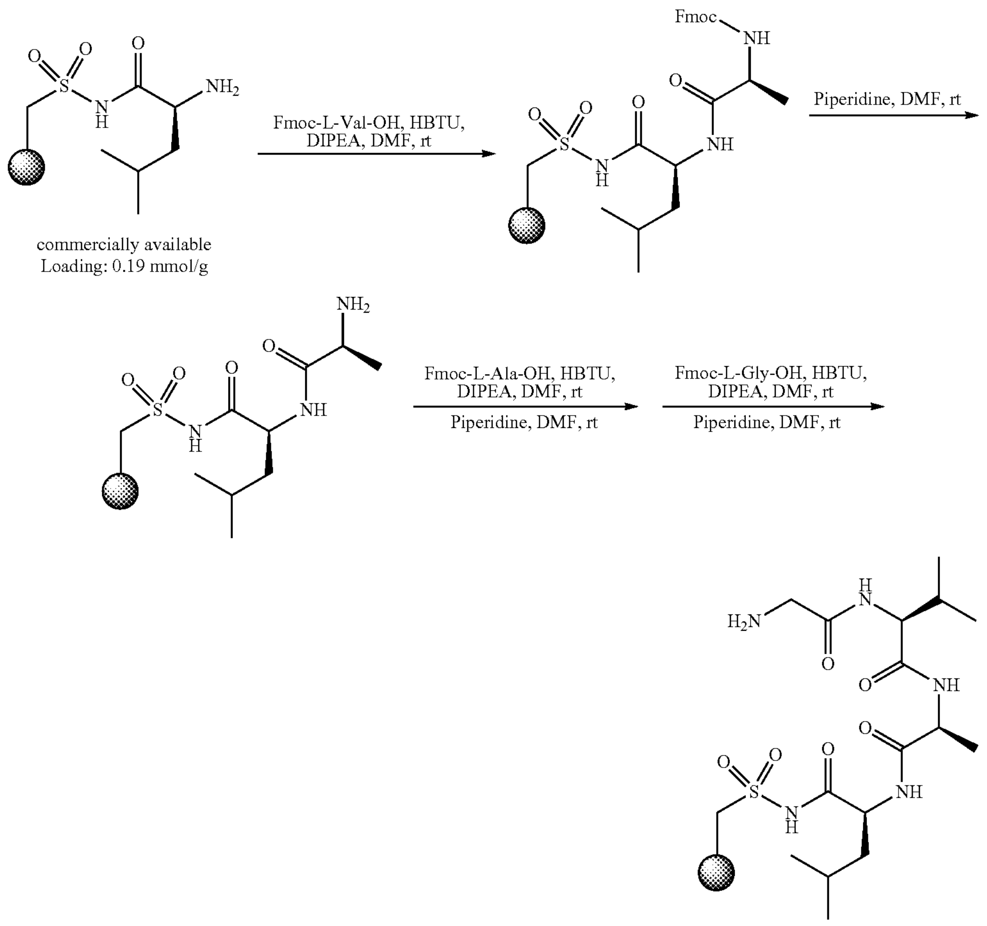
Scheme 10
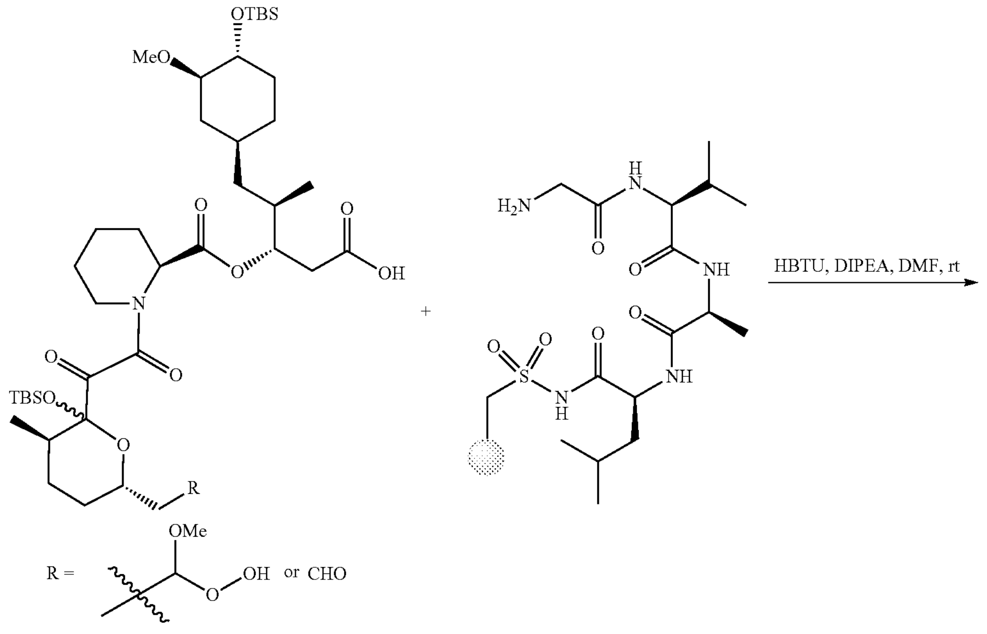

-continued
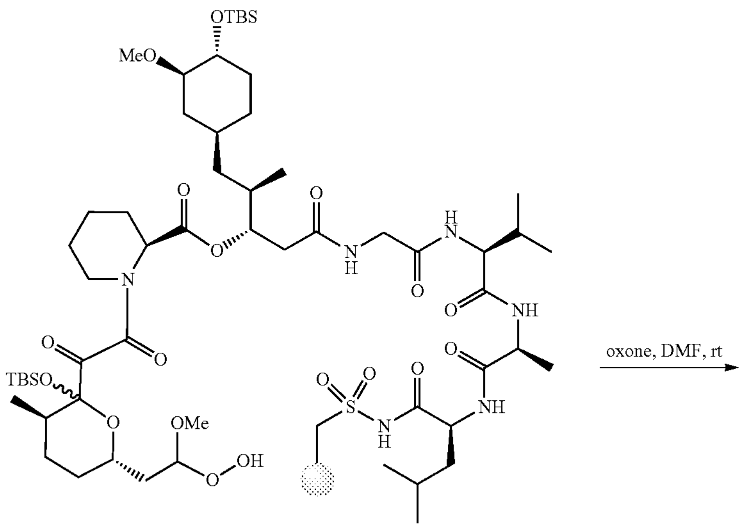
R = 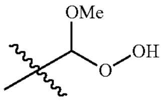 or CHO
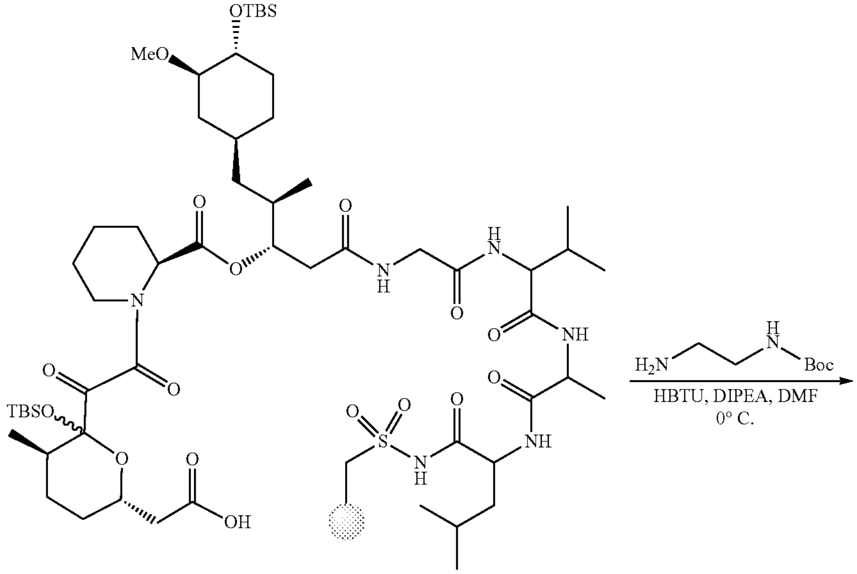

-continued
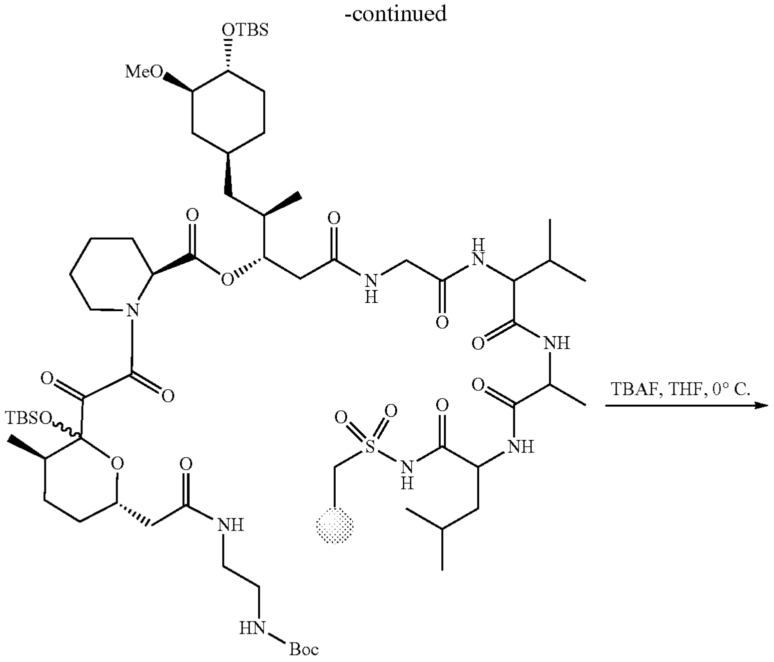
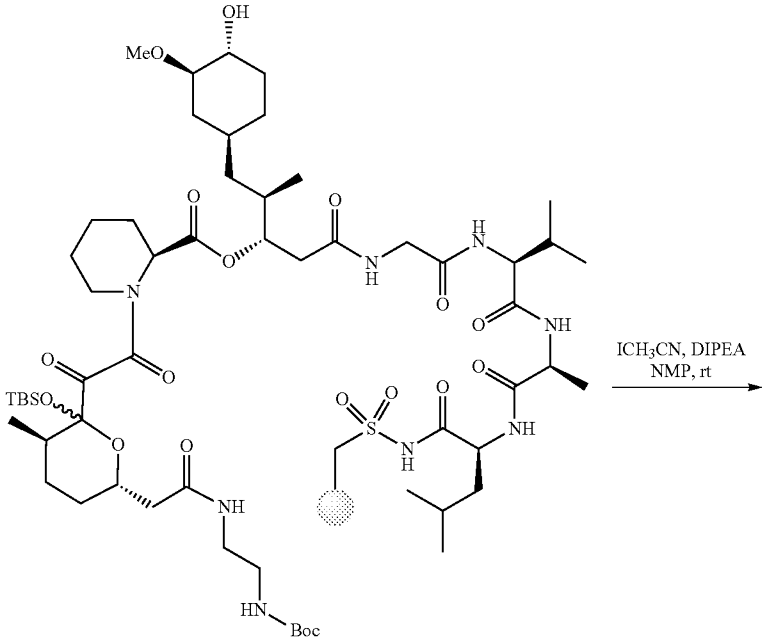

-continued
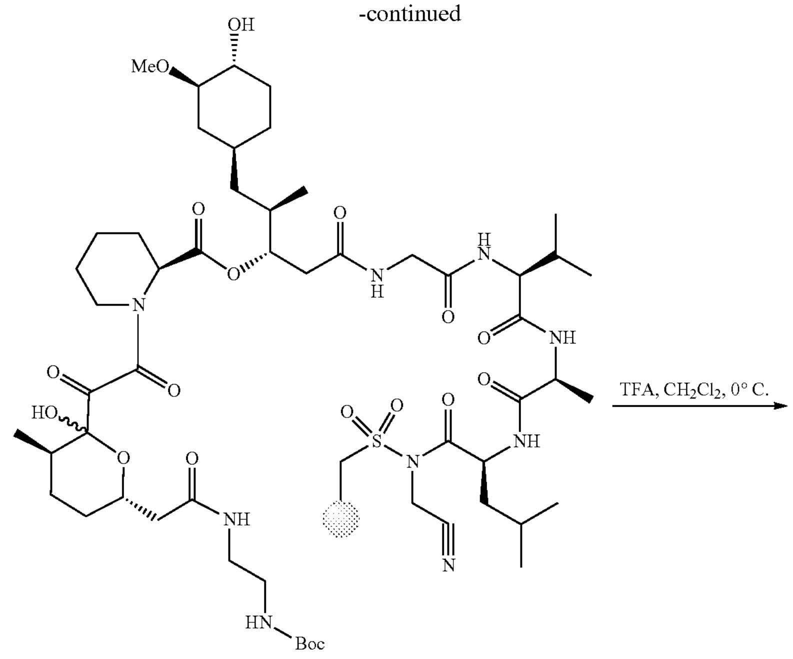
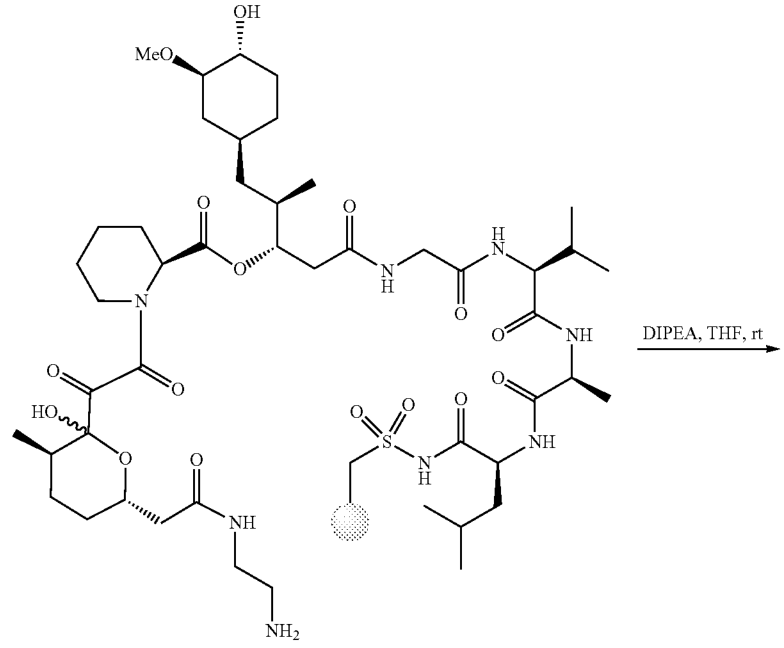

-continued
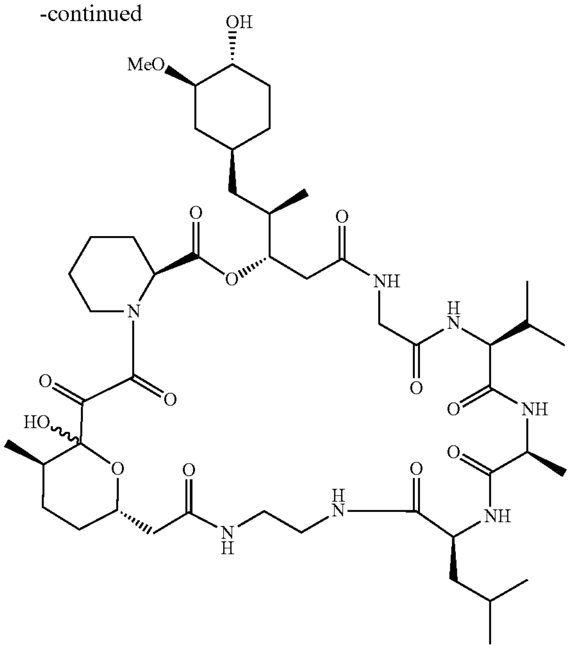
16%
Example 9
Macrocyclization Using Ring-Closing Metastasis
The macrocyclization using ring-closing metastasis is shown below in Scheme 11.
Scheme 11
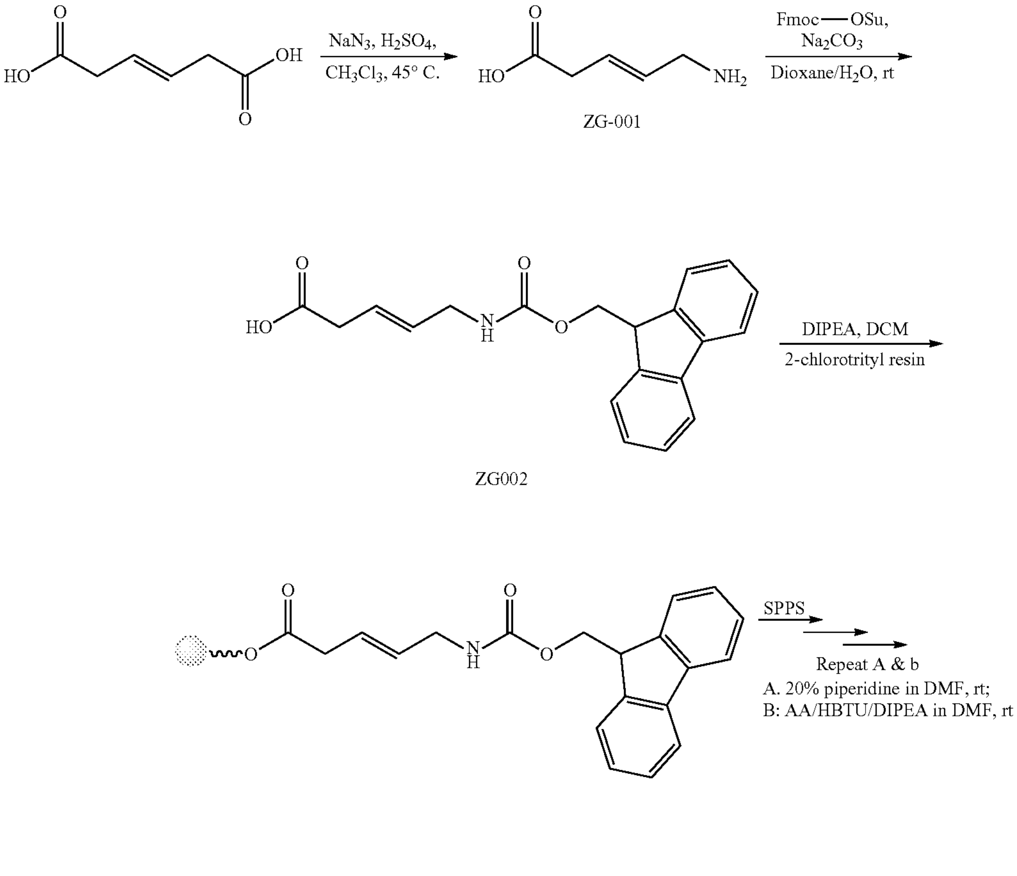

-continued
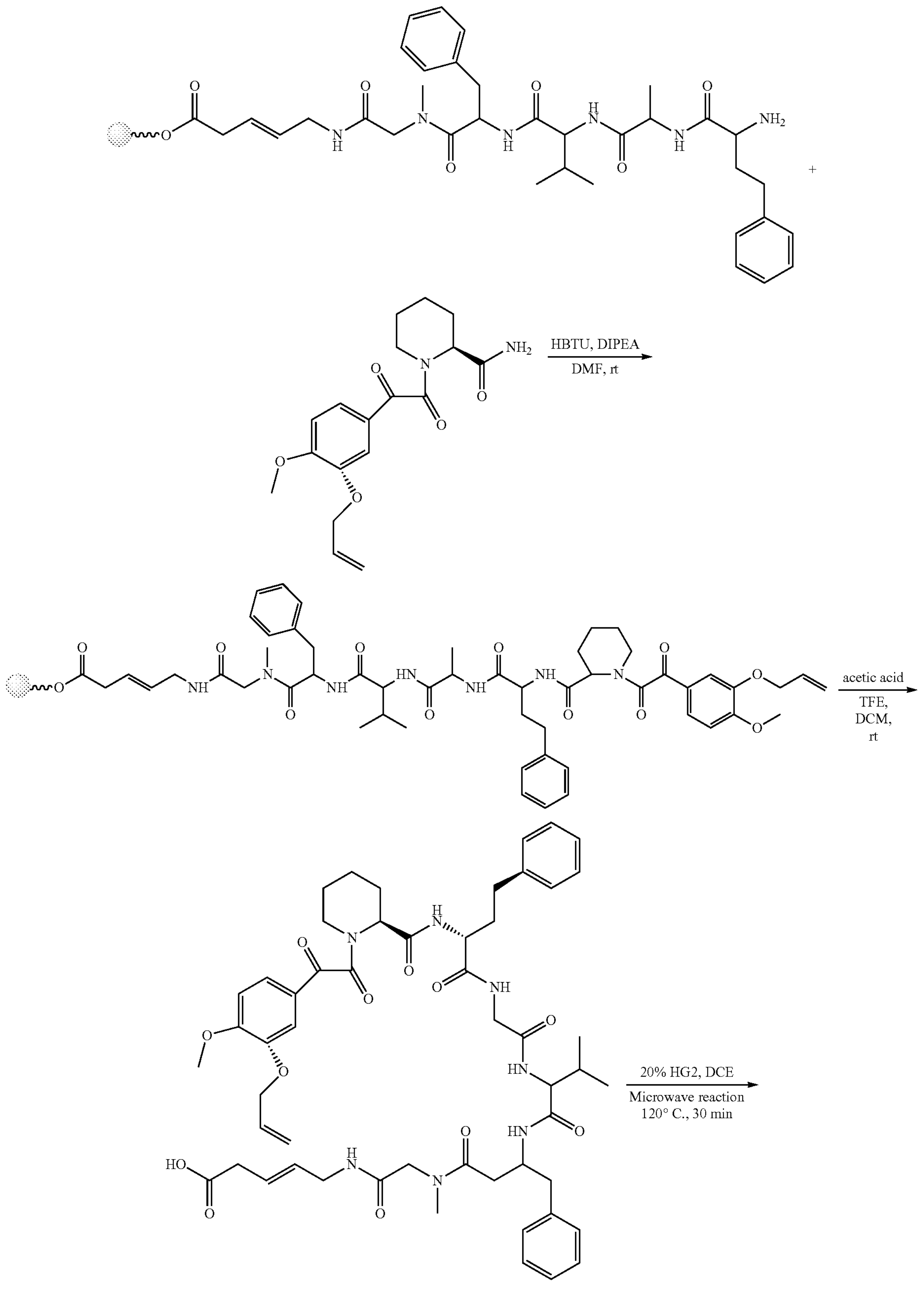
ZG-003

-continued

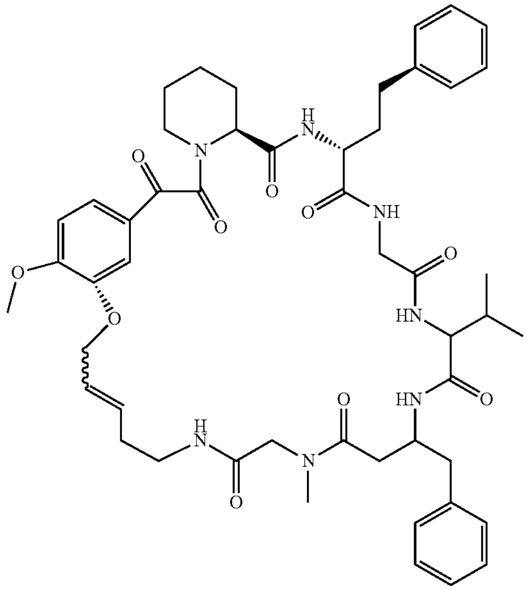

ZG-004

Example 10

Synthesis of ZG-001

Synthesis of linker ZG-002. The designed linker ZG-002 was prepared by protection of the amine group of ZG-001 with FMOC-OSu similar to reported synthetic strategy. Briefly, ZG-001 (115 mg, 1 mmol) was suspended in 10% $Na_2CO_3$ (2.4 mL) and cooled in an ice bath. A solution of Fmoc-OSu (337 mg, 1 mmol) in dioxane (3 mL) was then added in 3 portions under stirring over a period of 30 min. After further 4 h at room temperature, the reaction mixture was diluted with water (30 mL) and then extracted with ether (30 mL, 3 times). The remaining aqueous phase was cooled, acidified to pH2.0 with 1N HCl, and extracted with ethyl acetate (30 mL, 3 times). The organic phase was combined, dried with $Na_2SO_4$, and evaporated under reduced pressure. The resulting residue was recrystallized from EtOAc/hexane to give white crystals (250 mg, 74% yield). $^1$H-NMR (DMSO-d6): 2.99 (d, J=6.4 Hz, 2H, $CH_2COO$); 3.60 (t, J=5.2 Hz, 2H, $CH_2N$); 4.22 (d, J=6.8 Hz, 1H); 4.29 (m, 2H, $CH_2OCO$); 5.55 (m, 2H, CH═CH); 7.33-7.88 (m, 8H, aryl); 7.52 (t, J=5.6 Hz, 1H, NH); 12.24 (s, 1H,OH).

Synthesis of linear product ZG-003. The linear product ZG-003 was synthesized using 9-fluoronylmethoxycarbonyl (Fmoc)-protected amino acids according to standard SPPS protocols. Briefly, the designed linker ZG-002 was loaded to 2-chlorotrityl resin and followed by coupling with Fmoc-Sar-OH, Fmoc-Phe-OH, Fmoc-Val-OH, Fmoc-Ala-OH, Fmoc-D-homoPhe-OH, and mimic FKBD. After the final coupling, the resin was washed with DCM (2 mL, 3 times), DMF (2 mL, 3 times), MeOH (2 mL, 3 times) and dried for 2h. The dry resin was then suspended in a cleavage cocktail solution of acetic acid/trifluoroethanol/DCM (1:1:3, 3 mL) and shaken for 4 h to cleave the linear product from the resin. The resulting solution was collected and concentrated under reduced pressure. Cold ether precipitation of the residue, followed by HPLC purification gave the final product (87% yield). The lyophilized pure product was analyzed by ESI-MS. ESI-MS calculated mass for ZG-003 ($C_{53}H_{67}N_{70}O_{12}$): 993.5, found [M+Na] 1016.4 m/z.

Synthesis of cyclic product ZG-004. The cyclic product ZG-004 was synthesized using ring-closing metathesis reaction. In a microwave tube, ZG-003 (2 mg, 2 μmol) was dissolved in DCE (0.4 mL) and then a solution of Hoveyda- Grubbs $2^{nd}$ generation catalyst (20%) in DCE was added. The reaction was heated in a microwave synthesizer at 120° C. for 30 min. The reaction mixture was purified by HPLC and the lyophilized pure product (46% yield) was analyzed by ESI-MS. ESI-MS calculated mass for ZG-004 ($C_{50}H_{63}N_7O_{10}$): 921.5, found [M+Na] 944.5 m/z.

Example 11

The Design of Rapafucin Library (on Solid Support Beads)-One Bead One Compound (OBOC)

The general structure of rapafucin consist of a) the FKBP-binding domain (FKBD) and b) a peptide chain that cyclizes rapafucin with the FKBD. The solid support beads and the linker in connection with the beads and rapafucin are optional for the ease of selection, synthesis and/or puification. The below figure demonstrates the general structure of rapafucin library on solid support beads. FKBP-binding domain (FKBD) is highlighted in red. AA=amino acid

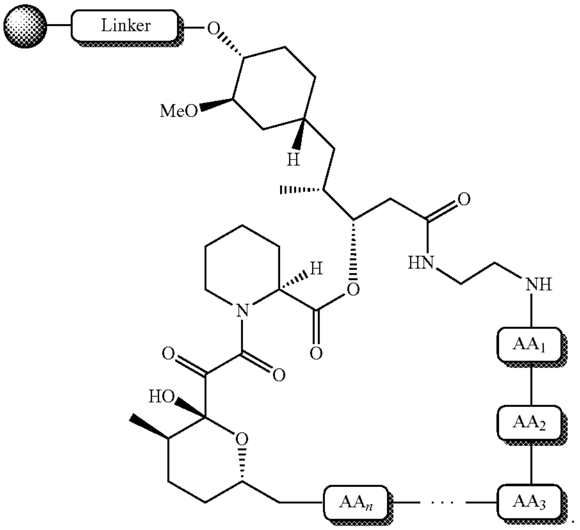

The FKBP-binding domain (FKBD) is obtained either from chemical syntheses or degradation reactions with a natural product which belongs to a group comprising tacrolimus (FK-506) and rapamycin. In one embodiment, FKBD is derived from degradation reactions of rapamycin.

The peptide moiety is covalently attached to the FKBD. These covalent bonds belong to a group comprising alkene group, amide bond and thioether bond. In one embodiment, the covalent bonds are two amide bonds; yet in another embodiment, a thioether bond and an amide bond. The peptide consists of 4 or 5 amino acids ($AA_1$, $AA_2$, $AA_3$, . . . , $AA_n$; n=4 or 5) which selected arbitrarily from the group comprising but not limited to L-alanine, L-valine, L-phenylalanine, L-glycine, L-methionine, L-proline, L-leucine, L-isoleucine, L-tyrosine, L-threonine, L-asparagine, L-ornithine, D-leucine, D-methionine, D-phenylalanine, D-valine, D-homophenylalanine, D-proline, beta-alanine, cyclohexyl-L-alanine, aminoisobutyric acid, 2-aminobenzoic acid, 1-aminocyclohexane carboxylic acid, 4-fluoro-L-phenylalanine, 4-nitro-L-phenylalanine, L-citrulline, sarcosine, N-methyl-L-leucine, N-methyl-L-norleucine, N-methyl-O-benzyl-L-serine, N-methyl-L-phenylalanine, N-methyl-L-alanine, N-methyl-L-isoleucine, N-methyl-L-valine, N-methyl-O-tert-butyl-L-threonine and N-methyl-O-tert-butyl-L-serine.

The hydroxy group on the cyclohexane moiety of the FKBP-binding domain (FKBD) of rapamycin is designed as a chemical handle linked to the solid support beads. The linker belongs to a group comprising silicon-based linker, polyethylene glycol (PEG) and aliphatic (C4-C12) esters. In one embodiment, the linker is a succinate diester. The material of the solid support beads belongs to a group comprising polystyrene (PS), TentaGel, HydroGel and controlled pore glass (CPG). In one embodiment, the matrix material of the solid support beads is polystyrene; yet in another embodiment, TentaGel.

The degradation reactions were carried on a natural product, rapamycin based on published protocol. The carboxyl group on the TBS protected FKBD 2 was coupled to Fmoc protected ethylenediamine in the presence of a coupling reagent (selected from a group comprising DCC, EDCI, HBTU, HATU) and a non-nucleophilic base. In one embodiment, EDCI and DIPEA were used as the reagents to synthesize intermediate 3. This reaction was carried at <10° C. for minimizing the side-reactions. In one embodiment, the reaction temperature was 0° C. Upon silica-gel column purification, the material was treated with HCl in an organic/aqueous solvent mixture. In one embodiment, a solvent mixture of THF/$H_2O$ (v/v)=4/1 was chosen. Once the selectively deprotected FKBD 4 was obtained and purified by column chromatography, the material was then co-heated with catalytic amount (10 mol %) of DMAP in pyridine. The optimal condition of the reaction was stirring at 45° C. for 16 hours. The resulting carboxylic acid 5 was subsequentially purified by a silica-gel column and a reverse phase HPLC column. H-NMR of compound 5 was measured to verify the purity of the compound.

Anhydrous intermediate 5 was coupled to a trityl chloride-modified solid support in the presence of DIPEA in dichloromethane. In one embodiment, a commercially available polystyrene trityl chloride resin was used; yet in another embodiment, a TentaGel trityl hydroxide resin was used upon being activated with thionyl chloride. The loading of compound 5 on solid support is controlled stoichiometrily at 0.10-1.0 mmol/g before quenched by DIPEA (5%) in methanol.

Example 12

Synthesis of FKBD Moiety of Rapafucin on Solid Support Beads

The synthesis of FKBD moiety of rapafucin on solid support beads is shown below in Scheme 12.

Scheme 12
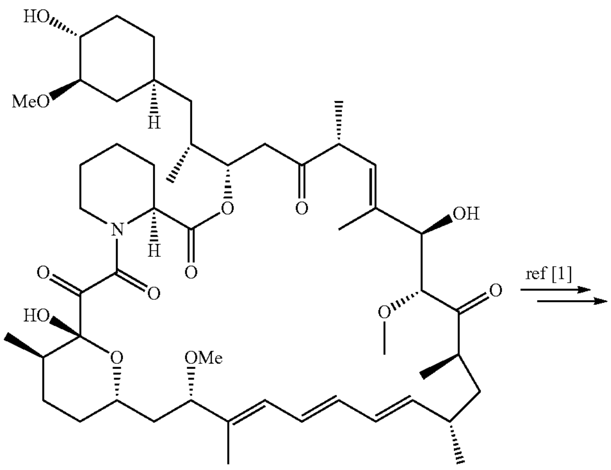
rapamycin (1)
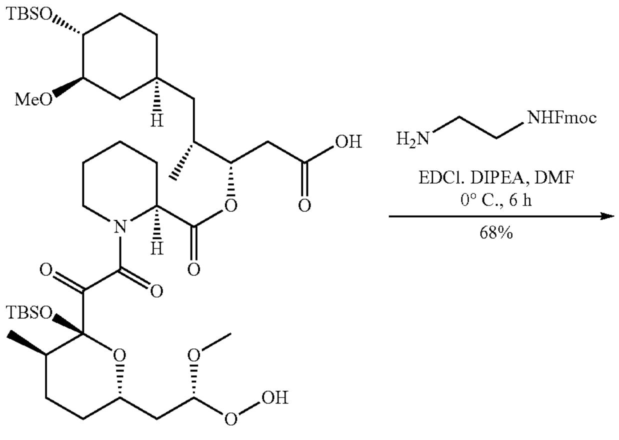
2
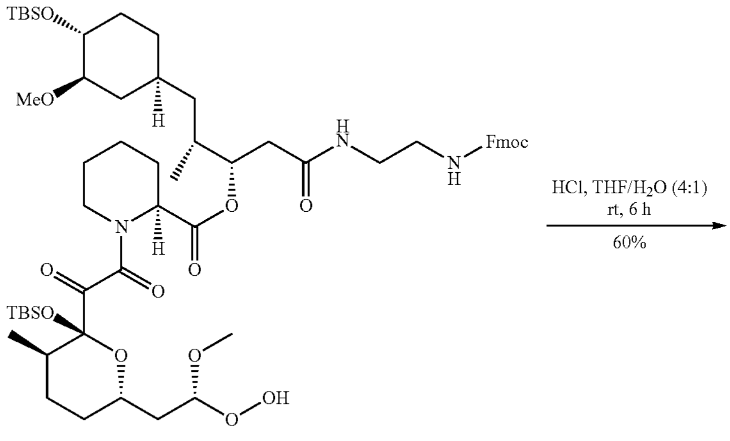
3

-continued

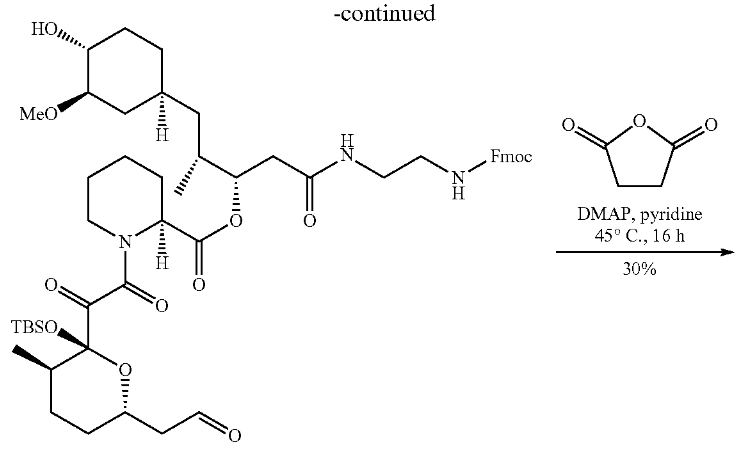

4

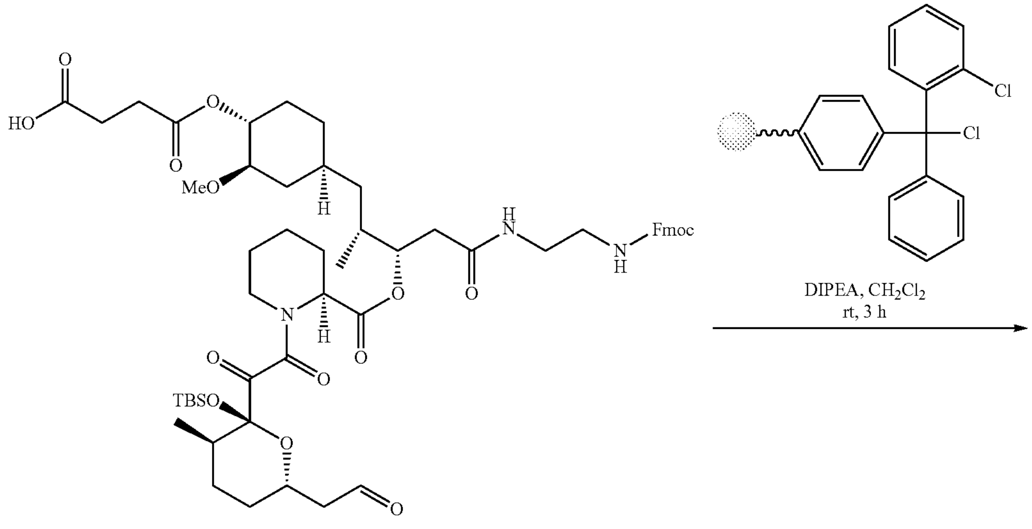

5

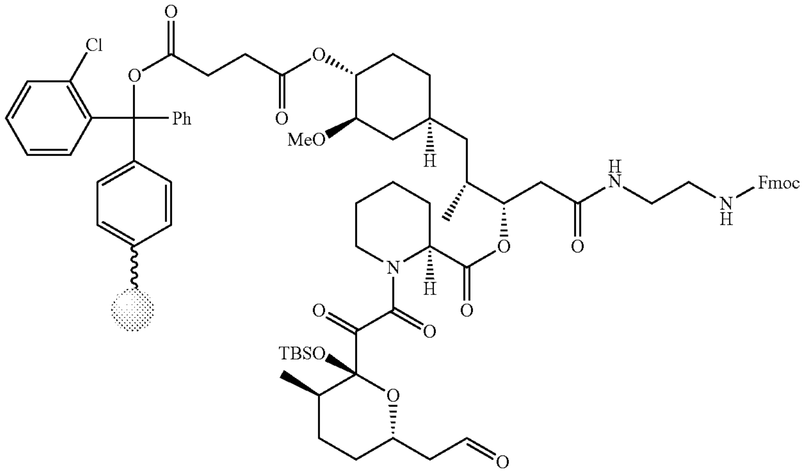

6

With key intermediate 6 on the resin at hand, standard peptide synthesis on solid support was conducted for all analogs of rapafucin. By repeating steps a (cleavage of N-terminus protecting group) and b (coupling of the N-terminus with a new carboxyl group) (Scheme 2), the peptide chain was elongated to 4-5 amino acids to yield intermediate 8. Two strategies were explored to cyclize the linear rapafucin 8.

For strategy 1, a sulfur-iodo displacement reaction was applied (Scheme 2). Upon coupling of an S-protected 2-mercaptoacetic acid to the N-terminus of intermediate 8 with standard protocol, the aldehyde group on the tetrahydropyran moiety of FKBD was reduced to a hydroxy group, which is able to be converted to an iodo group later on. The macrocycle is formed in a cascade manner after 9-methylene-9H-fluorene group is cleaved by piperidine (Scheme 2). The rapafucin analog 11 are finalized by deprotecting TBS group with TBAF at 0° C. Higher temperature or higher concentration may lead to a nucleophilic cleavage of the ester bond on FKBD. Rapafucins 14-16 were synthesized on strategy 1 with a yield of 4-5%.

For strategy 2, a lactam formation strategy was implemented as shown below in Schemes 13-15.

Scheme 13

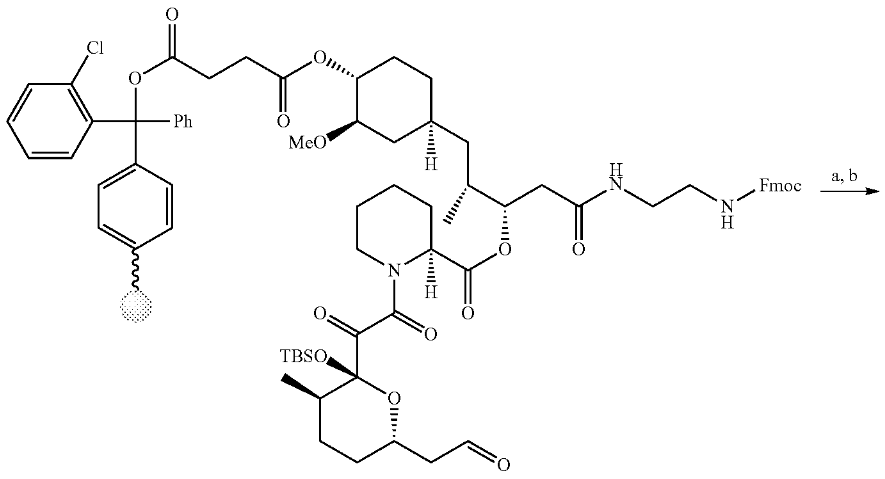

6

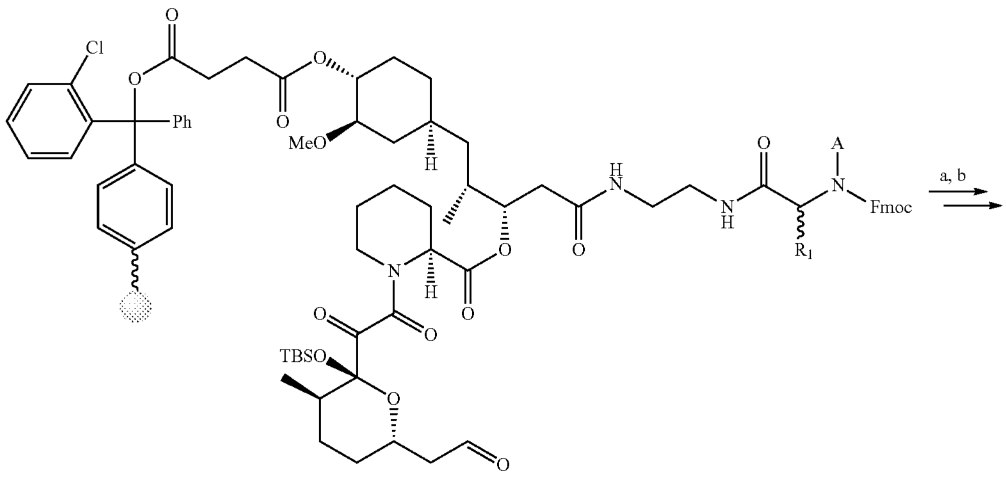

7

-continued

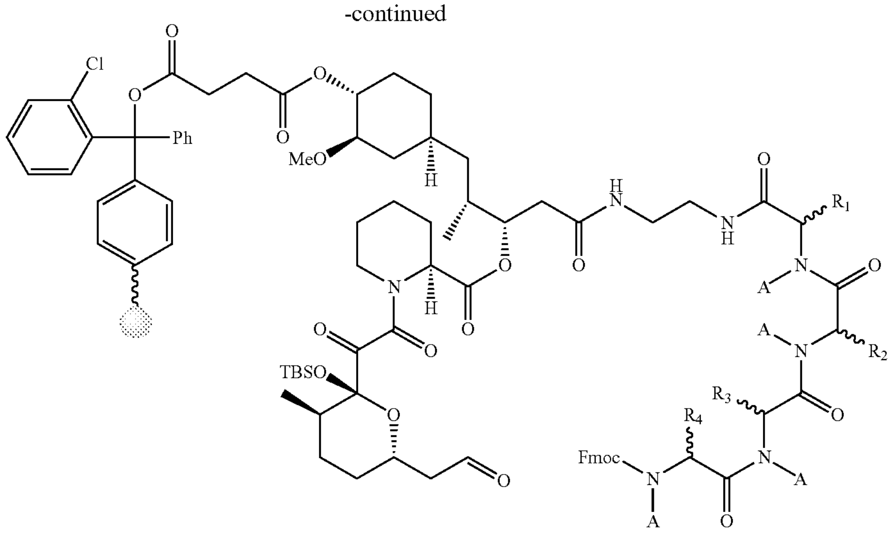

8

Peptide synthesis/cyclization of rapafucin. Conditions: a) 20% piperidine, DMF, room temperature, 0.2-2 h; b)N-Fmoc protected amino acid, HATU, DIPEA, DMF, room temperature, 1-3 h; c) t-$BuNH_2$—$BH_3$, $CH_2Cl_2$, room temperature, 20 min; d) $Me(PhO)_3PI$, 2,6-lutidine, DMF, room temperature, 20 min; e) TBAF (0.10 mM), THF, 0° C., 1-2 h; f) oxone, DMF, room temperature, 16 h; g) PyBop, HOAt, DIPEA, DMF, room temperature, 3 h. A=Me or H is highlighted in red.

Scheme 14

Strategy 1

8

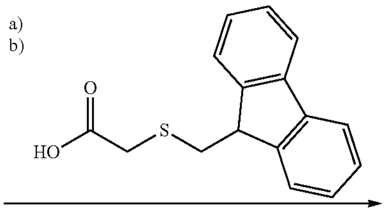

-continued
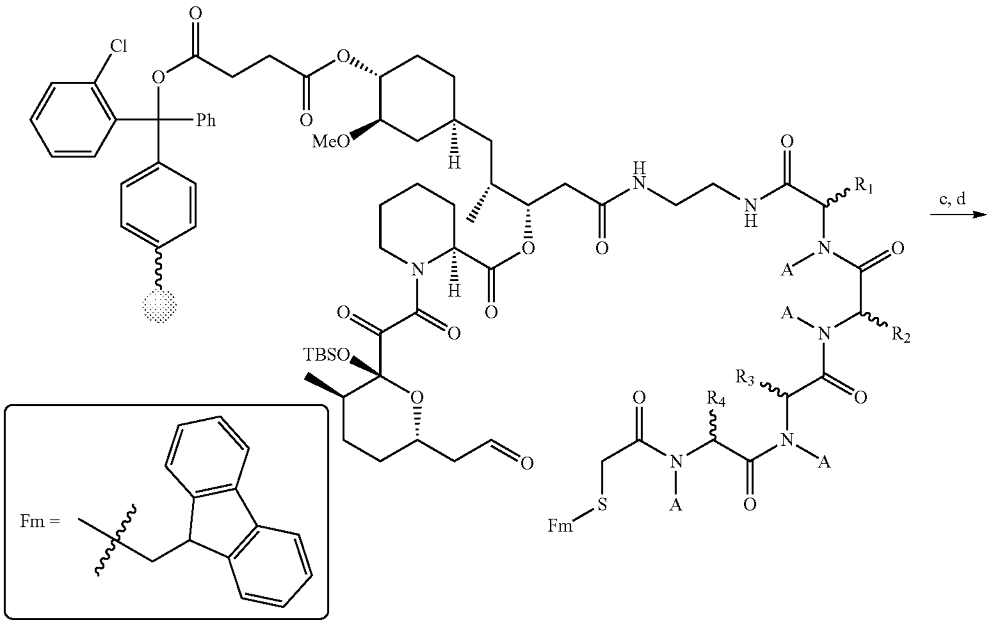
9
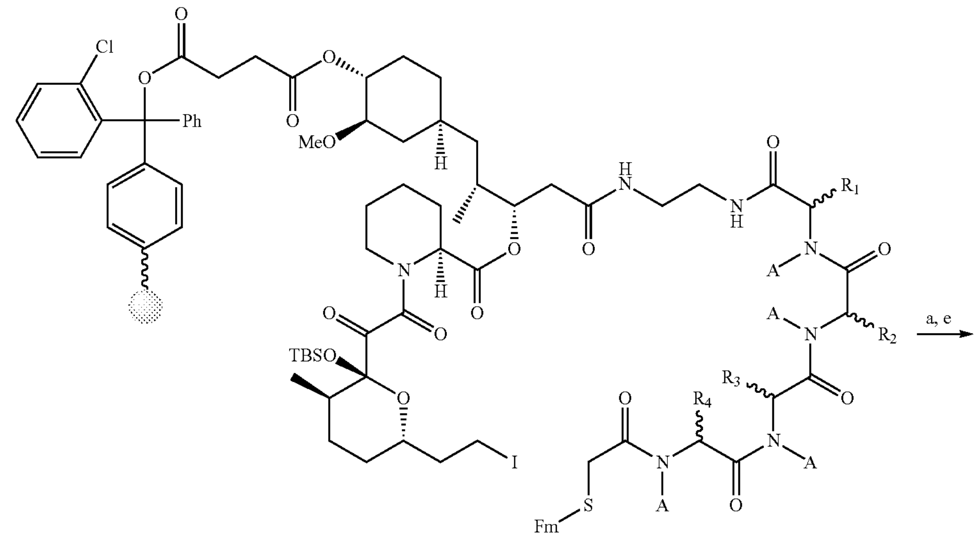
10

-continued
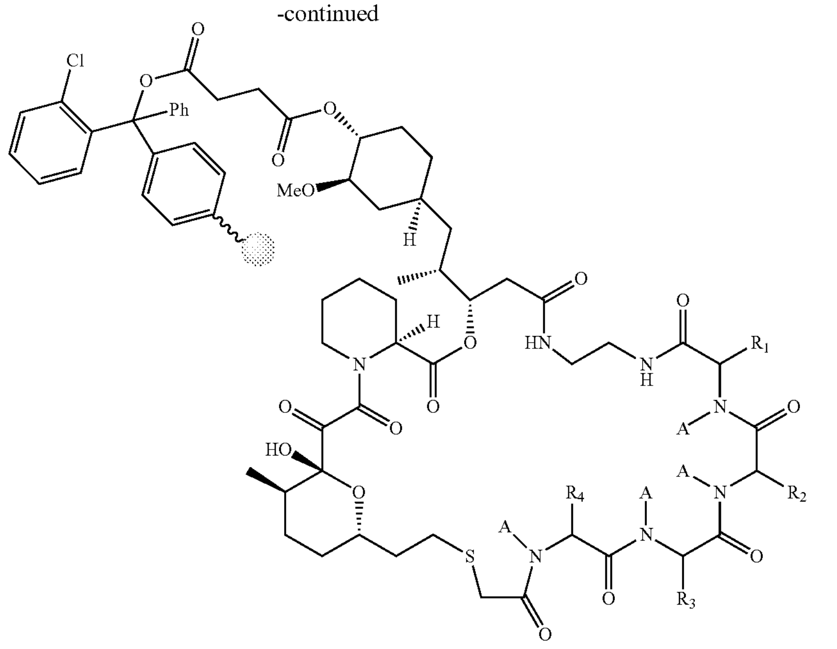
11
Scheme 15
Strategy 2
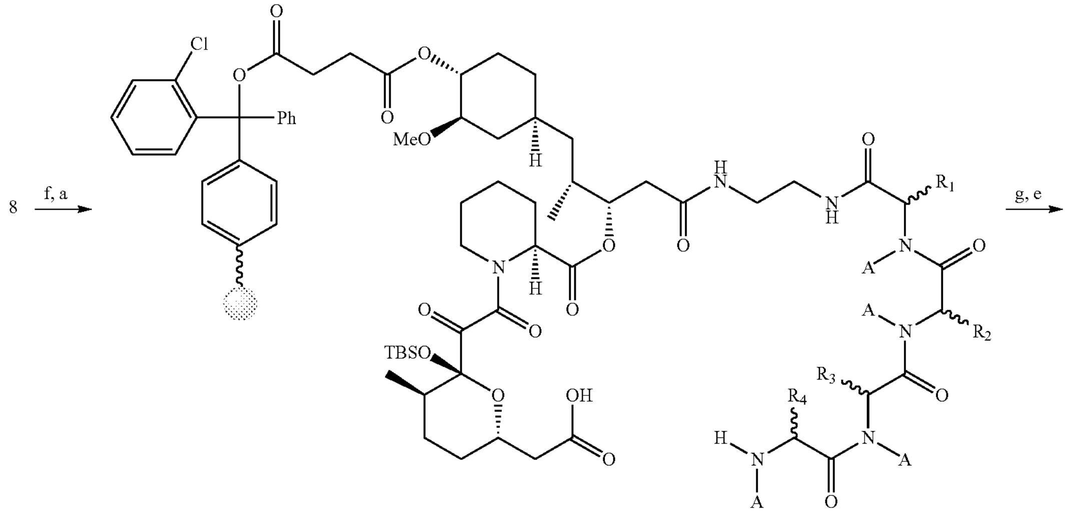
12

-continued

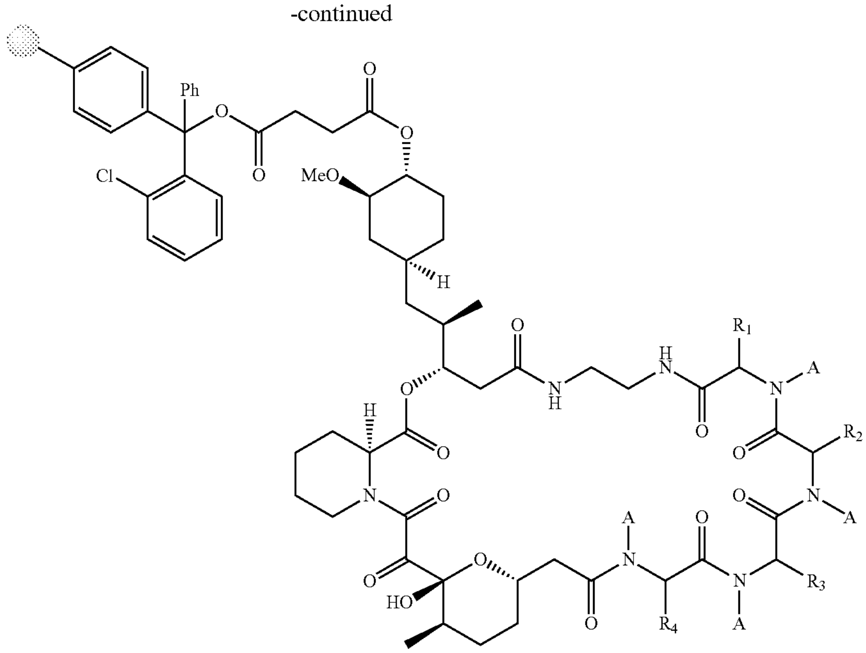

13

The above-mentioned aldehyde group was herein oxidized into a carboxyl group before the N-terminus amine was deprotected by standard protocol. The linear amino acid 12 was then treated with macrolactamization coupling reagent (e.g., PyBop/HOAt/DIPEA), and finalized with TBAF deprotection of the TBS group to give rapafucin analog 13. Rapafucins 17-19 were synthesized on strategy 1 with a yield of 4-30% as shown below in Scheme 16.

Scheme 16

14

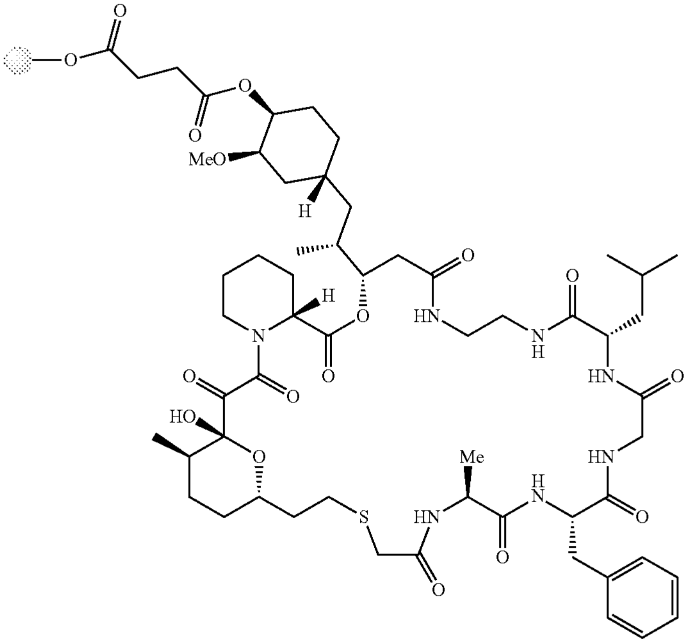

-continued
15
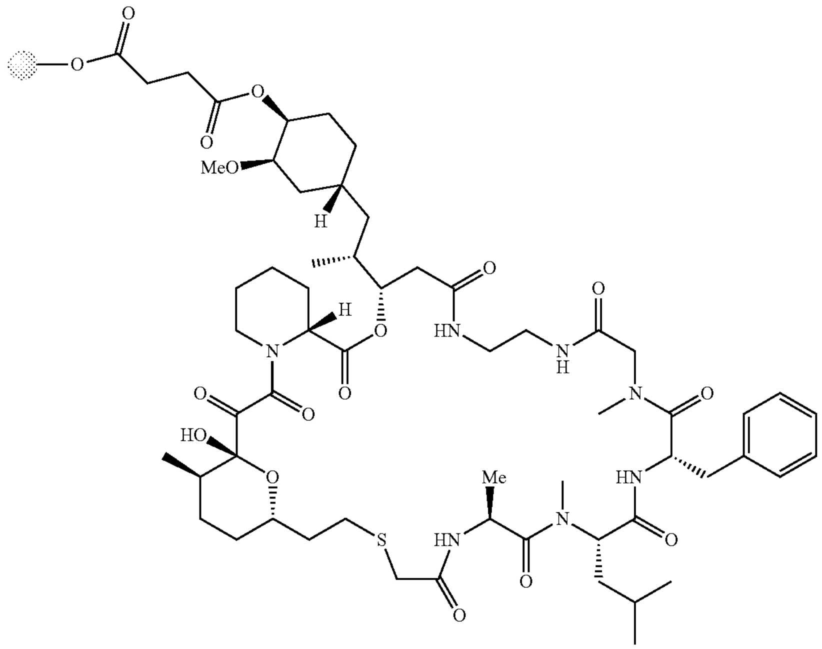
16
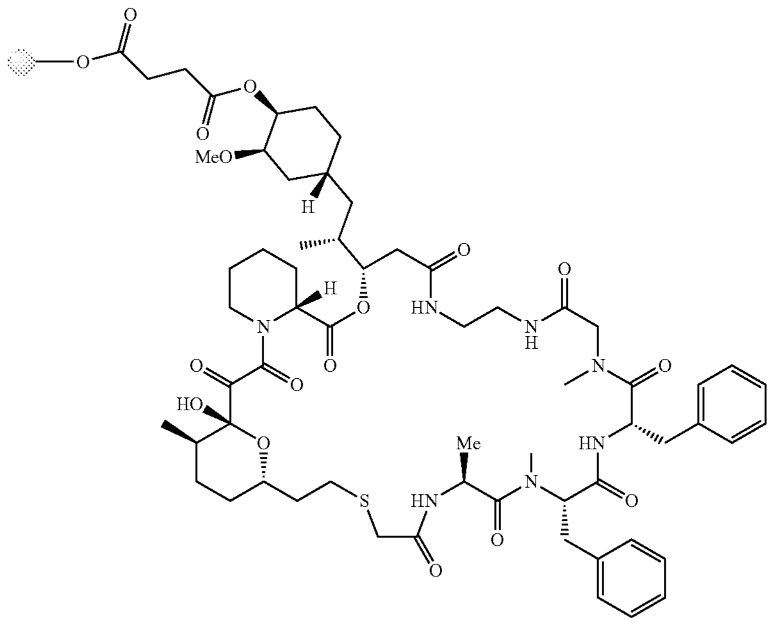

-continued
17
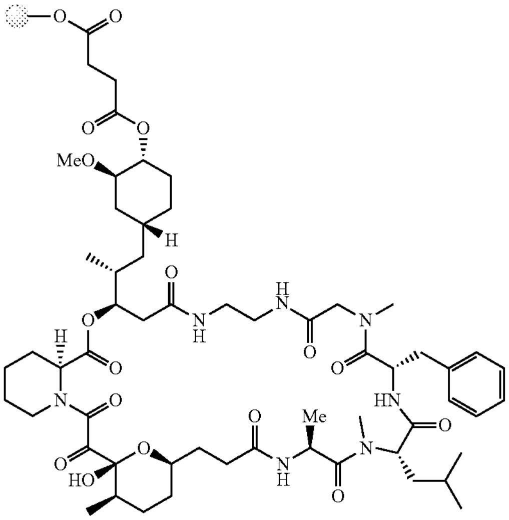
18
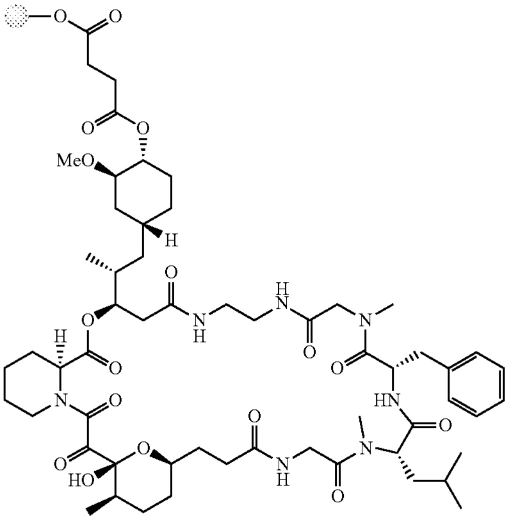
19
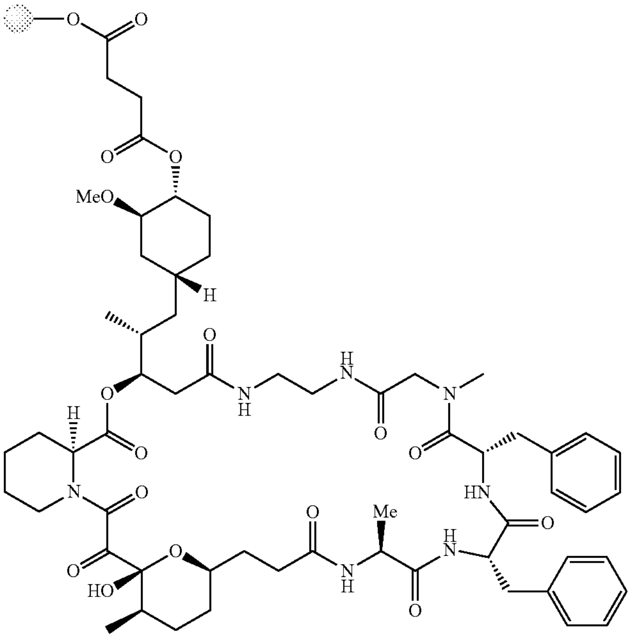

Compound 3

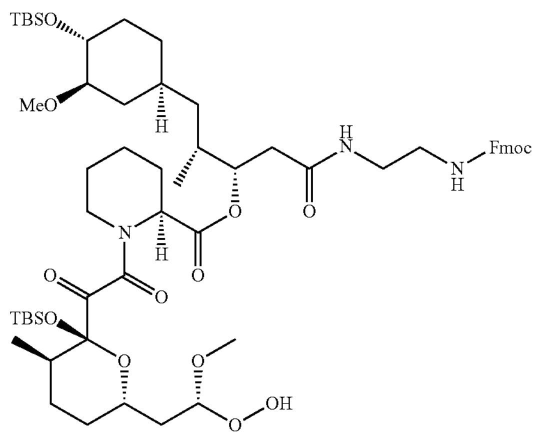

Compound 2 (0.45 g) was prepared by adding EDCI-HCl (128 mg) and DIPEA (333 μL) in DMF (15 mL) at 0° C. for 10 minutes before adding Fmoc-ethylenediamine HCl salt (185 mg) in DMF (2 mL). The resulting solution was stirred at 0° C. for 3 hours and quenched by the addition of HCl (5% aqueous solution, 10 mL). The reaction mixture was diluted with 30 mL EtOAc and poured into a separatory funnel. The organic layer was subsequentially washed with HCl (5% aqueous solution, 30 mL×3) and dried over $Na_2SO_4$ before being concentrated in vacuo. The crude product was purified by silica-gel column chromatography eluting with MeOH in $CH_2Cl_2$ (2-5%). 294 mg product (68%) was obtained as a yellow solid.

Although the invention has been described with reference to the above example, it may be understood that modifications and variations are encompassed within the spirit and scope of the invention. Accordingly, the invention is limited only by the following claims.

What is claimed is:

1. A method of treating a hyperproliferative disorder in a patient in need thereof comprising: administering a therapeutically effective amount of a compound of Formula I (I)

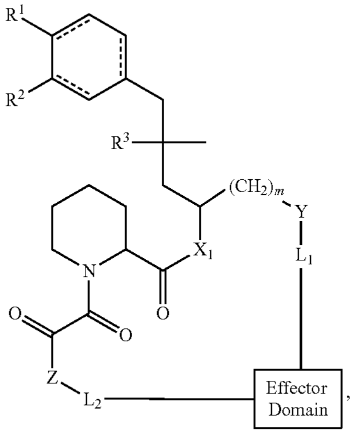

or a pharmaceutically acceptable salt or solvate thereof, to the patient, thereby treating the disorder;

wherein:

------- is a single or double bond;

$X_1$ is O or $NR^6$;

Y is —C(O)—

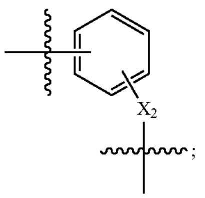

$X_2$ is $(CH_2)_m$, O, or $NR^6$;

Z is

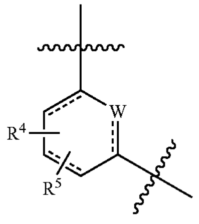

or

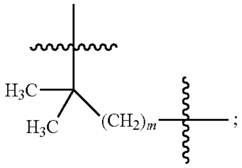

;

W is O, CH, $CH_2$, $CR^4$, or $CR^5$;

$L_1$ and $L_2$ are each independently a direct bond, substituted or unsubstituted —($C_1$-$C_6$)alkyl-, substituted or unsubstituted —$(CH_2)_n$O($C_1$-$C_6$)alkyl-, substituted or unsubstituted —$(CH_2)_n$C(O)—, substituted or unsubstituted —$(CH_2)_n$C(O)($C_1$-$C_6$)alkyl-, substituted or unsubstituted —$(CH_2)_n$C(O)O($C_1$-$C_6$)alkyl-, substituted or unsubstituted —$(CH_2)_n$NH($C_1$-$C_6$)alkyl-, substituted or unsubstituted —$(CH_2)_n$C(O)NH($C_1$-$C_6$)alkyl-, substituted or unsubstituted —$(CH_2)_n$S($C_1$-$C_6$)alkyl-, substituted or unsubstituted —$(CH_2)_n$C(O)$(CH_2)_n$S($C_1$-$C_6$)alkyl-, substituted or unsubstituted —($C_2$-$C_6$)alkenyl-, substituted or unsubstituted —$(CH_2)_n$O($C_2$-$C_6$)alkenyl-, substituted or unsubstituted —$(CH_2)_n$C(O)($C_2$-$C_6$)alkenyl-, substituted or unsubstituted —$(CH_2)_n$C(O)O($C_2$-$C_6$)alkenyl-, substituted or unsubstituted —$(CH_2)_n$NH($C_1$-$C_6$)alkenyl-, substituted or unsubstituted —$(CH_2)_n$C(O)NH($C_2$-$C_6$)alkenyl-, substituted or unsubstituted —$(CH_2)_n$S($C_2$-$C_6$)alkenyl-, substituted or unsubstituted —$(CH_2)_n$C(O)$(CH_2)_n$S($C_2$-$C_6$)alkenyl-, substituted or unsubstituted —($C_2$-$C_6$)alkynyl-, substituted or unsubstituted —$(CH_2)_n$O($C_2$-$C_6$)alkynyl-, substituted or unsubstituted —$(CH_2)_n$C(O)($C_2$-$C_6$)alkynyl-, substituted or unsubstituted —$(CH_2)_n$C(O)O($C_2$-$C_6$)alkynyl-, substituted or unsubstituted —$(CH_2)_n$NH($C_1$-$C_6$)alkynyl-, substituted or unsubstituted —$(CH_2)_n$C(O)NH($C_2$-$C_6$)alkynyl-, substituted or unsubstituted —$(CH_2)_n$S($C_2$-$C_6$)alkynyl-, substituted or unsubstituted —$(CH_2)_n$C(O)$(CH_2)_n$S($C_2$-$C_6$)alkynyl-, wherein each alkyl, alkenyl and alkynyl group may be optionally substituted with alkyl, alkoxy, amino, carboxyl, cyano, nitro, or trifluoromethyl;

each m is independently an integer selected from 0, 1, 2, 3, 4, 5, and 6;

each n is independently an integer selected from 0, 1, 2, 3, 4, 5, and 6;

$R^1$ is hydrogen, hydroxyl, or OPG, wherein PG is a protecting group, or $R^1$

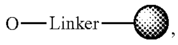, wherein

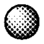

is a resin;

$R^2$ is hydrogen, hydroxyl, or alkoxy;

$R^3$ is hydrogen or alkyl;

$R^4$ and $R^5$ are each independently hydrogen, hydroxy, alkyl, alkoxy, or OPG, wherein PG is a protecting group;

$R^6$ is hydrogen or alkyl;

wherein the Effector Domain has Formula II:

(II)

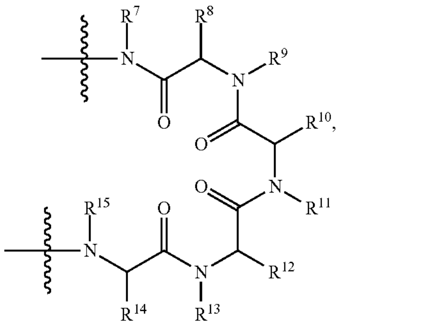

wherein:

$R^7$, $R^9$, $R^{11}$, $R^{13}$, and $R^{15}$ are each independently hydrogen or alkyl;

$R^8$, $R^{10}$, $R^{12}$, and $R^{14}$ are each independently hydrogen, halogen, amino, cyano, nitro, trifluoromethyl, substituted or unsubstituted alkyl, substituted or unsubstituted alkenyl, substituted or unsubstituted alkynyl, substituted or unsubstituted cycloalkyl, substituted or unsubstituted perfluoroalkyl, substituted or unsubstituted alkoxy, substituted or unsubstituted alkylamino, substituted or unsubstituted alkylthio, substituted or unsubstituted aryl, substituted or unsubstituted alkylaryl, substituted or unsubstituted heteroalkyl, substituted or unsubstituted heterocycloalkyl, substituted or unsubstituted heteroaryl, substituted or unsubstituted heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)OR^{16}$, $(CH_2)_nOC(O)R^{16}$, $(CH_2)_nNR^{17}R^{18}$, $(CH_2)_nC(O)NR^{17}R^{18}$, $(CH_2)_nN^{19}RC(O)R^{16}$, $(CH_2)_nN^{19}RC(O)OR^{16}$, $(CH_2)_nNR^{19}C(O)NR^{17}R^{18}$, $(CH_2)_nSR^{16}$, $(CH_2)_nS(O)_jNR^{17}R^{18}$, $(CH_2)_nN^{19}RS(O)_jR^{16}$, or $—(CH_2)_nNR^{19}S(O)_jNR^{17}R^{18}$, n is an integer selected from 0, 1, 2, 3, 4, 5, and 6;

j is an integer selected from 0, 1, and 2;

$R^{16}$, $R^{17}$, $R^{18}$, and $R^{19}$ are each independently hydrogen, halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, or heteroalkylaryl, or $R^{16}$ and $R^{19}$ are as described above, and $R^{17}$ and $R^{18}$, together with the N atom to which they are attached, form a substituted or unsubstituted 5-, 6-, or 7-membered heterocycloalkyl or a substituted or unsubstituted 5-membered heteroaryl, wherein each of the above groups listed for $R^8$, $R^{10}$, $R^{12}$, and $R^{14}$ may be optionally independently substituted with 1 to 3 groups selected from halogen, amino, cyano, nitro, trifluoromethyl, alkyl, alkenyl, alkynyl, cycloalkyl, perfluoroalkyl, alkoxy, alkylamino, alkylthio, aryl, alkylaryl, heteroalkyl, heterocycloalkyl, heteroaryl, heteroalkylaryl, $(CH_2)_nCN$, $(CH_2)_nCF_3$, $(CH_2)_nC_2F_5$, $(CH_2)_nOR^{16}$, $(CH_2)_nC(O)R^{16}$, $(CH_2)_nC(O)$ $OR^{16}$, $(CH_2)_nOC(O)R^{16}$, $(CH_2)_nNR^{17}R^{18}$, $(CH_2)_nC(O)NR^{17}R^{18}$, $(CH_2)_nN^{19}RC(O)R^{16}$, $(CH_2)_nN^{19}RC(O)$ $OR^{16}$, $(CH_2)_nNR^{16}C(O)NR^{17}R^{18}$, $(CH_2)_nSR^{16}$, $(CH_2)_nS(O)_jNR^{17}R^{18}$, $(CH_2)_nN^{19}RS(O)_jR^{16}$, and $—(CH_2)_nNR^{19}S(O)_jNR^{17}R^{18}$.

2. The method of claim 1, wherein:

X is O or $NR^6$;

$L_1$ and $L_2$ are each independently $—(C_1\text{-}C_6)alkyl\text{-}$, $—(CH_2)_nO(C_1\text{-}C_6)alkyl\text{-}$, $—(CH_2)_nC(O)(C_1\text{-}C_6)alkyl\text{-}$, $—(CH_2)_nC(O)O(C_1\text{-}C_6)alkyl\text{-}$, $—(CH_2)_nNH(C_1\text{-}C_6)alkyl\text{-}$, $—(CH_2)_nC(O)NH(C_1\text{-}C_6)alkyl\text{-}$, $—(CH_2)_nS(C_1\text{-}C_6)alkyl\text{-}$, $—(CH_2)_nC(O)(CH_2)_nS(C_1\text{-}C_6)alkyl\text{-}$, $—(C_2\text{-}C_6)alkenyl\text{-}$, $—(CH_2)_nO(C_2\text{-}C_6)alkenyl\text{-}$, $—(CH_2)_nC(O)(C_2\text{-}C_6)alkenyl\text{-}$, $—(CH_2)_nC(O)O(C_2\text{-}C_6)alkenyl\text{-}$, $—(CH_2)_nNH(C_1\text{-}C_6)alkenyl\text{-}$, $—(CH_2)_nC(O)NH(C_2\text{-}C_6)alkenyl\text{-}$, $—(CH_2)_nS(C_2\text{-}C_6)alkenyl\text{-}$, $—(CH_2)_nC(O)(CH_2)_nS(C_2\text{-}C_6)alkenyl\text{-}$, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl, or OPG, wherein PG is a silyl protecting group, or $R^1$ is

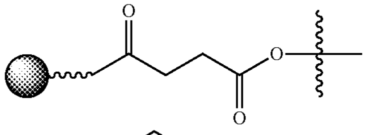

or

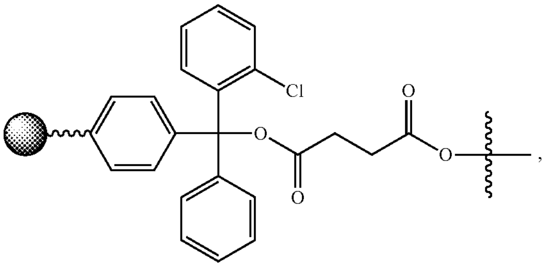, wherein

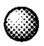

is a resin;

$R^2$ is hydroxyl or alkoxy;

$R^3$ is hydrogen or alkyl;

$R^4$ and $R^5$ are each independently hydrogen, alkyl, alkoxy, or OPG, wherein PG is a silyl protecting group;

$R^6$ is hydrogen;

$R^7$, $R^9$, $R^{11}$, $R^{13}$, and $R^{15}$ are each independently hydrogen or $CH_3$;

$R^8$, $R^{10}$, $R^{12}$, and $R^{14}$ are each independently substituted or unsubstituted cyclopropyl, substituted or unsubstituted cyclobutyl, substituted or unsubstituted cyclopentyl, substituted or unsubstituted cyclohexyl, substituted or unsubstituted cycloheptyl, or substituted or unsubstituted cyclooctyl; or $R^8$, $R^{10}$, $R^{12}$, and $R^{14}$ are each independently substituted or unsubstituted tetrahydrofuranyl, substituted or unsubstituted tetrahydrothiophenyl, substituted or unsubstituted pyrrolidinyl, substituted or unsubstituted 1,3-dioxolanyl, substituted or unsubstituted pyrazolidinyl, substituted or unsubstituted imidazolidinyl, substituted or unsubstituted 1,4-dioxanyl, substituted or unsubstituted piperidinyl, substituted or unsubstituted piperazinyl, substituted or unsubstituted morpholinyl, substituted or unsubstituted thiomorpholinyl, or substituted or unsubstituted 1,4-dithianyl; or $R^8$, $R^{10}$, $R^{12}$, and $R^{14}$ are each independently substituted or unsubstituted phenyl, substituted or unsubstituted benzyl, substituted or unsubstituted naphthylenyl, or substituted or unsubstituted biphenyl; or $R^8$, $R^{10}$, $R^{12}$, and $R^{14}$ are each independently substituted or unsubstituted furanyl, substituted or unsubstituted thiophenyl, substituted or unsubstituted pyrrolyl, substituted or unsubstituted pyrazolyl, substituted or unsubstituted imidazolyl, substituted or unsubstituted triazolyl, substituted or unsubstituted isoxazolyl, substituted or unsubstituted oxazolyl, substituted or unsubstituted thiazolyl, substituted or unsubstituted isothiazolyl, substituted or unsubstituted pyridinyl, substituted or unsubstituted pyridizanyl, substituted or unsubstituted pyrimidinyl, substituted or unsubstituted triazinyl, substituted or unsubstituted benzofuranyl, substituted or unsubstituted benzo(b)thiophenyl, substituted or unsubstituted indolyl, substituted or unsubstituted benzimidazolyl, substituted or unsubstituted indazolyl, substituted or unsubstituted benzisoxazolyl, substituted or unsubstituted benzoxazolyl, substituted or unsubstituted benzothiazolyl, substituted or unsubstituted quinolinyl, substituted or unsubstituted isoquinolinyl, substituted or unsubstituted quinazolinyl, substituted or unsubstituted quinoxalinyl, or substituted or unsubstituted naphthyridinyl.

3. The method of claim 1, wherein:

$L_1$ and $L_2$ are each independently $—(C_1\text{-}C_6)$alkyl-, $—(CH_2)_nO(C_1\text{-}C_6)$alkyl-, $—(CH_2)_nC(O)(C_1\text{-}C_6)$alkyl-, $—(CH_2)_nNH(C_1\text{-}C_6)$alkyl-, $—(CH_2)_nC(O)NH(C_1\text{-}C_6)$alkyl-, $—(C_2\text{-}C_6)$alkenyl-, $—(CH_2)_nO(C_2\text{-}C_6)$alkenyl-, $—(CH_2)_nC(O)(C_2\text{-}C_6)$alkenyl-, $—(CH_2)_nNH(C_1\text{-}C_6)$alkenyl-, $—(CH_2)_nC(O)$ $NH(C_2\text{-}C_6)$alkenyl-, wherein each alkyl and alkenyl group may be substituted with alkyl, alkoxy, or carboxyl;

n is an integer selected from 0, 1, 2, 3, 4, 5, and 6;

$R^1$ is hydrogen, hydroxyl or OPG, wherein PG is a tert-butyldimethylsilyl protecting group, or $R^1$ is

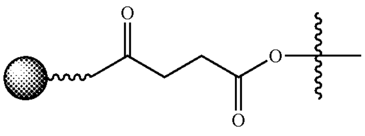

or

-continued

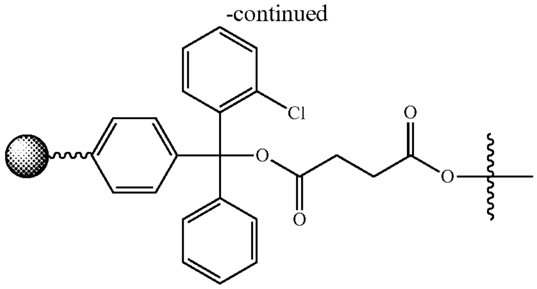

, wherein

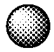

is Wang resin;

$R^4$ and $R^5$ are each independently hydrogen, hydroxy, alkyl, alkoxy, or OPG, wherein PG is a tert-butyldimethylsilyl protecting group;

$R^7$, $R^9$, $R^{11}$, $R^{13}$, and $R^{15}$ are each independently hydrogen;

$R^8$, $R^{10}$, $R^{12}$, and $R^{14}$ are each independently hydrogen, substituted or unsubstituted alkyl, substituted or unsubstituted benzyl, substituted or unsubstituted pyrrolidinyl, substituted or unsubstituted indolyl, $(CH_2)_nOR^5$, $(CH_2)_nC(O)NR^6R^7$, or $(CH_2)_nSR^5$; and $R^{16}$, $R^{17}$, and $R^{18}$ are each independently hydrogen or $(C_1\text{-}C_6)$alkyl.

4. The method of claim 1, wherein:

$L_1$ and $L_2$ are each independently $—(C_1\text{-}C_6)$alkyl-, $—O(C_1\text{-}C_6)$alkyl-, $—C(O)(C_1\text{-}C_6)$alkyl-, $—(CH_2)_nC(O)NH(C_1\text{-}C_6)$alkyl-, $—(C_2\text{-}C_6)$alkenyl-, $—O(C_2\text{-}C_6)$alkenyl-, $—C(O)(C_2\text{-}C_6)$alkenyl-, $—(CH_2)_nC(O)NH(C_2\text{-}C_6)$alkenyl-, wherein each alkyl and alkenyl group may be substituted with alkyl, alkoxy, or carboxyl;

n is an integer selected from 0, 1, 2, 3, 4, 5, and 6;

$R^8$, $R^{10}$, $R^{12}$, and $R^{14}$ are each independently H, $CH_3$, $CH_2OH$, $CH_2SH$, $CH(OH)CH_3$, $CH_2C(O)NH_2$, $CH_2CH_2C(O)NH_2$, $CH_2CH_2SCH_3$, $CH_2CH(CH_3)_2$, $CH(CH_3)CH_2CH_3$, $CH_2C_6C_5$,

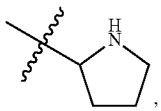

,

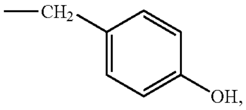

or

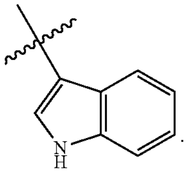

.

5. The method of claim 1, wherein:

$L_1$ and $L_2$ are each independently $—OCH_2CH_2—$, $—CH_2C(O)—$, $—CH_2CH_2C(O)—$, $—C(O)NHCH_2CH_2$, $—CH_2CH{=}CHCH_2—$, $—OCH_2CH{=}CHCH_2CH_2—$, $—OCH_2CH{=}CHCH_2CH(CO_2H)—$, $—CH_2C(O)NHCH_2CH_2—$, or $CH_2CH(OCH_3){=}C(CH_3)\ CH_2CH_2$; and $R^8$, $R^{10}$, $R^{12}$, and $R^{14}$ are each independently the side-chain of the amino acid alanine, asparagine, cysteine, glutamine, glycine, isoleucine, leucine, methionine, phenylalanine, proline, serine, threonine, tryptophan, tyrosine, or valine.
6. The method of claim 1, wherein the compound has Formulae II, III, IV, V, or VI:
(II)
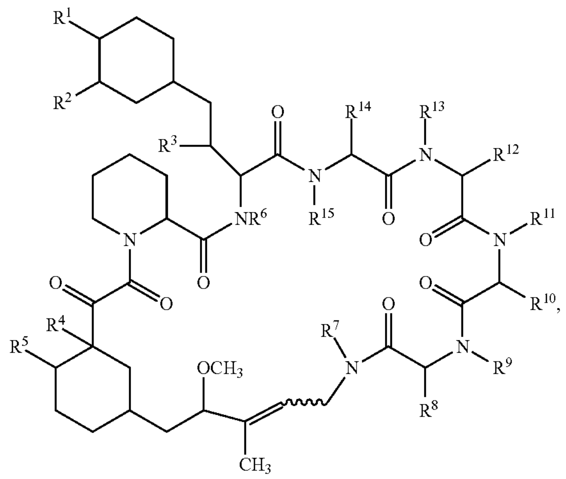
(III)
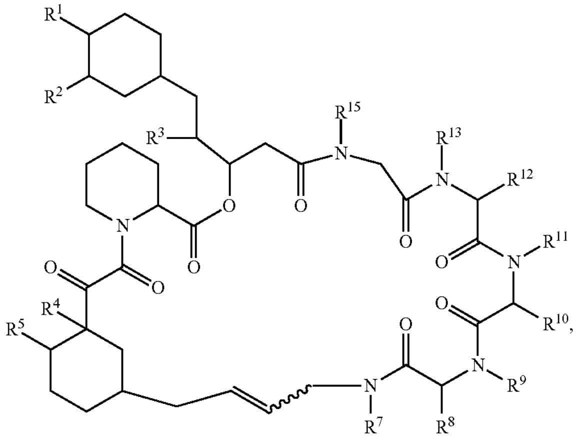
-continued
(IV)
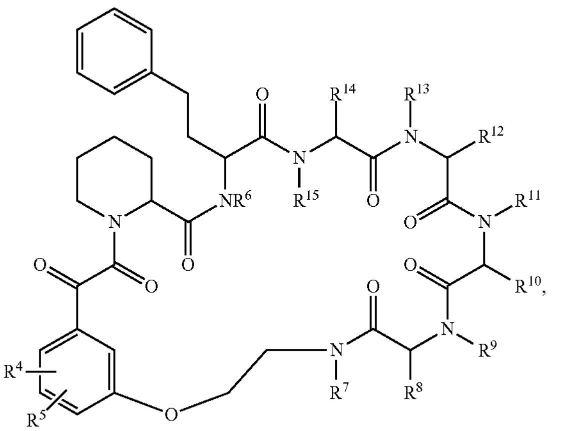
(V)
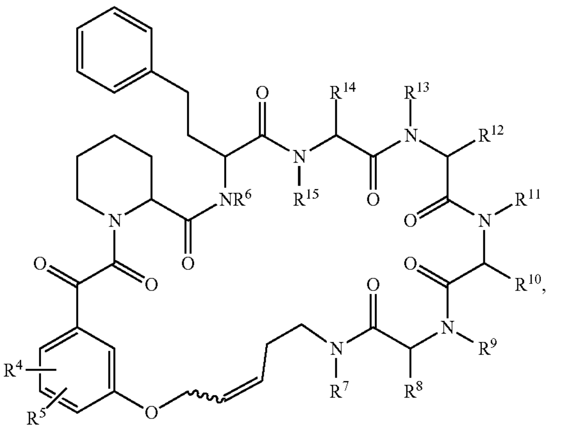
(VI)
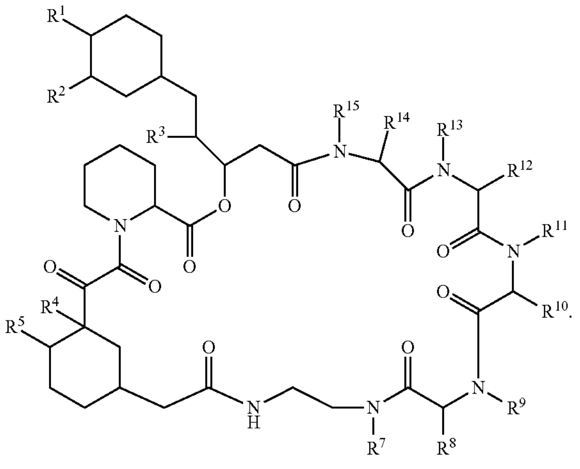

7. The method of claim 1, wherein the compound has Formulae VII, VIII, IX, or X:
(VII)
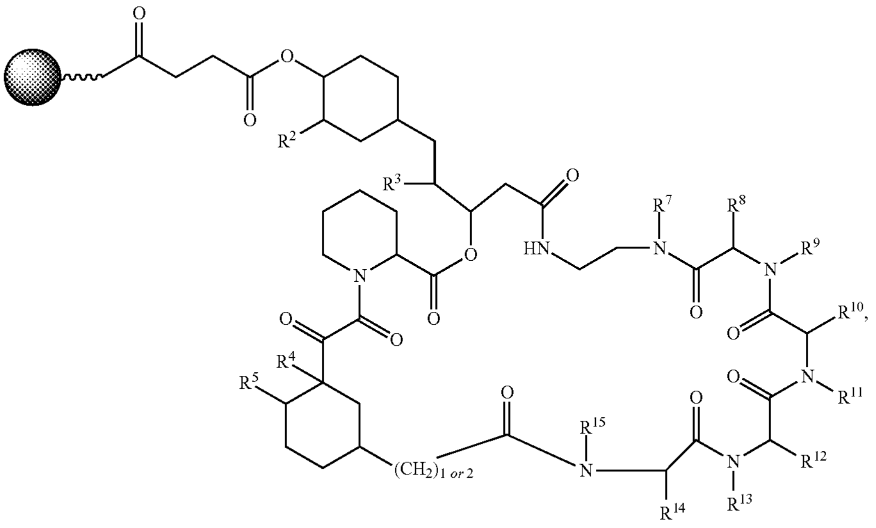
(VIII)
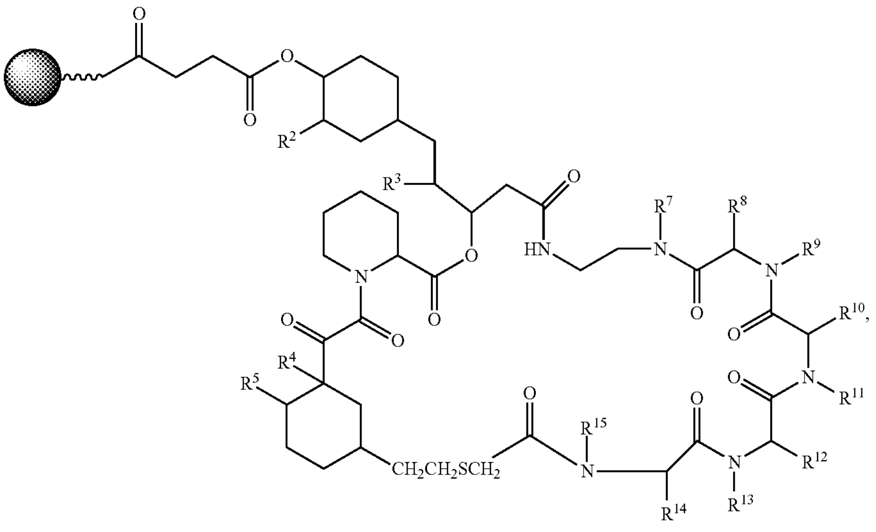

-continued (IX)

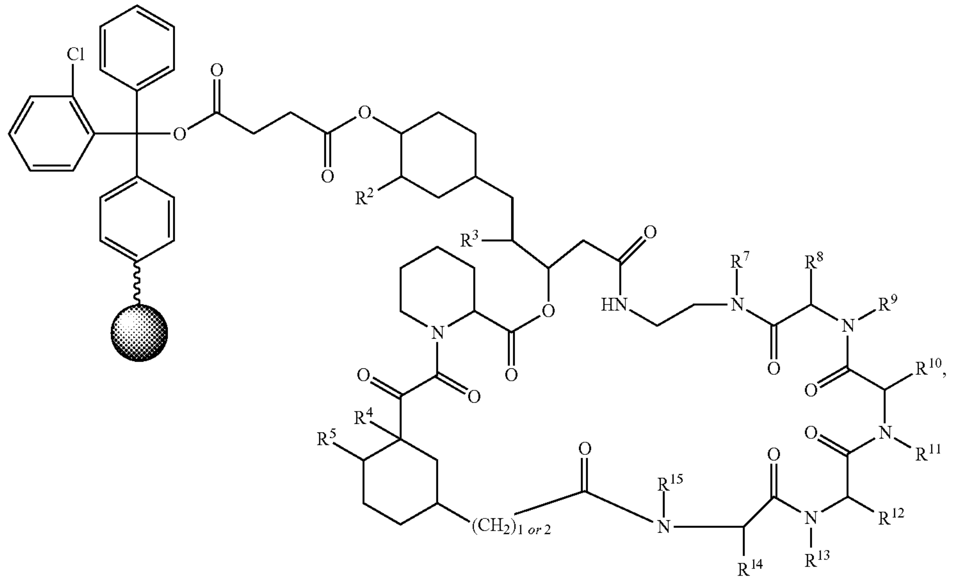

(X)

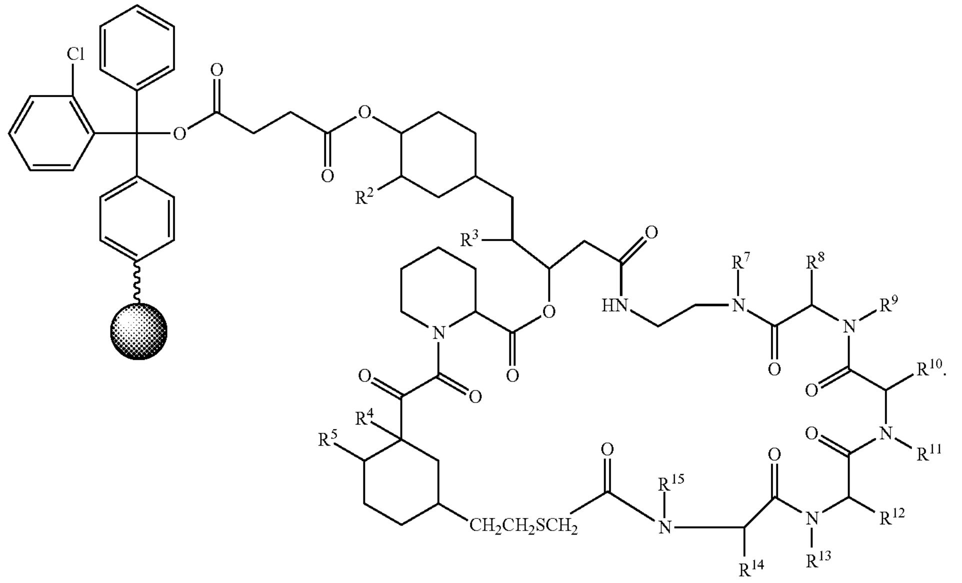

8. The method of claim 1 wherein the hyperproliferative disorder is selected from melanoma, skin cancer, breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, ovarian cancer, neurodegeneration, cardiac hypertrophy, pain, migraine, neurotraumatic diseases, stroke, diabetes, hepatomegaly, cardiovascular disease, Alzheimer's disease, cystic fibrosis, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, hyperproliferative disorders, infectious diseases, conditions associated with cell death, thrombin-induced platelet aggregation, chronic myelogenous leukemia (CML), liver disease, pathologic immune conditions involving T cell activation, CNS disorders, or a combination thereof.

* * * * *